(12) United States Patent
Schneider

(10) Patent No.: US 7,435,406 B2
(45) Date of Patent: Oct. 14, 2008

(54) METHODS FOR CONDUCTING METABOLIC ANALYSES

(75) Inventor: Luke V. Schneider, Half Moon Bay, CA (US)

(73) Assignee: Target Discovery, Inc., Palo Alto, CA (US)

( * ) Notice: Subject to any disclaimer, the term of this patent is extended or adjusted under 35 U.S.C. 154(b) by 0 days.

(21) Appl. No.: 11/018,871

(22) Filed: Dec. 20, 2004

(65) Prior Publication Data

US 2005/0153346 A1 Jul. 14, 2005

Related U.S. Application Data

(63) Continuation of application No. 10/687,909, filed on Oct. 17, 2003, now Pat. No. 6,849,396, which is a continuation of application No. 09/553,424, filed on Apr. 19, 2000, now Pat. No. 6,764,817.

(60) Provisional application No. 60/130,238, filed on Apr. 20, 1999.

(51) Int. Cl.
*A61K 51/00* (2006.01)

(52) U.S. Cl. ...................................... 424/1.33

(58) Field of Classification Search ............ 435/4, 435/7.72, 29, 968, 973; 204/450, 451
See application file for complete search history.

(56) References Cited

U.S. PATENT DOCUMENTS

| | | |
|---|---|---|
| 4,568,074 A | 2/1986 | Murayoshi |
| 4,647,445 A | 3/1987 | Lees |
| 4,656,133 A | 4/1987 | Goux |
| 4,690,749 A | 9/1987 | Van Alstine et al. |
| 4,725,343 A | 2/1988 | Hjerten et al. |
| 4,830,010 A | 5/1989 | Marshall |
| 4,842,701 A | 6/1989 | Smith et al. |
| 4,859,301 A | 8/1989 | Brenner et al. |
| 4,911,808 A | 3/1990 | Hjerten |
| 4,931,328 A | 6/1990 | Swedberg |
| 4,994,165 A | 2/1991 | Lee et al. |
| 4,997,536 A | 3/1991 | Ohms et al. |
| 5,015,350 A | 5/1991 | Wiktorowicz |
| 5,059,702 A | 10/1991 | Dooley et al. |
| 5,074,982 A | 12/1991 | Novotny et al. |
| 5,096,554 A | 3/1992 | Chin |
| 5,110,424 A | 5/1992 | Chin |
| 5,110,434 A | 5/1992 | Zhu et al. |
| 5,132,432 A | 7/1992 | Haugland et al. |
| 5,143,753 A | 9/1992 | Novotny et al. |
| 5,151,164 A | 9/1992 | Blanchard et al. |
| 5,180,475 A | 1/1993 | Young et al. |
| 5,181,999 A | 1/1993 | Wiktorowicz |
| 5,210,412 A | 5/1993 | Levis et al. |
| 5,240,585 A | 8/1993 | Young et al. |
| 5,262,031 A | 11/1993 | Lux et al. |
| 5,282,942 A | 2/1994 | Herrick |
| 5,290,587 A | 3/1994 | Young et al. |
| 5,306,412 A | 4/1994 | Whitehouse et al. |
| 5,314,593 A | 5/1994 | Swedberg |
| 5,317,156 A | 5/1994 | Cooper et al. |
| 5,320,727 A | 6/1994 | Jackson |
| 5,320,730 A | 6/1994 | Ewing et al. |
| 5,322,608 A | 6/1994 | Karger et al. |
| 5,338,686 A | 8/1994 | Hellerstein |
| 5,358,618 A | 10/1994 | Ewing et al. |
| 5,378,334 A | 1/1995 | Dadoo et al. |
| 5,386,832 A | 2/1995 | Wagner et al. |
| 5,391,274 A | 2/1995 | Shieh |
| 5,413,917 A | 5/1995 | Malloy et al. |
| 5,414,259 A | 5/1995 | Kingston |
| 5,415,747 A | 5/1995 | Holloway |
| 5,429,728 A | 7/1995 | Gordon |
| 5,439,803 A | 8/1995 | Ross et al. |
| 5,441,613 A | 8/1995 | McCormick |
| 5,447,617 A | 9/1995 | Shieh |

(Continued)

FOREIGN PATENT DOCUMENTS

EP 0617048 A1 9/1994

(Continued)

OTHER PUBLICATIONS

Sauer et al, Nature Biotechnology, vol. 15 (1997)(Abstract Only)(pp. 1-4).*
Brunengraber et al, Annual Review of Nutrition, vol. 17, pp. 559-596, (Abstract Only)(pp. 1-2).*
Dueker et al. Anal. Chem. 1994;4177-4185.*
Sheppard et al. Anal. Chem. 1997;69:2901-2907.*
Rahmani et al. "Chlorophyll and β-carotene pigment in moroccan virgin olive oils measured by high-performance liquid chromatography", 1991, JAOCS, 68(9):672-674.*
Baj, Jian et al. "Peptide Mapping by CNBr Degradation on a Nitrocellulose Membrane with Analysis by Matrix-Assisted Laser Desorption/Ionization Mass Spectrometry", *Analytical Chemistry*, May 15, 1995, vol. 67, No. 10, pp. 1705-1710.

(Continued)

*Primary Examiner*—Jon P Weber
*Assistant Examiner*—Bin Shen
(74) *Attorney, Agent, or Firm*—Townsend and Townsend and Crew

(57) ABSTRACT

The present invention provides methods and apparatus for purifying metabolites of interest and conducting metabolic analyses. The methods generally involve determining metabolic flux values for a plurality of target analytes by monitoring the relative isotope abundance of a stable isotope in a substrate labeled with the stable isotope and/or one or more target metabolites formed through metabolism of the labeled substrate. Certain methods utilize multiple electrophoretic methods to separate the target analytes from other components within the sample being analyzed. The methods can be used in a variety of applications including screens to identify metabolites that are correlated with certain diseases and diagnostic screens for identifying individuals having, or susceptible to, a disease.

13 Claims, 28 Drawing Sheets

U.S. PATENT DOCUMENTS

| | | | |
|---|---|---|---|
| 5,462,646 | A | 10/1995 | Shieh |
| 5,470,753 | A | 11/1995 | Sepetov et al. |
| 5,505,832 | A | 4/1996 | Laukien et al. |
| 5,516,636 | A | 5/1996 | McCapra |
| 5,538,897 | A | 7/1996 | Yates, III et al. |
| 5,542,419 | A | 8/1996 | Moulton-Barrett et al. |
| 5,552,541 | A | 9/1996 | Adams |
| 5,599,432 | A | 2/1997 | Manz et al. |
| 5,611,903 | A | 3/1997 | Janssens et al. |
| 5,705,622 | A | 1/1998 | Cerri et al. |
| 5,784,154 | A | 7/1998 | Pawliszyn |
| 5,792,331 | A | 8/1998 | Srinivasan et al. |
| 5,827,659 | A | 10/1998 | Patterson |
| 5,837,116 | A | 11/1998 | Harrington et al. |
| 5,837,219 | A | 11/1998 | Watanabe et al. |
| 5,840,388 | A | 11/1998 | Karger et al. |
| 5,856,082 | A | 1/1999 | Aebersold et al. |
| 5,872,010 | A | 2/1999 | Karger et al. |
| 5,910,403 | A | 6/1999 | Hellerstein |
| 5,916,537 | A | 6/1999 | Kajiwara et al. |
| 5,919,709 | A | 7/1999 | Parmelee et al. |
| 5,924,995 | A | 7/1999 | Klein et al. |
| 5,985,121 | A | 11/1999 | Wu et al. |
| 5,993,627 | A | 11/1999 | Anderson et al. |
| 6,004,770 | A | 12/1999 | Nelson |
| 6,010,846 | A | 1/2000 | Hellerstein |
| 6,013,165 | A | 1/2000 | Wiktorowicz et al. |
| 6,017,693 | A | 1/2000 | Yates, III et al. |
| 6,027,890 | A | 2/2000 | Ness et al. |
| 6,074,542 | A | 6/2000 | Dolnik et al. |
| 6,103,199 | A | 8/2000 | Bjornson et al. |
| 6,207,464 | B1 | 3/2001 | Karandikar |
| 6,277,644 | B1 | 8/2001 | Farnsworth et al. |
| 6,297,099 | B1 | 10/2001 | Hsieh et al. |
| 6,329,146 | B1 | 12/2001 | Crooke et al. |
| 6,335,525 | B1 | 1/2002 | Takada et al. |
| 6,355,416 | B1 | 3/2002 | Abramson |
| 6,372,353 | B2 | 4/2002 | Karger et al. |
| 6,375,818 | B1 | 4/2002 | Huang et al. |
| 6,379,971 | B1 | 4/2002 | Schneider et al. |
| 6,537,432 | B1 | 3/2003 | Schneider et al. |
| 6,677,114 | B1 | 1/2004 | Schneider et al. |
| 6,764,817 | B1 * | 7/2004 | Schneider ............. 435/4 |
| 6,818,112 | B2 | 11/2004 | Schneider et al. |
| 6,849,396 | B2 * | 2/2005 | Schneider ............. 435/4 |
| 2003/0199751 | A1 | 10/2003 | Gonzalez et al. |
| 2004/0091943 | A1 | 5/2004 | Schneider |

FOREIGN PATENT DOCUMENTS

| | | | |
|---|---|---|---|
| WO | WO 95/33989 A1 | 12/1995 | |
| WO | WO 96/33406 A1 | 10/1996 | |
| WO | WO 98/51820 A1 | 11/1998 | |
| WO | WO 99/32501 A1 | 7/1999 | |
| WO | WO 00/11208 A1 | 3/2000 | |
| WO | WO 02/061681 A2 | 8/2002 | |

OTHER PUBLICATIONS

Bochner, et al., "Complete Analysis of Cellular Nucleotides by Two-dimensional Thin Layer Chromatography," *J. Bio. Chem.* 257(16):9759-9769 (1982).

Chen, Xiaohui et al. "Isotope Edited Product Ion Assignment by α-N Labelling of Peptides with [$^2$H$_3$(50%)2,4-Dinitrofluorobenzene", *J. Am. Soc. Mass Spectrum*, (1999), vol. 10, pp. 448-542.

Eckerskorn, C.et al. "Analysis of Proteins by Direct-Scanning Infra-red-MALDI Mass Spectrometry after 2D-PAGE Separation and Electroblotting", *Anal. Chem.*, (1997), vol. 69, pp. 2888-2892.

Gausing, K. "Ribosomal Protein in *E. coli*: Rate of Synthesis and Pool Size at Different Growth Rates," *Mol. Gen. Genetics*, 129:61-75 (1974).

Ghoos, Yvo et al. "Measurement of gastric emptying rate of solids by means of a carbon-labeled octanoic acid breath test." Gastroenterology, 1993, pp. 1640-1647, vol. 104.

Goodlett, D.R. et al. "The Use of Mass Spectrometry In Proteomics"; *International Business Communications*, Pre-conference Symposium Slides, Wednesday, Dec. 1, 1999, pp. 1-11.

Gygi, Steven P. et al. "Quantitative Analysis of Complex Protein Mixtures Using Isotope-coded Affinity Tags", *Nature Biotechnology*, Oct. 1999, vol. 17, pp. 994-999.

Gygi, Steven P. "Functional Proteomics—Advances in the Development of Drug Leads and Diagnostic Applications Using Integrated Protein-Based Technologies—Slides", *International Business Communications*, 4th International Conference Slides, Dec. 1-3, 1999, pp. 1-11.

Hachey, David et al. "Isotope Ratio Measurements In Nutrition and Biomedical-research." Mass Spectrometry Reviews, 1987, pp. 289-328, vol. 6.

Håkansson, Kristina, et al; Electron Capture Dissodation and Infra-red Multiphoton Dissociation MS/MS of an N-Glycosylated Tryptic Peptide to Yield Complementary Sequence Information; *Analytical Chemistry*; Sep. 15, 2001; pp. 4530-4536; vol. 73, No. 18.

Henry, Kent D., et al.; Electrospray Ionization with Fourier-Transform Mass Spectrometry. Charge State Assignment from Resolved Isotopic Peaks; *Organic Mass Spectrometry*; 1990; pp. 490-492; vol. 25.

Henzel, W.J. et al. "Identifying Proteins from Two-dimensional Gels by Molecular Mass Searching of Peptide Fragments in Protein Sequence Databases", *Proc. Natl. Acad. Sci. USA*, Jun. 1993, vol. 90, pp. 5011-5015.

Hochstrasser, et al. "Methods for Increasing the Resolution of Two-Dimensional Protein Electrophoresis," *Anal. Biochem.*, 173:424-435 (1988).

Huang, Z-H. et al.; "Protein Sequencing by Matrix-Assisted Laser Desorption Ionization-Postsource Decay-Mass Spectrometry Analysis of the N-Tris(2,4,6-trimethoxyphenyl)phosphine-Acetylated Tryptic Digests", *Analytical Biochemistry* (1999), vol. 268, pp. 305-317.

Jensen, Ole et al. "Sequence Patterns Produced by Incomplete Ezymatic Digestion or One-step Edman Degradation of Peptide Mixture as Probes for Protein Database Searches" *Electrophoresis* (1996) vol. 15(5); pp. 938-944.

Jensen, P.K. et al.; "Probing Proteomes Using Capillary Isoelectric Focusing-Electrospray Ionization Fourier Transform Ion Cyclotron Resonance Mass Spectrometry", *Anal. Chem.*, Jun. 1, 1999, vol. 71, No. 11, pp. 2076-2084.

Kelm, Mark et al. "Quantitative determination of 13C-labeled and endogenous beta-carotene, lutein, and vitamin A in human plasma." Lipids, 2001, 36(11): 1277-1282.

Kilar, Ference: Isoelectric Focusing in Capillaries (Chapter 4), *CRC Handbook of Capillary Electrophoresis: A Practical Approach*, (1994), pp. 95-109.

Kriwacki Richard W., et al; Probing Protein/Protein Interactions with Mass Spectrometry and Isotopic Labelling: Analysis of the p21/Cdk2 Complex; *Journal of the American Chemical Society*; 1996; pp. 5320-5321; vol. 118.

Li et al. "Improvements on Sample Handling for Rapid Mass Spectrometric Identification of Proteins Resolved by 2D Gel Electrophoresis" *Book of Abstracts, 213th ACS National Meeting*, San Francisco (Apr. 13-17, 1997).

Mann, et al. "Error-Tolerant Identification of Peptides in Sequence Databases by Peptide Sequence Tags" *Analytical Chemistry* (Dec. 15, 1994) vol. 66(24), pp. 4390-4399.

Marshall, Alan G., et al; Protein Molecular Mass to 1 Da by $^{13}$C, $^{15}$N Double-Depletion and FT-ICR Mass Spectrometry; *Journal of the American Chemical Society*; 1997; pp. 433-434; vol. 119.

McCormick, Randy M., Capillary Zone Electrophoresis of Peptides (Chapter 12), *CRC Handbook of Capillary Electrophoresis: A Practical Approach*, (1994), pp. 287-323.

Mirgorodskaya, E., et al; Localization of O-Glycosylation Sites in Peptides by Electron Capture Dissociation in a Fourier Transform Mass Spectrometer; *Analytical Chemistry*; Oct. 15, 1999; pp. 4431-4436; vol. 71, No. 20.

Murphy, Constance M. & Fenselau, Catherine; Recognition of the Carboxy-Terminal Peptide in Cyanogen Bromide Digests of Proteins, *Anal. Chem.*, (1995), vol. 67, pp. 1644-1645.

Nath et al., "Protein Degradation in *Escherichia coli*," *J. Biol. Chem.*, 246(22):6956-6967 (1971).

O'Farrel, P.H., "High Resolution Two-Dimensional Electrophoresis of Proteins," *J. Biol. Chem.*, 250(10):4007-4021 (1975).

Palmieri, Richard & Nolan, Judith A. Protein Capillary Electrophoresis: Theoretical and Experimental Considerations for Methods Development (Chapter 13), *Handbook of Capillary Electrophoresis*, (1994), pp. 325-368.

Patterson, Scott D. & Aebersold, Ruedi; Mass Spectrometric Approaches for the Identification of Gel-separated Proteins, *Electrophoresis*, (1995), vol. 16, pp. 1791-1814.

Rittenberg, D. & Schoenheimer, Rudolf "Deuterium as an Indicator in the study of intermediary metabolism XI. Further studies on the biological uptake of deuterium into organic substances, with special reference to fat and cholesterol formation" J. Biol. Chem., Oct. 1937; 121:235-253.

Schneider, Luke V.; Presentation Slides from *Cambridge Healthtech Institutes's Second Annual Genomic Partnering Emerging and Early-Stage Companies*, Feb. 27-28, 1999, pp. 1-7.

Schneider, Luke V. "Metabolic Uncoupling in *Escherichia coli* During Phospate-limited Growth," Ph.D. Thesis (Princeton University, Princeton, N.J., A Dissertation presented to the Faculty of Princeton University in Candidacy for the Degree of Doctor of Philosophy 2:LV-CXII (1997).

Schoenheimer, Rudolf & Rittenberg, D. "Deuterium as an indicator in the study of intermediary metabolism" Science, Aug. 1935, vol. 82, No. 2120, p. 156-157.

Schoenheimer, Rudolf et al. "Studies in Protien Metabolism X. The metabolic activity of body proteins investigated with I (-)-leucine containing two isotopes" J. Biol. Chem., Oct. 1939; 130: 703-732.

Shevchenko, A. et al. "Linking Genome and Proteome by Mass Spectrometry: Large-Scale Identification of Yeast Proteins from Two Dimensional Gels", *Proc. Natl. Acad. Sci. USA*, Dec. 1996, vol. 93, pp. 14440-14445.

Smith, R.D. et al. Capillary Electrophoresis-Mass Spectrometry (Chapter 8), *CRC Handbook of Capillary Electrophoresis: A Practical Approach*, (1994), pp. 185-206.

St. John, et al. "Effects of Starvation for Potassium and Other Inorganic Ions on Protein Degradation and Ribonucleic Acid Synthesis in *Escherichia coli*," *J. Bacteriol*, 143(3):1223-1233 (1980).

Stensballe, Allan, et al; "Electron capture dissociation of singly and multiply phosphorylated peptides"; *Rapid Communications in Mass Spectrometry*; 2000; pp. 1793-1800; vol. 14.

Stults, J.T. et al. "Simplification of High-Energy Collision Spectra of Peptides by Amino-Terminal Derivatization", *Anal. Chem.*, (1993), vol. 65, pp. 1703-1708.

Veenstra, Timothy D., et al; Proteome Analysis Using Selective Incorporation of Isotopically Labeled Amino Acids; *Journal of the American Society for Mass Spectrometry*; 2000; pp. 78-82.

Wagner, D.S. et al. "Derivatization of Peptides to Enhance Ionization Efficiency and Control Fragmentation During Analysis by Fast Atom Bombardment Tandem Mass Spectrometry", *Biological Mass Spectrometry*, (1991), vol. 20, pp. 419-425.

U.S. Appl. No. 60/415,481, filed Oct. 1, 2002, Soren Ebdrup.

Aebersold et al., "Design, Synthesis, and Characterization of a Protein Sequencing Reagent Yielding Amino Acid Derivatives with Enhanced Detectability by Mass Spectrometry," *Protein Science* 1992 vol. 1 pp. 494-503.

Biemann, Klaus, "Sequencing of Peptides By Tandem Mass Spectrometry and High Energy Collision-Induced Dissociation," *Methods in Enzymology* 1990 vol. 193 pp. 455-479.

Bures et al., "Synthesis of the Protein-Sequencing Reagent 4-(3-Pyridinylmethylaminocarboxypropyl) Phenyl Isothiocyanate and Characterization of 4-(3-Pyridinylmethylaminocarboxypropyl) Phenylthiohydantoins," *Analytical Biochemistry* 1995 vol. 224 pp. 264-372.

Clauser, et al., "Rapid Mass Spectrometry Peptide Sequencing and Mass Matching for Characterization of Human Melanoma Proteins Isolated by Two-Dimensional PAGE," *Biochemistry* May 1995 vol. 92 pp. 5072-5076.

Escoubas, et al., "Multidimensional Peptide Fingerprinting by High Performance Liquid Chromatography, Capillary Zone Electrophoresis and Matrix-Assisted Laser Desorption/Ionization..." *Rapid Communications in Mass Spectrometry* 1998 vol. 12 No. 16 pp. 1075-1084 (1998).

Huhmer et al., "Separation and Analysis of Peptides and Proteins," *Analytical Chemistry* 1997 vol. 69 pp. 29R-57R.

Johnson et al., "Collision-Induced Fragmentation of $(M+H)^+$ Ions of Peptides. Side Chain Specific Sequence Ions," *International Journal of Mass Spectrometry and Ion Processes* 1988 vol. 86 pp. 137-154.

Neubauer et al., "Identification of the Proteins of the Yeast U1 Small Nuclear Ribonucleoprotein Complex by Mass Spectrometry," *Proceedings of the National Academy of Science* 1997 vol. 94 pp. 385-390.

Rose et al., "C-Terminal Peptide Identification by Fast Atom Bombardment Mass Spectrometry," *Biochemistry Journal* 1998 vol. 250 pp. 253-259.

Shaffer Catherine, "Mass Spec and Metabolomics Are a Powerful Combination" *Genomic and Proteomics* Sep. 2005 p. 23.

Schasfoort et al., "Field Effects Flow Control for Microfabricated Fluidic Networks," *Science*, Oct. 29, 1999, vol. 286, p. 942.

Schnöler et al., "Protease-Catalyzed Incorporation of $^{18}O$ into Peptide Fragments and Its Application for Protein Sequencing by Electrospray and Matrix-Assisted Laser Desorption/Ionization Mass Spectrometry," *Electrophoresis* 1996 vol. 17, pp. 945-953.

Scholz et al., "Characterization of a Basement Membrane Protein (BM180) Using Capillary Electrophoresis," *Capillary Electrophoresis* 1997 vol. 4, pp. 287-292.

Shecvhenko, et al., "Linking Genome and Proteome by Mass Spectrometry: Large-scale Identification of Yeast Proteins from Two Dimensional Gels," *Proceedings of the National Academy of Science* 1996 vol. 93 pp. 14440-14445.

Target Discovery, Inc., "MetaSIRMS™ Stable Isotope Ratio Metabolomics" *Target Discovery: From Omics to Knowmics* 2004 pp. 1-9.

Tang, et al., "Two-Dimensional Analysis of Recombinant *E. coli* Proteins Using Capillary Isoelectric Focusing Electrospray Ionization Mass Spectrometry", *Analytical Chemistry* 1997 vol. 69, pp. 3177-3182.

Tomer et al., "Location of Double Bond Position in Unsaturated Fatty cids by Negative Ion MS/MS," *Journal of American Chemistry Society* 1983 vol. 105, pp. 5487-5488.

Vath, James E., "Method for the Derivation of Organic Compounds at the Sub-Nanomole Level with Reagent Vapor," *Analytical Chemistry* 1988 vol. 331 pp. 248-252.

Wagner et al., "Derivation of Peptides to Enhance Ionization Efficiency and Control Fragmentation During Analysis by Fast Atom Bombardment Tandem Mass Spectrometry," *Biological Mass Spectrometry* 1991 vol. 20 pp. 419-425.

Wu et al, "Flourescent Imaging Detection for Capillary Isoelectric Focusing," *Electrophoresis*, 1995 vol. 16 No. 8, pp. 1474-1478.

Yates III, et al., "Peptide Mass Maps: A Highly Informative Approach to Protein Identification," *Analytical Biochemistry* 1993 vol. 214 vol. 214 pp. 397-408.

Zaia et al., "Comparison of Charge Derivatives for High Energy Collision-Induced Dissociation Tandem Mass Spectrometry" *American Society for Mass Spectrometry* 1995 vol. 6 pp. 428-436.

Wanders, B.J. and Everaerts, F.M. Isotachophoresis in Capillary Electrophoresis (Chapter 5), *CRC Handbook of Capillary Electrophoresis: A Practical Approach*, (1994), pp. 111-127.

Wilkins, et al. "Protein Identification with N and C-terminal Sequence Tags in Proteome Projects" *J. Mol. Biol.* (1998) vol. 278(3), pp. 599-608.

Wilkins, et al. "Protein Identification with Sequence Tags" *Current Biology* (1996) vol. 6(12), pp. 1543-1544.

Wilkins, et al. "Rapid Protein Identification Using N-terminal 'Sequence Tag' and Amino Acid Analysis" *Biochemical and Biophysical Research Communications* (1996) vol. 221(3), pp. 609-613.

Zaia, Joseph, Charged Derivatives for Peptide Sequencing Using a Magnetic Sector Instrument, *Methods in Molecular Biology*, vol. 61, pp. 28-40. 1996.

\* cited by examiner

METHODS FOR CONDUCTING METABOLIC ANALYSES

CROSS-REFERENCES TO RELATED APPLICATIONS

This application is a continuation of U.S. application Ser. No. 10/687,909, filed Oct. 17. 2003, now U.S. Pat. No. 6,849, 396 which is a continuation of U.S. application Ser. No. 09/553,424, filed Apr. 19, 2000, now U.S. Pat. No. 6,764,817 which claims the benefit of U.S. provisional application 60/130,238, filed Apr. 20, 1999. This application is also related to U.S. provisional application 60/075,715 filed Feb. 24, 1998; copending U.S. patent application number Ser. No. 09/513,486, filed Feb. 25, 2000; copending U.S. patent application Ser. No. 09/513,395, filed Feb. 25, 2000; copending U.S. application Ser. No. 09/513,907, filed Feb., 25,2000; copending U.S. patent application Ser. No. 09/551,937, filed Apr. 19, 2000; and copending PCT application PCT/ US01/ 10504, filed Apr. 19, 2000. All of these applications are incorporated by reference in their entirety for all purposes.

FIELD OF THE INVENTION

This invention relates to the field of metabolism and separation technology, including methods for separating and analyzing metabolites and making correlations between certain metabolites or metabolic conditions and cellular states.

BACKGROUND OF THE INVENTION

One goal in biochemical research is to develop correlations between the presence, absence, concentration, conversion rates, or transport rates of certain molecules within cells, tissues and particular cell or tissue states (e.g., disease states, particular developmental stages, states resulting from exposure to certain environmental stimuli and states associated with therapeutic treatments). Such correlations have the potential to provide significant insight into the mechanism of disease, cellular development and differentiation, as well as in the identification of new therapeutics, drug targets and/or disease markers.

Genomics based studies are an example of one type of approach taken in such investigations. Typically, functional genomics focuses on the change in mRNA levels as being indicative of a cellular response to a particular condition or state. Recent research, however, has demonstrated that often there is a poor correlation between gene expression as measured by mRNA levels and active gene product formed (i.e., protein encoded by the mRNA). This finding is not particularly surprising since many factors—including differences in translational efficiency, turnover rates, extracellular expression or compartmentalization, and post-translational modification affect protein levels independently of transcriptional controls.

Another approach is proteomics which, as the term implies, focuses on the proteins present in various cellular states. The rationale for conducting proteomics investigations is based in part upon the view that certain aspects of cellular biology can be better understood by taking inventory of protein levels rather than nucleic acids levels, particularly given the findings just described that suggest that protein activity often hinges on factors other than the concentration of mRNA encoding the protein.

Instead of focusing exclusively on either nucleic acids or proteins, the current invention takes a different approach and examines the metabolites present in a cell formed through cellular metabolism. Such an approach is termed metomics. More specifically, metomics refers to the study of metabolic fluxes and changes in these fluxes as a function of the physiological state of an organism (or population of cells or tissue). Metomics studies can involve, for example, identifying specific metabolic patterns that cause or result from changes in the physiological state of an organism or cell population. Metomics studies can be correlated to changes in protein and mRNA expression patterns also resulting from changes in the physiological state of an organism or cell population.

Metabolism consists of a complex network of catabolic (energy and precursor producing) and anabolic (biosynthetic) enzymatic pathways that together support the maintenance and growth of the cell. The flow of chemicals through this network of enzymatic reactions ovaries with the cell cycle; (Ingraham, J. L., et al., *Growth of the Bacterial Cell*, Sinauer Associates, Sunderland, Mass., (1983)) diet, availability of extracellular nutrients, and exposure to cellular stresses (e.g., chemical and biochemical toxins or infectious agents). The major metabolic pathways and factors in their regulation are discussed in any general biochemical text book including, for example, Voet, D. and Voet, J. G., *Biochemistry*, John Wiley & Sons, New York (1990); Stryer, L., *Biochemistry*, 2nd ed., W.H. Freeman and Company, San Francisco (1981); and White, A., et al., *Principles of Biochemistry*, 6th ed., McGraw-Hill Book Company (1978), each of which is incorporated by reference in its entirety.

Because metabolism must be capable of adapting to varying conditions and stimuli, cells have a variety of mechanisms at their disposal to regulate metabolism. For example, certain regulatory mechanisms control the rate at which metabolites enter a cell. Since very few substances are capable of diffusing across a cellular membrane, such regulation typically occurs via one of the active or passive transport mechanisms of a cell.

In addition to transport control, a number of different mechanisms can function to regulate the activity of an enzyme that is part of a metabolic pathway. For example, a product produced by the enzyme can act via feedback inhibition to regulate the activity of the enzyme. Enzymes can also be regulated by ligands that bind at allosteric sites (i.e., sites other than the active site of the enzyme). It has been suggested that allosteric regulation is important in quick time responses (times less than that required for the induction and synthesis of new proteins, <10 min), as well as in the modulation of enzyme activity to changes in background requirements (feed-back control) (Chock, P. B., et al., *Current Topics in Cellular Regulation.*, 27:3 (1985); Koshland, D. E., et al., *Science*, 217:220 (1982); Stadtman, E. R. and Chock, P. B., *Current Topics in Cellular Regulation*, 13:53 (1978)). Allosteric regulation is the primary method used by bacteria to sense their environment, both by activity modulation of already synthesized proteins and by eliciting new protein synthesis via control of RNA polymerase promoter and repressor proteins (Monod, J., et al., *J. Mol. Biol.*, 6:306 (1963)). Allosteric regulation can be associated with multimeric proteins (several subunits working in a concerted fashion) and/or within regulatory cascades in order to: (1) provide more sites for different regulatory ligands to affect activity, (2) amplify the rate of response, (3) amplify the magnitude of response, and/or (4) amplify the sensitivity of response (Chock, P. B., et al., *Current Topics in Cellular Regulation.*, 27:3 (1985); Koshland, D. E., et al., *Science*, 217:220 (1982); Stadtman, E. R. and Chock, P. B., *Current Topics in Cellular Regulation*, 13:53 (1978)).

Expression regulation constitutes another metabolic regulatory mechanism. Concerted sets of genes, encoding small numbers of proteins, are often organized under the same transcriptional control sequence called an operon. However, where the necessary adaptive changes entail the induction of large numbers of proteins, many such operons can be linked in regulons. For example, in *E. coli* the following stimuli induce the number of proteins indicated in parentheses: (a) heat shock (17 proteins), (b) nitrogen starvation ($\geqq 5$ proteins), (c) phosphate starvation ($\geqq 82$ proteins), (d) osmotic stress ($\geqq 12$ proteins), and (e) SOS response (17 proteins) (see, Neidhardt, F. C., in: *Escherichia coli and Salmonella typhimurium: cellular and molecular biology*, F. C. Neidhardt et al. (eds.), pg. 3, Amer Soc Microbiology, Washington, D.C., (1987); Neidhardt, F. C. and Van Bogelen, R. A., in: *Escherichia coli and Salmonella typhimurium Cellular and Molecular Biology.*, F. C. Neidhardt (ed.)., pg 1334, American Society of Microbiology, Washington, D. C., (1987); Magasanik, B. and Neidhardt, F. C., in *Escherichia coli and Salmonella typhimurium Cellular and Molecular Biology.*, F. C. Neidhardt (ed.), pg 1318, American Society of Microbiology, Washington, D.C., (1987); (VanBogelen, R. A., et al., *Electrophoresis*, 11:1131 (1990)); Wanner, B. L., in: *Escherichia coli and Salmonella typhimurium Cellular and Molecular Biology*, F. C. Neidhardt (ed.), pg 1326, American Society of Microbiology, Washington, D.C., (1987)); (Christman, M. F. et. al, *Cell*, 14:753 (1985); and Walker, G. C., in *Escherichia coli and Salmonella typhimurium Cellular and Molecular Biology*, F. C. Neidhardt (ed.), pg 1346, American Society of Microbiology, Washington, D.C., (1987)). Thus, regulons enable cells to regulate genes that need to respond occasionally in a concerted fashion to a particular stimulus, but that at other times need to be independently responsive to individual controls (Neidhardt, F. C., in: *Escherichia coli and Salmonella typhimurium: cellular and molecular biology*, F. C. Neidhardt et al. (eds.), pg. 3, Amer Soc Microbiology, Washington, D.C., (1987)).

Degradation is another regulatory mechanism for controlling metabolism. Most proteins are very stable, at least under conditions of balanced growth, probably because the cell pays such a high price to make them. However, several researchers have observed a limited class of cellular proteins (10 to 30% of the total protein present during exponential growth in bacteria) that is unstable (exhibit half-lives of 60 min or less). Proteins within the class appear to be turned over quickly within 10 hours of any growth down shift, and during exponential growth (Nath K. and Koch. A. L., *J. Biol. Chem.*, 246:6956 (1971); St. John, A. C. and Goldberg, A. L., *J. Bacteriol.*, 143:1223 (1980)). At least some of these labile proteins, during energy and nutrient down-shifts, are proteins of the protein synthesizing system (e.g., ribosomal proteins) (Davis, B. D., et al., *J. Bacteriol.*, 166:439 (1986)); Ingraham, J. L., et al., *Growth of the Bacterial Cell*, Sinauer Associates, Sunderland, Mass., (1983); Maruyama, H. B. and Okamura, S., *J. Bacteriol.*, 110:442 (1972)). This conclusion is drawn from the observations that the apparent rate of protein synthesis per unit of protein synthesizing proteins decreases at low growth rates, but the time required for the initial synthesis of inducible enzymes remains constant at all growth rates (Ingraham, J. L., et al., *Growth of the Bacterial Cell*, Sinauer Associates, Sunderland, Mass. (1983)).

Given the interrelatedness between different cell states and metabolism and the fact that the focus of metomics differs from genomics and proteomics, the present invention utilizes metomic studies to gain new insight into the correlation between cellular states and the biomolecules within the cell.

SUMMARY OF THE INVENTION

The present invention provides apparatus and methods that have utility in purifying and detecting metabolites of interest. The purifying and detection methods enable one to determine how various parameters for metabolites of interest (e.g., metabolite concentration and/or flux) vary as a function of different cellular states or exposure to different stimuli. Thus, the methods can be used to screen for metabolites that are correlated with particular cellular states or stimuli. Such information can be used to develop metabolic "fingerprints" or "profiles" that are characteristic of different cellular states and/or responses to particular stimuli. The information can also be used to develop metomics databases. Once correlations, have been established, certain methods of the invention can be utilized to screen for particular states. For example, some methods screen individuals to identify those having, or at risk, for a particular disease based upon similarities between their metabolic profile and that of diseased and/or healthy individuals.

More specifically, the invention includes various separation methods. Certain methods involve performing a plurality of capillary electrophoresis methods in series. Each method in the series includes electrophoresing a sample containing multiple metabolites and potentially one or more target analytes of interest so that a plurality of resolved metabolites are obtained. The sample electrophoresed in each method contains only a subset of the plurality of resolved metabolites from the immediately preceding method in the series, except the first method of the series in which the sample is the initial sample. Fractions containing resolved metabolites from the final electrophoretic method are analyzed to detect the presence of the target analytes. The capillary electrophoresis methods within the series are selected from the group consisting of capillary isoelectric focusing electrophoresis, capillary zone electrophoresis and capillary gel electrophoresis.

In certain aspects, the invention provides various methods for analyzing metabolic pathways. Certain methods involve administering a substrate labeled with a stable isotope to a subject, the relative isotopic abundance of the isotope in the substrate being known prior to administering the substrate. The subject is then allowed sufficient time to at least partially metabolize the labeled substrate to form one or more target metabolites. The abundance of the isotope in a plurality of target analytes in a sample taken from the subject is then determined so that a value for the flux of each target analytes can be ascertained. The multiple target analytes for which a flux value is determined are either the substrate and/or one or more target metabolites. The abundance of the isotope in the target analytes is determined using an analyzer capable of determining the ratio of the isotopically enriched isotope to the more abundant isotope (e.g., $^{12}C/^{13}C$, $^{14}N/^{15}N$, $^{16}O/^{18}O$ and $^{34}S/^{32}S$). Examples of such analyzers include mass spectrometers, infrared spectrometers and nuclear magnetic resonance spectrometers.

Prior to determining the abundance of the isotope in the target analytes and corresponding flux values, typically the target analytes are at least partially separated from other components in the sample. Generally this is accomplished by performing a plurality of electrophoretic separation methods in series, such that samples from fractions obtained after one method are used in a subsequent electrophoretic method. The actual electrophoretic methods employed can vary, but typically include capillary isoelectric focusing electrophoresis, capillary zone electrophoresis and capillary gel electrophoresis. In some instances, separation and elution conditions of the electrophoretic methods are controlled so that separate fractions for one or more classes of metabolites (e.g., proteins, polysaccharides, carbohydrates, nucleic acids amino acids, nucleotides, nucleosides, fats, fatty acids, and organic acids) are obtained. This simplifies the analysis because one can simply analyze those fractions containing the class of components to which the target analytes belong.

The invention also provides analytic methods for analyzing metabolic pathways in which samples from a subject have been previously obtained. In such instances, certain methods involve separating at least partially a plurality of target analytes from other components contained in the sample obtained from the subject. The target analytes comprise a substrate labeled with a stable isotope and/or one or more target metabolites resulting from the metabolism of the substrate by the subject. A flux value for each target analyte is determined from knowledge of the isotopic abundance in the substrate prior to it being administered to the subject and by determining the abundance of the isotope in the target analytes.

Methods for screening metabolites to identify those correlated with various cellular states (e.g., certain diseases) are also included in the invention. Certain screening methods include administering a substrate labeled with a stable isotope to a test subject and a control subject, the relative isotopic abundance of the isotope in the substrate being known and the test subject having a disease under investigation. The labeled substrate is allowed to be at least partially metabolized by the test subject and control subject to form one or more target metabolites. The conditions under which the administering and allowing steps are performed are controlled so that they are the same for the test and control subject. A sample is obtained from the test and control subject and the relative abundance of the isotope in the target analytes determined to obtain a value for the flux of each target analyte. The flux values for the test and control subject are compared, a difference in the flux value for a target analyte in the test subject and corresponding flux value for the control subject indicating that such analyte is potentially correlated with the disease being studied.

When a sample has been previously acquired, certain screening methods involve analyzing a sample from a test subject having a disease, the sample comprising a substrate labeled with a stable isotope administered to the test subject and/or one or more target metabolites resulting from metabolism of the substrate by the test subject The relative isotopic abundance of the isotope in the substrate is known at the time of administration, and the analyzing step includes determining the isotopic abundance of the isotope in a plurality of target analytes in the sample to determine a value for the flux of each target analyte. Flux values for the target analytes in the test subject are compared with flux values for a control subject, a difference in a flux value indicating that such analyte is correlated with the disease.

In another aspect, the invention includes methods for screening for the presence of a disease. Certain of these methods involve administering to a test subject a substrate labeled with a stable isotope, the relative abundance of the isotope in the substrate being known. Sufficient time is allowed for the labeled substrate to be at least partially metabolized by the test subject to form one or more target metabolites known to be correlated with the disease. A plurality of electrophoretic methods are performed in series to at least partially separate a plurality of target analytes from other biological components in a sample obtained from the test subject, the target analytes comprising the substrate and/or one or more of the target metabolites. Flux values for the target analytes are determined from the abundance of the isotope in that analyte.

The method is simplified when sample is-provided. In such instances, certain method include analyzing a sample from a test subject, the sample comprising a substrate labeled with a stable isotope administered to the test subject and/or one or more target metabolites resulting from metabolism of the substrate by the test subject, the relative isotopic abundance of the isotope in the substrate known at the time of administration. The analyzing step itself comprises determining the abundance of the isotope in a plurality of analytes in the sample to determine a value for the flux of each analyte, the plurality of analytes comprising the substrate and/or one or more of the target metabolites. For each target analyte, the determined flux value is compared with a corresponding reference flux value for the same target analytes to assess the test subject's risk of disease. The reference value can be representative of a healthy or diseased state.

DETAILED DESCRIPTION

I. Definitions

Figure 1:
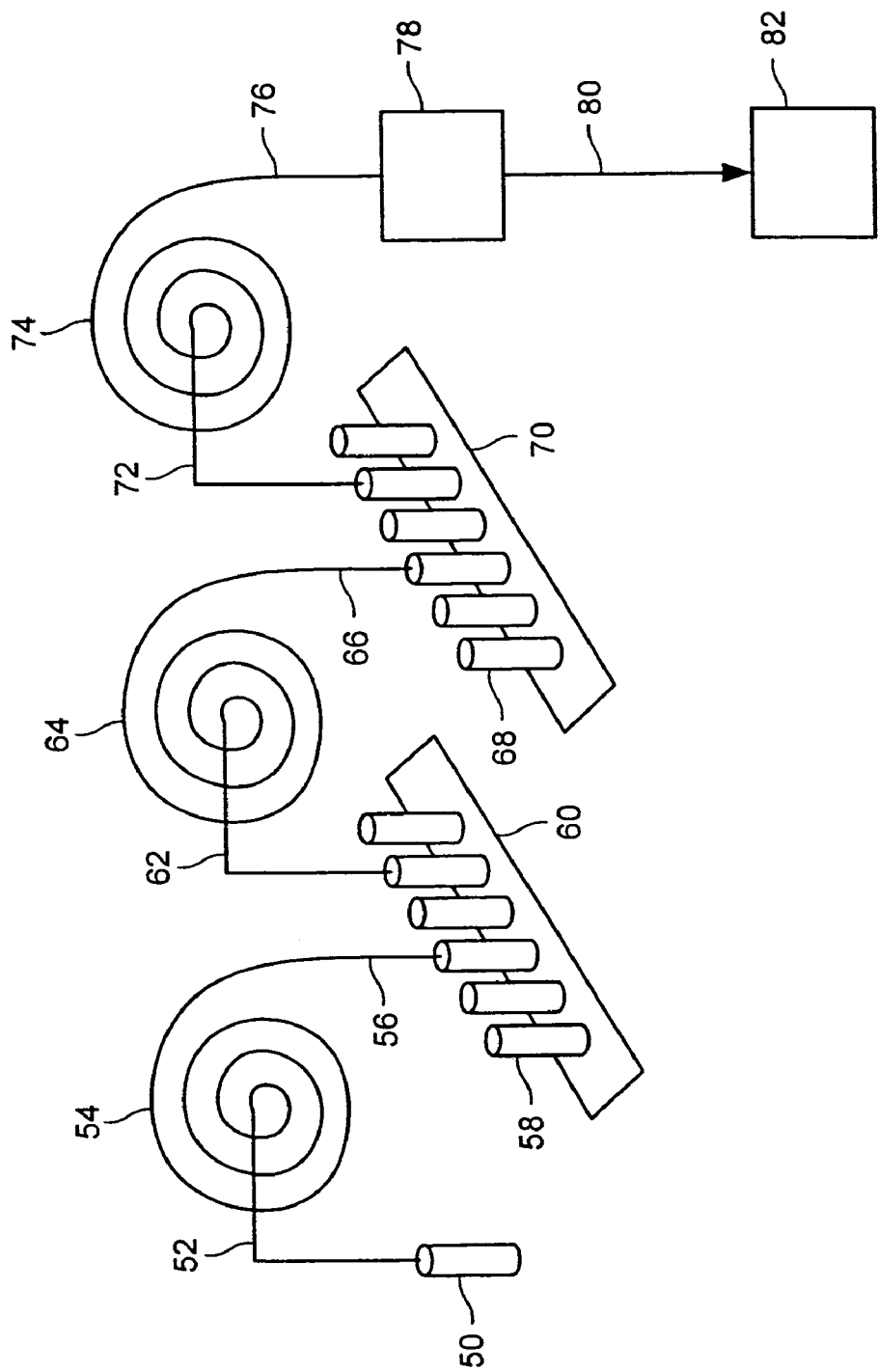
FIG. 1 is a schematic representation of one example of an electrophoretic system that can be utilized with certain methods of the invention.

Unless defined otherwise, all technical and scientific terms used herein generally have the same meaning as commonly understood by one of ordinary skill in the art to which this invention belongs. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference in its entirety), that are provided throughout this document.

Discussions of the various classes of metabolic compounds referenced herein can be found in any general biochemistry text book, including, for example, Voet, D. and Voet, J. G., *Biochemistry*, John Wiley & Sons, New York (1990); Stryer, L., *Biochemistry*, 2nd ed., W.H. Freeman and Company, San Francisco (1981); and White, A., et al., *Principles of Biochemistry*, 6th ed., McGraw-Hill Book Company (1978), each of which is incorporated by reference in its entirety.

A "nucleic acid" is a deoxyribonucleotide or ribonucleotide polymer in either single- or double-stranded form.

A "polynucleotide" refers to a single- or double-stranded polymer of deoxyribonucleotide or ribonucleotide bases.

As used herein, the terms "protein", "peptide" and "polypeptide" are used interchangeably and refer to a polymer of amino acid residues. For a general review, see, Spatola, A. F.. in CHEMISTRY AND BIOCHEMISTRY OF AMINO ACIDS, PEPTIDES AND PROTEINS, B. Weinstein, eds., Marcel Dekker, New York, p. 267 (1983), which is incorporated by reference in its entirety. As used herein, the twenty conventional amino acids and their abbreviations follow conventional usage (*Immunology—A Synthesis*. 2nd ed., (E. S. Golub and D. R. Gren, Eds.) Sinauer Associates, Sunderland, Mass. (1991)). In the polypeptide notation used herein, the lefthand direction is the amino terminal direction and the righthand direction is the carboxy-terminal direction, in accordance with standard usage and convention.

A "carbohydrate" refers to aldehyde or ketone derivatives of polyhydric alcohols. The term includes monosaccharides, oligosaccharides and polysaccharides. "Oligosaccharides" and "polysaccharides" are formed by condensation of monosaccharide residues. Oligosaccharides contain a relatively limited number of monosaccharide residues, and typically include di-, tri-, tetra- and pentasaccharides. Polysaccharides are polymers of high molecular weight formed from the condensation of many monosaccharides of the same type (homopolysaccharides) or two or more types (heteropolysaccharides). The molecular-weight of polysaccharides can range into the millions of daltons. Specific examples of carbohydrates include glucose, galactose, xylose, fructose, sucrose, and glycogen. The term "simple sugar" typically refers to monosaccharides.

The term "lipid" generally refers to substances that are extractable from animal or plant cells by nonpolar solvents. Materials falling within this category include the fatty acids, fats such as the mono-, di- and triacyl glycerides, phosphoglycerides, sphingolipids, waxes, terpenes and steroids. Lipids can also be combined with other classes of molecules to yield lipoproteins, lipoamino acids, lipopolysaccharides and proteolipids.

"Fatty acids" generally refer to long chain hydrocarbons (e.g., 6 to 28 carbon atoms) terminated at one end by a carboxylic acid group, although the hydrocarbon chain can be as short as a few carbons long (e.g., acetic acid, propionic acid, n-butyric acid). Most typically, the hydrocarbon chain is acyclic, unbranched and contains an even number of carbon atoms, although some naturally occurring fatty acids have an odd number of carbon atoms. Specific examples of fatty acids include caprioic, lauric, myristic, palmitic, stearic and arachidic acids. The hydrocarbon chain can be either saturated or unsaturated.

"Fats" are a particular class of lipids and are esters of fatty acids and glycerol. Fats include mono-, di- and tri-acylglycerides.

A "nucleoside" is a compound of a sugar (typically a ribose or deoxyribose) attached to a purine or pyrimidine base via an N-glycosyl linkage.

A "nucleotide" refers to a phosphate ester of pentose sugars in which a nitrogenous base (typically a purine or pyrimidine base) is linked to the C(1') sugar residue. Most typically, a nucleotide is a nucleoside attached to a phosphoric group.

The term "steroid" refers to the large class of compounds that contain the tetracyclic cyclopenta[α]phenanthrene backbone that are part of the metabolism of an organism. A specific example is cholesterol.

The term "compound" or "component" refers to a molecule regardless of molecular weight found within an organism or cell. A compound or component can be from the same class of compounds as a substrate or metabolite.

An "organic acid" refers to any organic molecule having one or more carboxylic acid groups. The organic acid can be of varying length and can be saturated or unsaturated. Examples of organic acids include, but are not limited to, citric acid, pyruvic acid, succinic acid, malic acid, maleic acid, oxalacetic acid, and α-ketoglutaric acid. Organic acids can include other function groups in addition to the carboxylic acid group including, for example, hydroxyl, carbonyl and phosphate.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by humans in the laboratory is naturally occurring. Generally, the term naturally occurring refers to an object as present in a non-pathological (undiseased) individual, such as would be typical for the species.

As used herein, "substantially pure" means an object species is the predominant species present (i.e., on a molar basis it is more abundant than other species in the composition, with the exception of solvent species and metal ions), and preferably a substantially purified fraction is a composition wherein the object species comprises at least about 50 percent (on a molar basis) of all species present. Generally, a substantially pure composition will comprise more than about 80 to 90 percent of all species present in the composition. Most preferably, the object species is purified to essential homogeneity (contaminant species cannot be detected in the composition by conventional detection methods) wherein the composition consists essentially of a single species.

As used herein "normal blood" or "normal human blood" refers to blood from a healthy human individual who does not have an active neoplastic disease or other disorder of lymphocytic proliferation, or an identified predisposition for developing a neoplastic disease. Similarly, "normal cells", "normal cellular sample", "normal tissue", and "normal lymph node" refers to the respective sample obtained from a healthy human individual who does not have an active neoplastic disease or other lymphoproliferative disorder.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 nM NaCl or KCl, pH 6.5-8.5, 20-45 C and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or nonionic detergents and/or membrane fractions and/or anti-foam agents and/or scintillants.

The term "statistical correlation" refers to a statistical association between two variables or parameters as measured by any statistical test including, for example, chi-squared analysis, ANOVA or multivariate analysis. The correlation between one parameter (e.g., value for the flux of a metabolite) and a second parameter (e.g., disease state) is considered statistically significant if the probability of the result happening by chance (the P-value) is less than some predetermined level (e.g., 0.05). The term "statistically significant difference" refers to a statistical confidence level, P, that is <0.25, preferably <0.05, and most preferably <0.01.

II. Overview

The present invention provides methods and apparatus for conducting metabolic analyses, including methods for purifying metabolites of interest, screens to identify metabolites that are correlated with certain diseases and diagnostic screens for identifying individuals having, or being susceptible to, a disease.

Certain methods of the invention provide electrophoretic methods for separating various metabolites using a plurality of electrophoretic methods performed in series. Such separation methods can be utilized to conduct various metabolic analyses. For example, certain analytical methods of the invention involve administering a substrate labeled with a stable isotope to a subject. The isotopic composition or enrichment of the substrate prior to administration is known. After waiting a period of time to permit the substrate to be utilized, a sample is withdrawn from the subject and used to determine the isotopic composition of multiple target analytes, the target analytes comprising the substrate and/or one or more target metabolites formed from the substrate. Typically, samples are obtained from the subject at different time points and the abundance of the isotope determined for the target analytes in each sample. In this way, the isotopic composition of the substrates can be measured as a function of time to allow a flux value for each of the target analytes to be determined. Various methods can be utilized to determine relative isotopic abundance of the isotope in the target analytes, including nuclear magnetic resonance spectroscopy, infrared spectroscopy and mass spectroscopy.

Unlike certain other methods that focus on the concentration of a particular metabolite, certain methods of the invention are designed to determine flux rather than a single concentration value. This simplifies the methods because flux values can be determined from the relative abundance of the isotope label in the target analytes rather than having to determine absolute concentration values. Furthermore, flux determinations provide insight into certain biological processes that are not observable from simple concentration determinations. For example, while concentration values may appear constant, flux can actually be changing. The concentration of any metabolite is determined by the rates of all reactions involving the formation conversion and transport of that metabolite. Therefore, increases in any two specific reactions (fluxes) involving both the formation and removal (conversion or transport) of the metabolite can yield the same apparent concentration of the metabolite Flux can be altered in response to a number of different stimuli, and thus can serve as sensitive indicator of certain cellular states. For example, flux can be altered in response to factors such as physiological state exposure to toxins and environmental insults, as well as various disease states such as infection, cancer, inflammation and genetic based defects in metabolism. Thus, flux can be used to detect diverse cellular conditions or states that are not necessarily detectable by other methods.

In some methods of the invention, the samples obtained from the subject are purified prior to determining the isotopic abundance of the isotope in the analytes. The purification procedure is used to at least partially remove other components in the cell from the target analytes of interest. Typically, this is accomplished by separating components within the sample by multiple electrophoretic methods (i.e., multiple dimensions) performed in series.

Certain methods combine the electrophoretic separation aspects of the invention with certain mass spectroscopy techniques of the invention. Such arrangements enable relatively complex samples to be sufficiently reduced in complexity so that samples containing a relatively limited number of target analytes can be directly injected into the mass spectrometer to determine the isotopic abundance in the various target analytes of interest. Such systems can be automated to permit high throughput analysis of metabolic samples.

The flux values determined for the various target analytes can be used in a variety of different applications. For example, flux values for various subjects or various physiological conditions (e.g., diseased or normal) can be used directly as inputs into a database. The flux values can also be employed in various screening applications. For example, the flux values from a test subject can be compared with corresponding flux values for a diseased subject to identify potential markers for the disease (i.e., metabolites that appear to be correlated with the disease. Groups of flux values can be used to develop a "fingerprint" for different cellular states. Once a correlation between a disease state and one or more metabolites have been made, flux values for test subjects can be compared with flux values for individuals having different diseases. Lack of a statistically significant difference between the test and diseased subjects indicates that the test subject has the disease or is susceptible to the disease. Changes in metabolic flux can be manifested as a change in the relative amounts of alternative analytes produced from a single substrate at metabolic branch points, and as the rates at which analytes resulting from serial conversions of a single substrate are produced.

III. Methods

A. General

By feeding a tissue, population of cells or an organism an isotopically-enriched substrate and following the ratio of isotopic to nonisotopic metabolites in the cell over time, one can generate a quantitative picture of cellular metabolism. The relative metabolic flux can be ascertained by determining the ratio of the amount of isotopically enriched analytes to normal analytes at any given time using a variety of different detectors capable of detecting the relative abundance of different isotopes (e.g., mass spectrometry). At each metabolic branch point, the relative ratio of isotopic to nonisotopic products on each side of the branch point provides an indication of the flux of metabolite diverted into each branch of the metabolic pathway. Following the rate of change of the isotopic ratio in identifiable metabolites along a linear metabolic pathway in pulse labeled cultures provides an estimate of the metabolic flux through each step of the pathway. Metabolites become isotopically enriched in front of slow kinetic steps and remain isotopically poor immediately after these steps. Once specific changes in cellular metabolism, such as induced by toxic challenge or infection, are identified using the techniques described herein, one can synthesize isotopically enriched compounds that can be used as specific diagnostic markers of these metabolic changes, wherein the substrate is only metabolized or fails to be metabolized in response to a specific disease state (see e.g., U.S. Pat. Nos. 4,830,010; 5,542,419; 6,010,846 and 5,924,995).

B. Administering Labeled Substrate to Subject

1. Types of Subject

A "subject" as used herein generally refers to any living organism from which a sample is taken to conduct a metabolic analysis. Subjects include, but are not limited to, microorganisms (e.g., viruses, bacteria yeast, molds and fungi), animals (e.g., cows, pigs, horses, sheep, dogs and cats), hominoids (e.g., humans, chimpanzees, and monkeys) and plants. The term includes transgenic and cloned species. The term also includes cell or tissue cultures that can be cultured to carry on the metabolic process under investigation. The term "patient" refers to both human and veterinary subjects.

If the subject is a population of cells or a cell culture, any of the standard cell culture systems known in the art can be used. Examples of suitable cell types include, but are not limited to, mammalian cells (e.g., CHO, COS, MDCK, HeLa, HepG2 and BaF3 cells), bacterial cells (e.g., *E. coli*), and insect cells (e.g., Sf9). Further guidance regarding cell cultures is provided in Sambrook et al. MOLECULAR CLONING: A LABORATORY MANUAL, 2d ed. (1989) Cold Spring Harbor Laboratory Press, Cold Spring Harbor, N.Y.

2. Types of Substrate

As used herein, the term "substrate" when used within the context of the chemical species being administered to a subject refers to any species capable of being metabolized by the subject of interest. Exemplary substrates include, but are not limited to, proteins, carbohydrates, amino acids, nucleotides, nucleosides, nucleic acids, fats, fatty acids, and steroids. A "metabolite" refers to a product derived from enzymatic conversion of a substrate administered to a subject, the conversion occurring as part of a metabolic process of the subject. A "target metabolite" is a metabolite under study in an analysis (e.g., a metabolite for which a flux value is to be determined).

A substrate labeled with a stable isotope refers to a substrate having a distribution of stable isotopes significantly different from that found in the corresponding naturally occurring substrate. The term stable isotope refers to isotopes of an element that are not radioactive. The isotopes typically used in the methods of the invention include $^{13}C$, $^{2}H$, $^{15}N$, $^{18}O$, and $^{34}S$. Hence, when substrates are labeled with $^{13}C$, the substrate includes a mixture of carbon isotopes where the $^{13}C$ isotope is incorporated in the substrate at an abundance level detectably greater than its natural abundance. For $^{13}C$ detection by mass spectrometry, this level is 2-100%, and preferably 10-100% of all the C atoms present in the substrate (i.e., the atoms in the substrate collectively have the indicated percentage enrichment). For substrates labeled with $^{15}N$, a detectable level is 0.75-100% $^{15}N$, and preferably 4-100% $^{15}N$. For substrates labeled with $^{18}O$, a detectable level is 0.4-100% $^{18}O$, and preferably 2-100% $^{18}O$. For compounds labeled with $^{34}S$, a detectable level is 8.4-100% $^{34}S$ and preferably 42-100% $^{34}S$. In some instances, the desired abundance level is obtained by mixing substrates that are isotopically enriched with non-enriched substrate.

3. Amount of Substrate

The amount of substrate added varies depending upon several factors. In general, however, the substrate is added at a safe and effective amount. As used herein, the term "safe and effective amount" means that the amount of substrate is sufficient so that the isotopic abundance, or at least a ratio of isotopic abundances, can be determined with the detector of choice, but not so high so that the substrate causes undue adverse side effects. Thus, the amount administered should be commensurate with a reasonable risk/benefit ratio. For example, if the substrate is labeled with $^{13}C$, then the substrate is administered to the patient in sufficient quantity such that the $^{13}C/^{12}C$ ratio in the target analyte(s) can be determined. However, the amount of substrate administered is below the amount that causes undesired side effects (e.g., toxicity, irritation or allergic response). The safe and effective amount depends upon factors such as the nature and amount of the sample acquired (e.g., gas or liquid and/or acquisition site), the weight of the test subject, and the relative concentration of the isotope in the substrate.

4. Mode of Administration

Typically a mixture of known amounts of both labeled and unlabeled substrate is administered to a subject. The mixture may contain between 5-95% relative abundance of labeled substrate. More preferably, the mixture contains between 25-75% labeled substrate. Most preferably, the mixture contains about equimolar ratios of labeled and unlabeled substrate.

In certain methods, the substrate is administered to the subject as a pulse. Pulsed additions or pulsed labeling refers to the timed addition of an isotopically labeled substrate, wherein the relative isotopic abundance of the isotopes is known. Long pulses can be used to estimate net synthesis rates of particular biomolecules starting from the time of the pulse. In this instance, previous biomass contains no label, but new biomass begins to accumulate the isotope in proportion to the isotopic abundance of the label in the substrate. If the pulse duration is long compared to the turnover of the substrate and target analytes of interest, the net synthesis rate is measured. Short pulses (significantly shorter than the turnover rate) do not account for degradation and recycle, so provide an estimate of the unidirectional synthesis rate.

The mode by which the substrate is administered to the subject can vary but should be administered in such a way that the substrate can be metabolized within a reasonable time frame. The substrate can be administered in substantially pure form or as part of a composition. Compositions can include pharmaceutically acceptable components including, but not limited to, diluents, emulsifiers, binders, lubricants, colorants, flavors and sweeteners, so long as these components do not interfere with the metabolism of the substrate being administered. Guidance on the incorporation of such optional components is discussed, for example, in *The Theory and Practice of Industrial Pharmacy* (L. Lachman, et al., Ed.) 1976; and *Remington's Pharmaceutical Sciences*, Mace Publishing Company, Philadelphia, Pa., 17th ed., (1985); and Langer, *Science* 249:1527-1533 (1990), each of which is incorporated by reference in its entirety.

In some instances, the substrate is administered orally in solid form (e.g., solid tablet, capsule, powder, pill granule) or as part of a liquid solution (e.g., emulsion, suspension). When shaping into the form of tablets, as the carrier for the substrate, there can be used excipients such as lactose, sucrose, sodium chloride, glucose, urea, starch, calcium carbonate, kaolin, crystalline cellulose, silicic acid, and potassium phosphate; binders such as water, ethanol, propanol, simple syrup, glucose solution, starch solution, gelatin solution, carboxymethyl cellulose, hydroxypropyl cellulose, methyl cellulose, and polyvinyl pyrrolidone; disintegrators such as carboxymethyl cellulose sodium, carboxymethyl cellulose calcium, low-substitution degree hydroxypropyl cellulose, dried starch, sodium alginate, agar powder, laminaran powder, sodium bicarbonate, and calcium carbonate; surfactants such as polyoxyethylene sorbitan fatty acid ester, sodium lauryl sulfate, and monoglyceride stearate; disintegration inhibitors such as sucrose, stearin, cacao butter, and hydrogenated oil; absorption accelerators such as quaternary ammonium base, and sodium lauryl sulfate; humectants such as glycerin and starch; absorbents such as starch, lactose, kaolin, bentonite, and colloidal silicic acid; and lubricants such as purified talc, stearate, borax and polyethylene glycol. Furthermore, tablets can be optionally formed into tablets subjected to normal tablet coating, such as sugar coated tablets, gelatin coated tablets, enteric coated tablets, film coated tablets or double tablets and multilayer tablets.

When shaping into the form of pills, as the carrier for the substrate, there can be used excipients such as glucose, lactose, starch, cacao butter, hardened vegetable oil, kaolin, and talc; binders such as gum arabic, tragacanth powder, gelatin, and ethanol; and disintegrators such as laminarane and agar.

The substrate, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides, paraffin hydrocarbons, polyethylene glycol, cacao butter, higher alcohols, esters of higher alcohols, gelatin, and semisynthetic glycerides. In addition, it is also possible to use gelatin rectal capsules that consist of a combination of the substrate with a base, including, for example, liquid triglycerides, polyethylene glycols, and paraffin hydrocarbons.

Formulations of the substrate suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The compositions are formulated as sterile, substantially isotonic and in full compliance with all Good Manufacturing Practice (GMP) regulations of the U.S. Food and Drug Administration.

When the substrate is administered to a population of cells, the cells are typically suspended in a matrix containing the isotopically-enriched substrate, The matrix is typically an aqueous solution and can also contain other nutrients. Depending upon the number of cells, the cells can be suspended in standard culture flasks or within the wells of a microtiter plate, for example.

C. Sample Collection

1. Sample Sources and Types

As noted above, the methods of the invention can be used to analyze metabolism in essentially any living organism. The samples can come from tissues or tissue homogenates, fluids of an organism or cells or cell cultures. Generally, samples are obtained from the body fluid of an organism. Such fluids include, but are not limited to, whole blood, plasma, serum, semen, saliva, urine, sweat, spinal fluid, saliva, gastrointestinal fluids, sweat, cerebral fluid, and lacrimal fluids. In some instances, samples are obtained from fecal material, buccal, skin, tissue biopsy or necropsy and hair. Samples can also be derived from ex vivo cell cultures, including the growth medium, recombinant cells and cell components. In comparative studies to identify potential drug or drug targets (see infra), one sample can be obtained from a diseased subject or cells and another sample a non-diseased subject or from non-diseased cells, for example.

2. Collection Options

Certain methods involve withdrawing a sample of blood from the subject. If whole blood is used, the sample typically is lysed by any of the methods known to those of skill in the art including, for example, freezing/thawing the sample. Urine can be collected by collecting the urine of the subject in a clean container. In some instances, a sample is obtained from the breath of an individual (e.g., when the target metabolite is carbon dioxide). A variety of different devices and methods have been developed to collect breath samples. For example, the breath of a subject can be captured by having the subject inflate an expandable collection bag (e.g., a balloon). The sample can then be transferred to a commercially available storage container for subsequent storage and/or transport (e.g., the VACUTAINER manufactured by Becton-Dickenson Company). Other breath collection devices are described in U.S. Pat. Nos. 5,924,995 and 5,140,993, which are incorporated by reference in their entirety. Tissue samples may be obtained by biopsy.

In the case of cell or tissue cultures, cells are collected by centrifugation or filtration and then lysed according to standard protocols (e.g., sonication, blending, pressurization, freeze thawing and denaturation). Alternatively, cells can be collected and lysed by the addition of trichloroacetic acid (to a final concentration of 5-10% weight to volume), or similar use of other membrane lytic solvents (e.g., chloroform, diethyl ether, toluene, acetone, and ethanol). Such membrane lytic solvents can be used to precipitate macromolecular components and selectively solubilize small molecule metabolites as a precursor to subsequent electrophoretic separation techniques.

D. Target Analyte Separation

1. Preliminary Purification

Depending on the complexity of the sample (i.e., the number and different types of components within the sample), the target analytes (i.e., substrate and/or target metabolites) are first at least partially purified from other components within the sample. If the sample contains cellular debris or other material that might interfere with separation, such materials can be removed using any of a variety of known separation techniques including, for example, forcibly extruding the sample through sieve material, filtration, centrifugation (e.g., density gradient centrifugation), and various chromatographic methods (e.g., gel filtration, ion exchange or affinity chromatography).

Many macromolecules (e.g., proteins and nucleic acids) can be separated from small molecules (e.g., nucleotides, acetyl CoA, mono- and disaccharides, amino acids) by lysing the cells and quantitatively precipitating the macromolecules by treating the lysed cells with cold trichloroacetic acid (e.g. 5-10% TCA weight to volume for 30 min on ice), while most of the small molecules in the cell remain soluble. Additional separation methods are discussed, for example, by Hanson and Phillips (Hanson, R. S. and Phillips, J. A., In: *Manual of methods for general bacteriology*, Gerhardt et al. (eds.)., Am. Soc. Microbiol., Washington, D.C., p. 328 (1981)).

2. Multidimensional Electrophoresis

Once such initial purification steps have been completed (if necessary), the target analytes are typically further purified by conducting a plurality of electrophoretic methods conducted in series. For optimal performance, samples whose ionic strength is particularly high can be desalted using established techniques such as dialysis and dilution and reconcentration prior to conducting the electrophoretic methods. The methods are said to be conducted in series because the sample(s) electrophoresed in each method are from solutions or fractions containing components electrophoresed in the preceding method, with the exception of the sample electrophoresed in the initial electrophoretic method. Each of the different electrophoretic methods is considered a "dimension", hence the series constitutes an "multidimensional" separation.

The series of electrophoretic methods are typically conducted in such a way that components in an injected sample for each electrophoretic method of the series are isolated or resolved physically, temporally or spacially to form a plurality of fractions, each of which include only a subset of components contained in the sample. Thus, a fraction refers to a solution containing a component or mixture of components that are resolved physically, temporally or spacially from other components in a sample subjected to electrophoresis. Hence, resolved components can refer to a single component or a mixture of components that are separated from other components during an electrophoretic method. As just noted, samples in the various electrophoretic methods are obtained from such fractions, with the exception of the first electrophoretic method in which the sample is the original sample containing all the components to be separated.

Typically, these multiple electrophoretic methods in the series separate components according to different characteristics. For example, one method can separate components on the basis of isoelectric points (e.g., capillary isoelectric focusing electrophoresis), other methods can separate components on the basis of their intrinsic or induced (through the application of a label to certain ionizable groups) charge-to-mass ratio at any given pH (e.g., capillary zone electrophoresis), whereas other methods separate according to the size of the components (e.g., capillary gel electrophoresis).

Figure 2A:
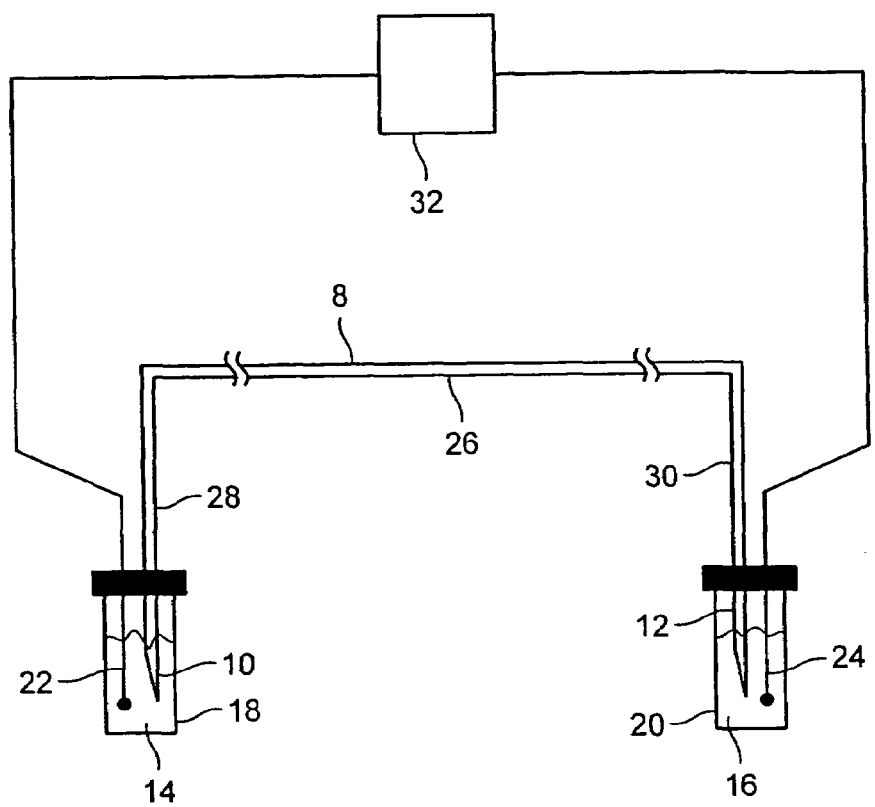
FIG. 2A is a schematic representation of some of the major elements of an electrophoretic system utilized in conducting certain electrophoretic methods of the invention.

Apparatus used to conduct various electrophoretic methods are known in the art. In general, however, and as shown in FIG. 2A, the basic configuration of a typical capillary electrophoretic system utilized in certain methods of the invention includes a capillary 8 having two ends 10, 12. One end 10 is in contact with an anode solution or anolyte 14 contained in an anode reservoir 18 and the other end 12 is in contact with a cathode solution or catholyte 16 in a cathode reservoir 20. One electrode (the anode) 22 is positioned to be in electrical communication with the anode solution 14 and a second electrode 24 is positioned to be in electrical communication with the cathode solution 16. The cavity 26 of the capillary 8 is filled with an electrophoretic medium, which in some instances can include a polymer matrix. As used herein the term anode refers to the positively charged electrode. Thus, negatively charged species move through the electrophoretic medium toward the anode. The term cathode refers to the negatively charged electrode; positively charged species migrate toward this electrode. The anolyte is the solution in which the anode is immersed and the catholyte is the solution in which the cathode is immersed.

Sample is introduced into the capillary 8 via an inlet 28, and the components therein resolved as an electrical field is applied between the two electrodes 22, 24 by a power source 32 and the components separate within the electrophoretic medium contained within the separation cavity 26. Components can be controllably eluted from the capillary via outlet 30 by controlling various parameters such as electroosmotic flow (see infra) and/or by changing the composition of one or both of the reservoir solutions (e.g., adjusting the pH or salt concentration). Typically, the inlet 28 and the outlet 30 are simply portions of the capillary formed to allow facile insertion into a container containing sample, anolyte or catholyte.

The term "capillary" as used in reference to the electrophoretic device in which electrophoresis is carried out in the methods of the invention is used for the sake of convenience. The term should not be construed to limit the particular shape of the cavity or device in which electrophoresis is conducted. In particular, the cavity need not be cylindrical in shape. The term "capillary" as used herein with regard to any electrophoretic method includes other shapes wherein the internal dimensions between at least one set of opposing faces are approximately 2 to 1000 microns, and more typically 25 to 250 microns. An example of a non-tubular arrangement that can be used in certain methods of the invention is the a Hele-Shaw flow cell (see, e.g., U.S. Pat. No. 5,133,844; and Gupta, N. R. et al., *J. Colloid Interface Sci.* 222:107-116 (2000). Further, the capillary, need not be linear; in some instances, the capillary is wound into a spiral configuration, for example.

An example of a system utilized with certain methods of the invention is illustrated in FIG. 1. This particular example shows a system in which three electrophoresis methods (initial, intermediate and final methods) are linked. The particular number of electrophoretic methods conducted can vary, although the methods of the invention generally include at least two electrophoretic methods. Most typically, the methods utilize two or three electrophoretic separation methods.

As can be seen in FIG. 1, an initial sample containing a plurality of components is introduced from sample container 50 into a first separation cavity of a first capillary 54 via sample inlet 52 utilizing any of a number of methods known in the art. Examples of suitable methods include, pulling sample into the sample inlet 52 under vacuum (e.g., by pulling a vacuum on the sample outlet) or pushing sample into the sample inlet 52 by pressurizing the sample container 50. Electromigration, often referred to as electrokinetic injection, is another option. Once the initial sample is introduced into sample inlet 52, the sample is then electrophoresed within the first separation cavity within the first capillary 54. The first separation cavity contains a desired electrophoretic medium in which components in the initial sample are at least partially resolved. Electrophoretic medium containing resolved components is withdrawn from the first cavity, typically out the end of the separation cavity opposite the end in which sample was introduced, although other withdrawal sites can be utilized (see infra). The withdrawn medium travels through outlet 56 and is collected in separate containers 58 as multiple fractions. As shown in FIG. 1B, the containers 58 into which fractions are collected are typically associated with a fraction collection device (a portion of which is shown 60) capable of automatically advancing a set of containers 58 to collect defined fractions (e.g., fractions of a certain volume or covering a selected pH range).

A sample from a fraction collected from the first electrophoretic method is then withdrawn from one of the plurality of containers 58, again utilizing techniques such as those described supra, via a second sample inlet 62. Components in the sample from the fraction can then be further resolved by conducting an intermediate electrophoretic method (in the example shown in FIG. 1, the second electrophoretic method). The sample is introduced into a second capillary 64 via inlet 62 and the components within the sample further separated within the electrophoretic medium contained within the second separation cavity of the second capillary 64 and then eluted from the cavity via outlet 66. As with the first electrophoretic separation the electrophoretic medium containing the resolved or partially resolved components is collected as separate fractions within containers 68 typically aligned and advanced by a second fraction collection device (a portion of which is shown 70).

A process similar to the second/intermediate method is conducted during the final electrophoretic method (the third electrophoretic separation method shown in FIG. 1). Sample is drawn via inlet 72 from a container 68 containing a fraction obtained during the preceding method and is introduced into a third or final electrophoretic cavity of a third capillary 74 containing a third electrophoretic medium in which components contained in the applied sample are further separated by electrophoresis. The third electrophoretic medium containing the further isolated proteins is subsequently withdrawn through outlet 76.

As noted above, more than the three electrophoretic methods shown in FIG. 1 can be performed. Such methods essentially involve repeating the general steps described for the second/intermediate electrophoretic separation above one or more times.

Following the final electrophoretic separation, a variety of different options for analyzing the resolved components are available. As shown in FIG. 1, withdrawn electrophoretic medium can be passed through an optional detector 78 in fluid communication with the separation cavity of the last capillary 74 to detect the resolved components (e.g., labeled proteins). The detector 78, or an optional quantifying device capable of receiving a signal from the detector (not shown), can be used to quantitate the amount of components within a certain portion or fraction of the electrophoretic medium. Detectors can also be utilized to monitor the progress of separation after other columns as well.

Fractions are taken from the electrophoretic medium exiting the final capillary 74 or the detector 78 and analyzed by an analyzer 82 to determine the molecular weight of the components within a fraction. In particular, the analyzer is used to determine the abundance of the enriched isotope in the target analytes. As described infra, a variety of analyzers and techniques can be utilized to make this determination. For example, the analyzer 82 can be a mass spectrometer or an infrared spectrometer. Mass spectral data, for example, can be utilized to determine the mass of the various components within a fraction. The ratio of labeled and unlabeled target analytes can be determined from the relative signal intensities for the labeled and unlabeled target analytes in the mass spectrum.

The specific elution conditions utilized to withdraw resolved components from the separation cavity depends upon the type of electrophoretic method conducted and is described more fully below for each of the electrophoretic methods typically utilized in the present invention in general, however, once components have been resolved within the separation cavity, the conditions within the cavity are adjusted as necessary (or the initial conditions selected) to achieve selective or controlled elution of the components from the cavity. For example, elution can be achieved by adding salts to, or adjusting the pH of, the anode or cathode solution, by regulating electroosmotic flow, by applying hydrodynamic pressure or combinations of the foregoing.

Using the methods of the invention, resolved components can be isolated physically (e.g., placement into different containers such as illustrated in FIG. 1), spatially (e.g., spread throughout the electrophoretic medium contained in the separation cavity) and/or temporally (e.g., controlling elution so different components within a sample elute from the capillary at different times). Thus, the methods of the invention can separate mixtures of components as a function of the composition of elution buffers and/or time. The methods are not limited to the spatial separation of components as are certain traditional gel electrophoresis systems (e.g., 2-D gel electrophoresis systems for protein separation or pulsed-field and sequencing gel systems for nucleic acid separations), or two-dimensional thin layer chromatography (2-D TLC) methods (for small molecule metabolite separations). Instead, with controlled elution, fractions can be collected so components within a fraction fall within a range of isoelectric points and electrophoretic mobilities, for example. Controlled elution of components means that methods can be performed in a reproducible fashion. Such reproducibility is important in conducting comparative studies and in diagnostic applications, for example.

During the elution or withdrawing of resolved components, generally only a portion of the electrophoretic medium containing the resolved component is typically collected in any given fraction. This contrasts with certain 2-D methods in which a gel containing all the resolved components (e g., proteins) is extruded from the separation cavity and the extruded gel containing all the components is used to conduct another electrophoretic separation. This also contrasts with certain 2-D thin layer chromatography methods in which all the metabolites are separated by their relative affinities for the matrix in a line using one solvent system and are reseparated based on altered affinities by a second solvent system applied perpendicularly to the direction of flow of the first solvent system.

Spacially, physically or temporally resolved components obtained at the conclusion of one electrophoretic method are then used as the source of samples for further separation of components contained within the fraction during a subsequent electrophoretic method. As illustrated in FIG. 1 typically samples from different resolved fractions are sequentially electrophoresed on the same capillary. Normally another sample is not applied until the components in the preceding sample are sufficiently withdrawn from the separation cavity so that there is no overlap of components contained in different fractions. Sequential elution of fractions through the same column can significantly reduce or eliminate variations resulting from differences in cross-linking or electric field strength that can be problematic in certain slab gel electrophoretic methods. Hence, sequential separation can further enhance the reproducibility of the methods of the invention. Other methods, however, can be performed in a parallel format, wherein samples from different fractions are electrophoresed on separate capillaries. This approach allows for separations to be completed more quickly. However, the use of multiple capillaries can increase the variability in separation conditions, thereby reducing to some extent reproducibility between different samples.

In certain methods, the electrophoretic methods are conducted so that pools containing similar components are obtained. For example, the electrophoretic conditions can be controlled so that after the first or first few electrophoretic methods at least one pool containing primarily related components is obtained (e.g., a pool containing primarily proteins, polysaccharides, nucleic acids, amino acids, nucleotides, nucleosides, oligosaccharides, phosphorylated mono- or oligosaccharides, fats, fatty acids or organic acids). Pools of related components can be obtained by capitalizing on the distinctive feature of the different classes of components within a cell. For example, some classes of components are primarily singly charged (e.g., phosphorylated mono- or oligosaccharides), whereas others are primarily zwitterionic (e.g., amino acids, proteins, nucleotides and some fats). CIEF can be used to resolve different zwitterionic components and can also be used to separate zwitterionic species from non-zwitterionic species. Large components (e.g., proteins) can be separated from smaller components (e.g., amino acids, mono- and disaccharides, nucleotides and nucleosides) using CGE. Through judicious selection of pH and buffer conditions, one can control the charge on various components and effect separation of components having different charge-to-mass ratios by CZE. For example, certain buffers can be utilized that selectively complex with certain components to introduce a desired charge to the selected components. An example of such a buffer is a borate buffer that can be used to complex to carbohydrates thereby imparting a negative charge to the carbohydrates present in the sample. Additional details regarding the electrophoretic methods are set forth infra.

By controlling the electrophoretic conditions to initially separate a complex mixture into pools of different classes of components, one can simplify an analysis considerably. For example, if the metabolite of interest is a carbohydrate, by controlling conditions appropriately so that a pool of carbohydrates is obtained (e.g., using borate buffers), one can ignore fractions containing other classes of compounds. Thus, subsequent electrophoretic separations can simply be conducted with a sample from the pool(s) of interest. Alternatively, if the pool of similar compounds is sufficiently small, individual components of the pool can be completely resolved by mass spectrometric means after the electrophoretic separations. Similarly, once conditions have been established for a particular metabolite, it is not necessary to analyze all fractions obtained from the various electrophoretic methods. The reproducibility of the method enables a sample to be taken only from the few fractions obtained adjacent the fraction(s) previously established to contain the target analytes of interest. Nonetheless, because certain methods can be automated, even during initial screening tests, for example, one can quickly analyze all the final fractions. Even scanning the mass spectrum to identify signals for mass fragments of interest can be automated through the use of computer programs to speed analysis.

E. Detection

Once the target analytes have been at least partially purified from other molecules in the sample, the relative abundance of the isotope in the unmetabolized substrate and/or target analytes is determined. Typically, this involves determining the ratio of the enriched isotope to the more abundant isotope (e.g., $^{12}C/^{13}C$, $^{14}N/^{15}N$, $^{16}O/^{18}O$ and $^{34}S/^{32}S$), although other measures of abundance can also be determined.

The measurement of the concentration of the enriched stable isotope can be made according to a variety of options. One approach is to determine the relative abundance of the isotopic label by mass spectrometry. The target analytes generate distinct signals in the mass spectrum according to the mass to charge ratio of the substrate. The relative signal intensities for the different isotopic forms present enables the relative abundance of the different isotopic forms of each target analyte to be calculated, regardless of the absolute concentration of the analyte in the sample.

Methods for analyzing various biological molecules by mass spectrometry have been established. Mass spectrometry can be used according to known methods to determine the masses of relatively small molecules (e.g., nucleosides, nucleotides, mono and di-saccharides) as well as relatively large molecules. For example, mass spectrometry has increasingly been applied to protein identification. Electrospray and matrix assisted laser desorption ionization (MALDI) are the most commonly used mass spectrometric techniques applied to protein analysis because they are best able to ionize large, low volatility molecular species.

In the case of DNA, the DNA can by hydrolyzed to deoxyribonucleosides using standard methods of hydrolysis. For example, the DNA can be hydrolyzed enzymatically, such as for example with nucleases or phosphatases, or non-enzymatically with acids, bases or other methods of chemical hydrolysis. Alternatively, intact DNA polymers can be analyzed. Deoxyribonucleosides can then be prepared for mass spectroscopic analysis using standard techniques (e.g., synthesis of trimethylsilyl, methyl, acetyl and related derivatives or direct probe injection).

For the following major classes of metabolites, the following sources provide additional guidance on mass spectral analysis of such molecules and are incorporated by reference in their entirety: (1) lipids (see, e.g., Fenselau, C., "Mass Spectrometry for Characterization of Microorganisms", *ACS Symp. Ser.*, 541:1-7 (1994)); (2) volatile metabolite (see, e.g., Lauritsen, F. R. and Lloyd, D., "Direct Detection of Volatile Metabolites Produced by Microorganisms," *ACS Sympl Ser.*, 541:91-106 (1994)); (3) carbohydrates (see, e.g., Fox, A. and Black, G. E., "Identification and Detection of Carbohydrate Markers for Bacteria", *ACS Synp. Ser.* 541: 107-131 (1994); (4) nucleic acids (see, e.g., Edmonds, C. G., et al., "Ribonucleic acid modifications in microorganisms", *ACS Symp. Ser.*, 541:147-158 (1994); and (5) proteins (see, e.g., Vorm, O. et al., "Improved Resolution and Very High Sensitivity in MALDI TOF of Matrix Surfaces made by Fast Evaporation," *Anal. Chem.* 66:3281-3287 (1994); and Vorm, O. and Mann, M., "Improved Mass Accuracy in Matrix-Assisted Laser Desorption/Ionization Time-of-Flight Mass Spectrometry of Peptides", *J. Am. Soc. Mass. Spectrom.* 5:955-958 (1994)). Further details regarding mass spectral analysis is set forth infra.

Labeled carbon dioxide ($[^{13}C]CO_2$) can also be detected using mass spectrometry. Such approaches are described, for example, by Ewing, G. W., *Instrumental Methods of Chemical Analysis*, 4th ed., (1975); and Klein, P., et al., "Stable Isotopes and Mass Spectrometry in Nutrition Science", *Analytical Chemistry Symposium Series* 21:155-166 (1984), both of which are incorporated by reference in their entirety.

An alternative to detection by mass spectrometry is to detect the isotope label using infrared (IR) spectroscopy or nuclear magnetic resonance spectroscopy (NMR). Various target analytes can be detected using this approach, including carbon dioxide, for example. IR and NMR methods for conducting isotopic analyses are discussed, for example, in U.S. Pat. No. 5,317,156; Klein, P. et al., *J. Pediatric Gastroenterology and Nutrition* 4:9-19 (1985); Klein, P., et al., *Analytical Chemistry Symposium Series* 11:347-352 (1982); and Japanese Patent Publications No. 61-42219 and 5-142146, all of which are incorporated by reference in their entirety.

In certain methods, target analytes partially or completely purified by the electrophoretic methods are subsequently transported directly to an appropriate director for analyzing the isotopic composition of the target analytes. In some methods, samples are withdrawn from the individual fractions collected during the final electrophoretic separation and injected directly onto a mass spectrometer to determine relative abundances.

F. Flux Determination

In general, the flux of metabolites through each reaction step in any given pathway depends on the relative rates of the forward reaction and reverse reactions. As used herein, flux refers to the rate of change in concentration of a target analyte as a function of time and sample size. The metabolic flux through any single metabolic conversions can be determined from the change in the relative abundance ($RA_t$) of isotopically labeled analyte over time (t) according to the equation:

$$Flux_{analyte} = \frac{\ln\{1 - RA_t/RA_{ss}}{(t)(\text{unit of sample})}$$

where $RA_{SS}$ is the relative abundance of the labeled metabolite at long times. Relative abundance (RA) is the relative concentrations of isotopically labeled substrate and/or target metabolite (i.e., the target analytes) determined from the ratio of the abundances of isotopic label in the target analytes. In some embodiments, the steady-state relative abundance of the isotope can be considered equal to the known ratio in the initial substrate administered to the subject, such that a only a single sample is needed to determine the metabolic flux. In another embodiment, the steady-state relative abundance of the isotope can be predicted from simultaneous solution of the above equation for two or more relative abundance measurements taken from samples taken at different time points. In another embodiment, the steady-state relative abundance of the isotope can be measured directly from samples taken at long times.

It is apparent to those skilled in the art that an alternative form of the above equation can be used to determine the flux of an analyte from the depletion of isotopically labeled analyte or substrate following a reduction in the relative abundance of isotopically labeled substrate. This alternative form is:

$$Flux_{analyte} = \frac{\ln\left\{\frac{(RA_t - RA_{ss})}{(RA_o - RA_{ss})}\right\}}{(t)(\text{unit of sample})}$$

where $RA_O$ is the initial relative abundance of the isotopically labeled analyte prior to the administration of substrate to change the relative abundance. In one embodiment, $RA_O$ is measured directly prior to administration of the new substrate. In another embodiment, $RA_O$ is assumed to be the same as the relative isotope abundance in the substrate administered prior to the change.

The relative metabolic flux of substrate into any metabolic branch (i) in a network of n branched metabolic pathways is determined from the ratio of relative abundances of iotopically labeled analyte appearing in analytes downstream in each branch (j) of the metabolic pathway at any time (t), but preferably at long times (i.e., at the steady-state condition), according to the equation:

$$Flux_{branch}^{j} = \frac{RA_t^i}{\sum_{j=1}^{n} RA_t^j} [Flux_{substrate}]$$

To determine flux, typically one or more samples are withdrawn from the subject at different predetermined time points. The samples are then treated, optionally purified, and then analyzed as described above to determine one or more values for the relative concentration of the isotopic label in the target analytes at a sampling time(s) (t). These values can then be utilized in the formula set forth above to determine a flux rate for each of a plurality of target analytes. In some instances, the target analytes used to determine flux are all organic compounds (i.e., the analytes do not include carbon dioxide, for example).

It is apparent to those skilled in the art that more accurate flux determinations and standard errors of the estimated fluxes can also be made using statistical curve fitting or parameter fitting methods generally known in the art (e.g., Zar, J. H. Biostatistical Analysis, (Prentice-Hall, Englewood Cliffs, N.J., 1974)) and isotopic ratio data obtained from a plurality of samples taken at different times.

The metabolic flux through a pathway depends on the rate determining step(s) within the pathway. Because these steps are slower than subsequent steps in the pathway, a product of a rate determining step is removed before it can equilibrate with reactant. Further guidance on flux and methods for its determination is provided, for example, by Newsholme, E. A. et al., *Biochem. Soc. Stamp.* 43:183-205 (1978); Newsholme, E. A., et al., *Biochem. Soc. Symp.* 41:61-110 (1976); and Newsholme, E. A., and Sart., C., *Regulation in Metabolism*, Chaps. 1 and 3, Wiley-Interscience Press (1973).

IV. Synthesis of Labeled Substrates

The synthesis of isotopically labeled biological compounds has been well established for a variety of different types of compounds including, for example, nucleic acids, proteins, carbohydrates, as well as glycolysis and other metabolic pathway intermediates. Methods for isotopically labeling nucleic acids are discussed, for example, in U.S. Pat. No. 6,010,846; the labeling of carbohydrates is discussed in U.S. Pat. No. 4,656,133; and methods for labeling glycolysis intermediates is discussed in U.S. Pat. No. 5,439,803, all of which are incorporated by reference in their entirety.

In some instances, isotopically labeled biological compounds are obtained by feeding live organisms a diet enriched in one or more stable isotopes, harvesting and purifying the desired isotopically enriched compounds resulting from natural metabolism of the isotopically-enriched diet. Alternatively, isotopically-enriched substrates can be synthesized chemically from isotopically enriched precursors. Many suitable substrates for metomics studies (e.g., $[^{13}C]$-fatty acids, $[^{2}H, ^{13}C$ and $^{15}N]$-amino acids, $[^{13}C$ and $^{2}H]$-peptides, and $[^{13}C$ and $^{15}N]$-nucleotides) are available from commercial sources such as Isotec (Miamisburg, Ohio), ICN Pharmaceuticals (Costa Mesa, Calif.), and Sigma-Aldrich (St. Louis, Mo.).

V. Capillary Electrophoresis Methods

A. Capillary Isoelectric Focusing Electrophoresis (CIEF)

1. General

Isoelectric focusing is an electrophoretic method in which zwitterionic substances such as proteins, nucleotides, amino acids and some fats are separated on the basis of their isoelectric points (pI). The pI is the pH at which a zwitterionic species such as a protein has no net charge and therefore does not move when subjected to an electric field. In the present invention, zwitterionic species can be separated within a pH gradient generated using ampholytes or other amphoteric substances within an electric field. A cathode is located at the high pH side of the gradient and an anode is located at the low pH side of the gradient.

Zwitterionic species introduced into the gradient focus within the pH gradient according to their isoelectric points and then remain there. The focused components can then be selectively eluted as described below. General methods for conducting CIEF are described, for example, by Kilar. F., "Isoelectric Focusing in Capillaries," in *CRC Handbook on Capillary Electrophoresis: A Practical Approach*, CRC Press, Inc., chapter 4, pp. 95-109 (1994); and Schwartz. H., and T. Pritchett, "Separation of Proteins and Peptides by Capillary Electrophoresis: Application to Analytical Biotechnology," Part No. 266923 (Beckman-Coulter, Fullerton, Calif., 1994); Wehr, T., Rodriquez-Diaz, R., and Zhu, M., "Capillary Electrophoresis of Proteins," (Marcel Dekker, N.Y., 1999), which are incorporated herein by reference in their entirety.

2. System and Solutions

Because CIEF is primarily an equilibrium technique with low current densities, capillary heating typically is not a problem. Therefore, fairly large bore capillaries can be utilized. Suitable sizes include, but are not limited to, capillaries having internal diameters of 2-600 μm, although more typically capillaries having internal diameters of 25-250 μm are utilized. The use of relatively large bore capillaries means the method can use relatively high sample loads, which facilitates detection in subsequent dimensions. This feature of CIEF makes the method well suited for the initial or one of the early electrophoretic separations in the series. However, smaller diameter capillaries enable temperature to be controlled more carefully and, in some methods, result in improved signal detection (e.g., by laser induced fluorescence (LIF) detection of fluorescently labeled proteins).

The capillaries can have varying lengths. The length selected depends in part on factors such as the extent of separation required. Typically, the capillaries are about 10 to 100 cm in length, although somewhat shorter and longer capillaries can be used. While longer capillaries typically result in better separations and improved resolution of complex mixtures, longer capillaries also afford more opportunities for interactions between species in the sample and the capillary wall and lower field strength. Consequently, there tends to be an upper limit on capillary length beyond which resolution may be lost. Longer capillaries can be of particular use in resolving low abundance compounds. Further guidance on size and length of capillaries is set forth, for example, in Palmieri, R. and J. A. Nolan, "Protein capillary electrophoresis: Theoretical and experimental considerations for methods development," in: *CRC Handbook of Capillary*

*Electrophoresis: A Practical Approach*, Chp. 13, pgs. 325-368 (CRC Press, Boca Raton, 1994).

Generally, the capillaries are composed of fused silica, although plastic capillaries and PYREX (i.e., amorphous glass) can be utilized in certain methods. As noted above, the capillaries do not need to have a round or tubular shape. Other shapes herein the internal dimension between opposing faces is within the general range set forth in this section can also be utilized.

A variety of different anode and cathode solutions can be used. Common solutions include sodium hydroxide as the catholyte and phosphoric acid as the anolyte. Similarly, a number of different ampholytes can be utilized to generate the pH gradient, including numerous commercially available ampholyte solutions (e.g., BioLyte, Pharmalyte and Servalyte). The selection of ampholytes and the breadth of the ampholyte gradient can impact the resolution that is achieved by CIEF methods. Narrow ampholyte gradients increase the number of theoretical plates in the separation and can be beneficial for higher resolution separations over narrow pI ranges.

CIEF methods utilized in the separations of the invention can be conducted in capillaries containing polymeric matrices or in free solution (i.e., no gel or other polymeric matrix). Polymer matrices are typically added to slow electroosmotic flow; however, in some instances, inclusion of polymeric matrices can restrict movement of larger proteins (Patton, W. F., "Defining protein targets for drug discovery using Proteomics," paper presented at the IBC Proteomics conference, Coronado, Calif. (Jun. 11-12, 1998)). The use of free solutions is preferable in such cases possibly in combination with other methods (e.g., capillary coatings, gel plugs, or induced electric fields) to control the electroosmotic flow.

3. Sample Preparation

In some instances, samples to be electrophoresed by CIEF are subjected to denaturants to denature certain macromolecules, particularly proteins. This ensures that the same components all have the same charge and thus identical components focus at the same location rather than potentially at multiple zones within the capillary. Denaturants (e.g., urea), non- and zwitterionic-surfactants (e.g., IGEPAL CA-630 or 3-[{3-cholamidopropyl}dimethylammonio]-1-propane sulfonate) can also be used to suppress protein-wall and/or protein-protein interactions that can result in protein precipitation. An advantage of denaturing the proteins within a sample prior to electrophoresis is that the results can be used in comparisons with archival data typically obtained under denaturing conditions.

A typical denaturing buffer includes urea and a nonionic or zwitterionic surfactant as denaturants; a reducing agent (e.g., dithiothreitol (DTT) or mercaptoethanol) is typically included to reduce any disulfide bonds present in the proteins. Other denaturants besides urea that can be used include, but are not limited to, thiourea and dimethylformamide (DMF). Generally, guanidine hydrochloride is not utilized as a denaturant because of the very high ionic strength it imparts to a sample. Exemplary neutral detergents include polyoxyethylene ethers ("tritons"), such as nonaethylene glycol octylcyclohexyl ether ("TRITON" X-100), polyglycol ethers, particularly polyalkylene alkyl phenyl ethers, such as nonaethylene glycol octylphenyl ether ("NONIDET" P-40 or IGEPAL CA-630), polyoxyethylene sorbitan esters, such as polyoxyethylene sorbitan monolaurate ("TWEEN"-20), polyoxyethylene ethers, such as polyoxyethylene lauryl ether ($C_{12}E_{23}$) ("BRIJ"-35), polyoxyethylene esters, such as 21 stearyl ether ($C_{18}E_{23}$) ("BRIJ"721), N,N-bis[3-gluconamido-propyl]cholamide ("BIGCHAP"), decanoyl-N-methylglucamide, glucosides such as octylglucoside, 3-[{3-cholamidopropyl}dimethylammonio]-1-propane sulfonate and the like.

The optimal amount of denaturant and detergent depends on the particular detergent used. In general the denaturing sample buffers contain up to 10 M urea (more typically 4-8 M and most typically 6-8 M). Specific examples of suitable buffers (and denaturants and nonionic surfactants for inclusion therein) include those described by Hochstrasser et al. (*Anal. Biochem.* 173:424 (1988)) and O'Farrell (*J. Biol. Chem.* 250:4007 (1975)). Denaturation is typically advanced by heating for 10 min at 95° C. prior to injection into the capillary. Adjustments in the denaturing sample buffers are made as necessary to account for any electroosmotic flow or heating effects that occur (see, e.g., Kilar, F., "Isoelectric Focusing in Capillaries," in *CRC Handbook on Capillary Electrophoresis: A Practical Approach*, CRC Press, Inc., chapter 4, pp. 95-109 (1994)).

The amount of sample injected can vary and, as noted above, depends in part of the size of the capillary used. In general, the capillary is loaded with 0.1 to 5.0 mg of sample. Samples can be spiked with one or more known pI standards to assess the performance of the method.

4. Elution

A variety of techniques can be utilized to elute or withdraw electrophoretic medium containing resolved compounds out from the capillary, but these methods fall into three general categories: hydrodynamic elution, electroelution and control of electroosmotic flow.

a. Hydrodynamic/Pressure Elution

Hydrodynamic or pressure elution involves applying pressure (or pulling a vacuum) via an appropriate pump connected with one end of the capillary (see, e.g. Kilar, F., "Isoelectric Focusing in Capillaries," in *CRC Handbook on Capillary Electrophoresis: A Practical Approach*, CRC Press, Inc., chapter 4, pp. 95-109 (1994)). However, hydrodynamic elution can cause band broadening and loss of resolution due to the parabolic flow profile that is formed in the capillary.

b. Electroelution

Electroelution, the other major approach, encompasses a variety of techniques and in general involves altering the solution at the anode and/or cathode to change some parameter (e.g., pH, ionic strength, salt concentration) of the electrophoretic medium in the separation cavity sufficiently to effect elution.

i. Salt Mobilization

One electroelution approach involves addition of a salt to the catholyte or analyte, the salt having a non-acidic or non-basic counterion of the same charge as the acidic or basic species within the reservoir to which the salt is added so that the counterion migrates from the reservoir into the capillary. Since electrical neutrality must be maintained within the capillary, the movement of the counterion into the capillary results in a reduction of the concentration of protons or hydroxide within the capillary and thus the pH is either raised or lowered. The theoretical basis for this type of mobilization is described by S. Hjerten, J. L. Liao. and K. Yao. *J. Chromatogr.*, 387:127 (1987). For example, if the catholyte is sodium hydroxide (i.e., the basic species is hydroxide) then a salt having a negatively charged counterion other than hydroxide is added, for example sodium chloride. Movement of chloride ion into the capillary reduces the local concentration of hydroxide within the capillary, thereby decreasing the pH. As another example, if the anolyte is phosphoric acid, then a salt having a counterion other than a proton is added, for example sodium phosphate. In this instance, movement of sodium ion into the capillary reduces the local concentration of protons within the capillary thereby increasing the pH. As the pH is lowered or raised within regions of the capillary due to the presence of the added counterion, elution occurs since the ampholytes, and the focused components, migrate to the newly-defined pH regions corresponding to their isoelectric points. It has been shown that both the type and concentration of salt used for mobilization has impact on the resolution of eluted compound peaks (see, e.g., R. Rodriguez-Diaz, M. Zhu, and T. Wehr, *J. Chromatogr. A,* 772:145 (1997)). For example, the addition of sodium tetraborate instead of sodium chloride to the catholyte results in greatly increased resolution of separated proteins.

ii. pH Mobilization

Another technique, referred to herein as "pH mobilization" can also be utilized to elute compounds during CIEF. In this approach, an additive is added to either the anode or cathode solution to alter the pH of the solution. Unlike salt mobilization, however, the additive does not contribute a mobile counterion that moves into the capillary. Here, the elution occurs as a result of the pH gradient being redefined by the pH of one or both of the reservoirs; therefore, components with pI's that fall outside of this redefined pH gradient are eluted into either the anode or cathode reservoirs. Typically, the technique for cathodic mobilization proceeds as follows. Once the components are focused (e.g., in a pI range of 3-10 using phosphoric acid as the anolyte and sodium hydroxide as the catholyte) the cathodic capillary end is immersed into a reservoir containing a solution that has a pH slightly less than 10, for example 50 mM imidazole (pKa 7) which has a pH of 9.85. The components are then allowed to refocus in the capillary, recognizable by a stabilization of the current through the capillary, the pI range now being defined by 3-9.85. Any components with an isoelectric point of 9.85 to 10 are eluted into the catholyte. The process can be repeated with catholyte containing a species that reduces the pH to slightly less than 9.85. In a stepwise fashion, the pH can continued to be reduced to pH 7, thereby collecting separated components in fractions that span the range of 7-10. At this point, anodic mobilization can proceed by replacing the anolyte with acids of increasing pKa to selectively increase the pH from 3 to 7, thereby collecting fractions in the acidic range (pH 3-7). The number of fractions can vary depending on the desired fractionation resolution. Typically, these fractions are defined by differences of 0.05-0.5 pH units.

The technique of pH mobilization can be useful for samples containing a high concentration of one or more components (e.g., proteins) that may cause uneven spatial gradients inside the capillary. Using pH mobilization, only those components with isoelectric points below or above the pI range that is defined by the reservoir pH's are eluted. This elution is, therefore, reproducible regardless of differences in the shape of the capillary pH gradient or the presence of uneven spatial gradients inside the capillary.

c. Electroosmotic Flow (EOF)

Regulating the magnitude of electroosmotic flow (EOF) significantly affects the preceding electroelution methods (see supra) and is another means by which resolved components can be selectively withdrawn upon conclusion of an isoelectric focusing separation. EOF is generated by the ionization of silanol functionalities on the surface of a silica capillary. Such ionization results in a layer of protons in the electrophoretic medium at the surface of the silica capillary. Once an electric field is applied, the layer of protons essentially constitutes a positively charged column of fluid that migrates toward the cathode, thereby causing bulk flow of the electrophoretic medium within the capillary. Apparent velocity of components is equal to the sum of the electroosmotic flow and their electrophoretic mobility. Thus, by controlling EOF, one can control or regulate the rate at which components move through the capillary. In CIEF methods, generally EOF should be controlled to allow components within an injected sample sufficient time to focus before the proteins begin eluting from the capillary.

A variety of techniques can be utilized to regulate EOF. One approach involves coating the walls of capillaries with various agents. For example, EOF alone glass silicate surfaces can be substantially reduced by silanizing them with a neutral silane reagent that masks a substantial percentage of surface silanol groups (e.g., polyacrylamide, polyethylene glycol and polyethylene oxide). The magnitude of EOF can be further controlled using silanizing reagents that include positively or negatively charged groups. Positively charged coatings can be used to nullify surface negative charges to give a net surface charge of zero so that EOF approaches zero. Coatings with higher positive charge densities can be used to reverse the direction of EOF for charged surface materials. This can be useful for slowing the net migration rates of positively charged sample species. Conversely, negatively charged coatings can be used to impart to or increase the magnitude of the negative charge on surfaces, so as to increase the net migration rates of negatively charged species. Representative positively charged coatings include trialkoxysilanes with polyethyleneimine, quaternized polyethyleneimine, poly(N-ethylaminoacrylamide) and chitosans, for example. Representative negatively charged coatings include trialkoxysilanes with carboxylate and sulfonate containing materials such as poly(methylglutamate) and 2-acrylamido-2-methylpropanesulfonate polymers, for example. Charged coatings can also effectively reduce sample adsorption, especially for samples having the same charge polarity as the coating.

The separation medium can also include soluble agents for dynamically coating the walls of the separation cavity, to help reduce EOF during electrophoresis. Such soluble coating agents include quaternary ammonium-containing polymers, methyl cellulose derivatives, cellulose acetate, polyethylene oxide, chitosan, polyvinyl alcohol, polyethylene glycol, polyethylenimine, and polyethylene oxide-polypropylene oxide-polyethylene oxide triblock copolymers, for example. Typically, soluble coating agents are included at concentrations of about 0.05% to about 4%, and more typically of about 1% to about 2%.

EOF and sample absorption can also be adjusted by including suitable reagents in the separation medium and running buffers. For example, negative surface charges can be masked by including a cationic additive in the medium, such as metal amine complexes, amines and polyamines such as propylamine, triethylamine, tripropylamine, triethanolamine, putrescine, spermine, 1,3-diaminopropane, morpholine, and the like. Zwitterionic species comprising both negatively and positively charged groups that are isoelectric at the pH of electrophoresis can also be used, such as trialkylammonium propyl sulfonates, where alkyl is methyl, ethyl, propyl, and longer alkyl chains.

Another approach involves the generation of a current that opposes EOF. Typically, this is accomplished by applying a thin film of metal (e.g. iridium tin oxide or copper) to an external surface of the capillary. Application of current to the film generates a relatively small induced current within the capillary to reverse the EOF (see, e.g., Schasfoort, R. B. M., Schlautmann, S., Hendrikse, J., and van den Berg, A., "Field-Effect Flow Control for Microfabricated Fluidic Networks," *Science,* 286:942-945 (1999)).

Figure 2B:
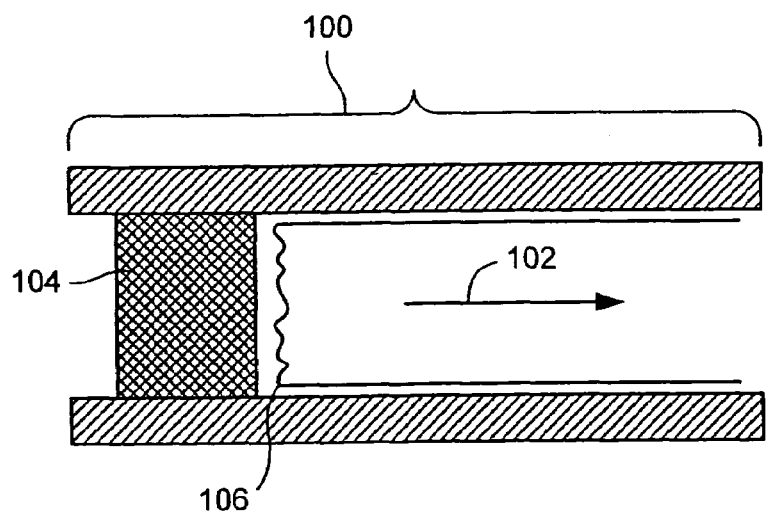
FIG. 2B is a cross-sectional view of a capillary showing the orientation of a porous plug inserted into the capillary to control electroosmotic flow in certain methods of the invention.

Placing a porous plug at a location upstream from where sample is introduced (upstream referring to a direction opposite the flow of components through the capillary) can also be utilized to control EOF. An example illustrating the location of the plug is illustrated in FIG. 2B where the capillary 100 extends from the anode reservoir (not shown) at one end and the cathode reservoir at the other end (not shown). Component migration is in the direction of arrow 102 (i.e., from the anode to cathode direction).

As can be seen, the porous plug 104 is positioned to be upstream of the trailing edge 106 of the sample once introduced into the capillary 100. The porous plug 104 is typically formed of a polymeric material and remains relatively stationary during electrophoretic runs. Examples of suitable materials from which the plug can be formed include polymerized acrylamide with diacrylamide crosslinkers and agarose. Although not intending to be bound by any particular theory, the porous plug 104 appears to function as a momentum transfer barrier by blocking replacement of bulk fluid that in the absence of the plug 104 would move toward the cathode reservoir.

In some methods, such as those containing large amounts of a particular component (e.g., a protein) and/or a large number of different components, EOF should be reduced to very low levels to allow components the opportunity to focus before the electrophoretic medium begins eluting from the capillary due to EOF. In certain methods an EOF of $=0.5 \times 10^{-6}$ cm$^2$/V–s (at pH 8.6, and 25 ml4 TRIS-phosphate) has been found to allow ample time for the necessary focusing of proteins before sample elutes from the capillary. Methods described above can reduce EOFs to these levels.

Thus, the foregoing approaches enable fractions to be collected according to different criteria. Electroelution techniques, for example, can be used to collect fractions having a defined pH range. BOF elution and pressure elution, in contrast, can be used to separate fractions according to time of elution. Other techniques can also be utilized to elute resolved proteins after CIEF (see, e.g. Kilar, F., "Isoelectric Focusing in Capillaries," in *CRC Handbook or Capillary Electrophoresis: A Practical Approach*, CRC Press, Inc.. chapter 4. pp. 95-109 (1994)). The controlled elution techniques are useful for enhancing reproducibility, an important factor in comparative and diagnostic methods. Such techniques also provide improved tolerance of high abundance components such as proteins as compared to methods relying on spatial separation.

B. Capillary Zone Electrophoresis (CZE)

1. General

Capillary zone electrophoresis is an electrophoretic method conducted in free solution without a gel matrix and results in the separation of charged components (e.g., proteins, amino acids, fatty acids, fats, sugar phosphates, nucleic acids, nucleotides and nucleosides) based upon their intrinsic charge-to-mass ratios. One advantage to CZE methods is the ability to run with solvent systems that would normally be incompatible with typical water soluble gel matrices. Nonaqueous or water miscible solvent systems can be used to improve the solubility of hydrophobic and membrane bound components that would normally not be resolved by aqueous electrophoretic methods. General methods for conducting the method are described, for example, by McCormick, R. M. "Capillary Zone Electrophoresis of Peptides," in *CRC Handbook of Capillary Electrophoresis: A Practical Approach*, CRC Press Inc., chapter 12, pp. 287-323 (1994); Jorgenson, J. W. and Lukacs, K. D., *J. High Resolut. Chromatogr. Commun.*, 4:230 (1981); and Jorgenson, J. W. and Lukacs, K. D., *Anal. Chem.* 53:1298 (1981)), each of which is incorporated by reference in its entirety.

2. System and Solutions

In general, the capillaries described above for CIEF are also suitable for conducting CZE methods. Often the capillaries have internal diameters of about 50 to 100 microns. Buffer composition and pH can significantly influence separations since separations in CZE are based upon charge-to-mass ratios and the charge of a component is dependent upon the pH of the surrounding solution. At the extremes of pH (i.e., below 2 and above 10) it is typically difficult to achieve resolution of many components because most charged groups on the components are either fully protonated or deprotonated and many components have a similar numbers of acidic and basic residues per unit mass. Selectivity is typically enhanced at intermediate pH. For components having a relatively high percentage of acidic groups selectivity can often be enhanced near pH 4.5. For those components having a high concentration of amine residues, selectivity can be enhanced near pH 10.

In CZE, solutions at the anode and cathode are typically the same. The buffer utilized can be essentially any buffer, the choice of buffer being controlled in part by the pH range at which the electrophoretic method is conducted and its influence on the detector noise. Examples of useful buffers at low pH include, but are not limited to, phosphate and citrate; useful buffers at high pH include Tris/Tricine, borate and CAPS (3-(cyclohexylamino)-1-propane sulfonic acid). Further guidance regarding suitable buffers and buffer additives is described by McCormick, R. M. "Capillary Zone Electrophoresis of Peptides," in *CRC Handbook of Capillary Electrophoresis: A Practical Approach*, CRC Press Inc., chapter 12 , pp. 287-323 (1994).

In some instances, multiple CZE separations can be conducted with different pH buffers to affect the fractionation of components. For example, a buffer of pH 3 can be used to resolve net positively charged amine functional components (e.g., amino acids, and nucleosides), from neutral (e.g., oligosaccharides, polysaccharides, simple sugars, and fatty acids), and from net negatively charged components (e.g., phosphosugars and nucleotides). Fractions collected from this first CZE dimension can subsequently be further resolved in a second CZE dimension at another pH. For example, the amino acids can be resolved from nucleosides by a second CZE dimension conducted at pH 7 and fatty acids can be resolved from the amino acids at pH of 5.5. The phosphosugars can be further resolved from carboxylic acids by subsequent CZE separation at pH 11.

3. Elution

Elution can be accomplished utilizing some of the same methods described above for CIEF, namely pressure and EOF. As with CIEF, controlling EOF can be important in certain methods to prevent electrophoretic medium containing components from eluting from the capillary before the components within the loaded sample have had an opportunity to separate. EOF can be controlled using the same methods utilized for controlling EOF in CIEF methods (e.g., coating the internal walls of the capillary, using a porous plug and generating an induced field to counteract EOF). Regulating and carefully selecting the pH and ionic strength of the electrophoretic medium is another technique that can be used. Because EOF results from ionization of the silanol groups on the interior capillary surface, by conducting CZE at relatively low pH (e.g., pH 2-5, more typically about pH 3-4) the number of silanol groups that are ionized is reduced. Such a reduction reduces EOF. To prevent sample elution prior to complete separation, in certain analyses the EOF should be reduced to $<1\times10^{-4}$ cm$^2$/V-s (at pH 8.6 and 25 mM TRIS-phosphate buffer). EOFs of this level can be obtained using the methods just described.

Covalent modification of one or more analytes can also be used strategically as a means to control component elution. This technique involves adding a chemical moiety to certain components in the sample or a fraction collected from a CE step prior to injecting the sample into the next capillary. By selecting modifying agents that preferentially react with certain functional groups such as amino or carboxyl groups, the charge-to-mass ratio of certain components can be altered. Such alterations can improve the resolution of components during electrophoresis as well as improve their detectability.

C. Capillary Gel Electrophoresis (CGE)

1. General

Capillary gel electrophoresis refers to separations of proteins, nucleic acids, or other macromolecules accomplished by sieving through a gel matrix, resulting in separation according to size. In one format, proteins are denatured with sodium dodecyl sulfate (SDS) so that the mass-to-charge ratio is determined by this anionic surfactant rather than the intrinsic mass-to-charge ratio of the protein (Cantor, C. R. and Schimmel, P. R. *Biophysical Chemistry*, W.H. Freeman & Co., N.Y., (1980)). This means that proteins can be separated solely on the basis of size without charge factoring into the degree of separation. The application of general SDS PAGE electrophoresis methods to capillary electrophoresis (CGE) is described, for example, by Hjerten, S., *Chromatogr. Rev.*, 9:122 (1967).

2. System and Solutions

The type of capillaries and their size are generally as described above for CZE. A variety of different buffers can be used, including commercially available buffers such as the "eCAP SDS" buffers manufactured by Beckman (Hjertén, S., *Chromatogr. Rev.*, 9:122 (1967); Beckman Instruments, "eCAP SDS 200: Fast, reproducible, quantitative protein analysis," BR2511B, Beckman Instruments, Fullerton, Calif., (1993); Gottlieb, M. and Chavko, M., *Anal. Biochem.*, 165:33 (1987); Hochstrasser, D. F., et al., *Anal Biochem.*, 173:424 (1988)). Various buffer additives can be utilized to increase resolution. Such additives, include, but are not limited to, small amounts of organic solvents, such as N,N-dimethylformamide, cyclohexyldiethylamine, dimethoxytetraethylene glycol and other polyols (e.g., ethylene glycol and polyethylene glycol) (see, e.g., Palmieri, R. and Nolan, J. A., "Protein capillary electrophoresis: Theoretical and experimental considerations for methods development," in: *CRC Handbook of Capillary Electrophoresis: A Practical Approach*, Chp. 13, pgs. 325-368, CRC Press, Boca Raton, (1994); Wanders, B. J. and Everaerts, F. M., "Isotachophoresis in capillary electrophoresis," in: *CRC Handbook of Capillary Electrophoresis: A Practical Approach*, Chp. 5, pgs. 111-127, CRC Press, Boca Raton, Fla., (1994)). The use of such solvents can improve the solubility of certain compounds such as lipophyllic components in aqueous solution and enhance their stability against thermal denaturation, (Martinek, K., et al., *FEBS Lett.*, 51:152-155 (1975)) depress the electroosmotic flow in CZE and CGE (Altria, K. D. and Simpson, C. F., *Anal. Proc.*, 23:453 (1986)), alter the electrical double-layer thickness at the capillary wall to inhibit protein binding interactions (Mc Cormick, R. M., "Capillary zone electrophoresis of peptides," in: *CRC Handbook of Capillary Electrophoresis: A Practical Approach*, Chp. 12, pgs. 287-323, CRC Press, Boca Raton, Fla., (1994)) and increase the viscosity of the running buffer which depresses the electroosmotic flow. Solvents utilized should be compatible with the polymer matrix inside the capillary.

Isotachophoresis (IPE) can be used in certain methods to increase resolution of charged components. For a general discussion of IPE. see, for example, B. J. Wanders and Everaerts, F. M., "Isotachophoresis in Capillary Electrophoresis," in *CRC Handbook of Capillary Electrophoresis: A Practical Approach*, chap. 5, pp. 111-127 (1994), which is incorporated by reference in its entirety. The velocity of a charged molecule moving through a capillary under a constant field strength depends on its relative mobility which is a function of the mass/charge of the molecule, temperature and viscosity of the medium through which it is moving. However, in the absence of an adequate concentration of highly mobile ions upstream of the sample ions, all the ions eventually have to migrate at the speed of the slowest ion once the electric field reaches a steady-state inside the capillary. This condition causes the anions to stack in order of their relative mobilities at the interface of the leading and terminating buffers.

Under SDS denaturing conditions, all the components present in the sample have nearly identical mass/charges. By using a higher mass/charge anion in the terminal buffer, one can force the components to move at a constant slow speed through the capillary. This has two effects. First, components "stack" at the terminal edge of the leading buffer increasing their effective concentration inside the capillary. Second, any separation between components is based on their size. Therefore, the use of a hybrid IPE-CGE method in which the IPE is used for sample "stacking" can improve the resolution possible in the subsequent CGE separation in some methods.

Various terminal buffer systems can be utilized in conjunction with IPE methods. In one system, ε-aminocaproic acid (EACA) is used as the terminal electrolyte because it has a high mass/charge at high pH (>6). Tris(hydroxyethyl)aminomethane (TRIS) citrate at 0.05M is used as the leading buffer at pH=4.8 and as an intermediate stacking buffer at pH=6.5. The sample components (e.g., proteins) initially "stack" because EACA has a very low mobility in the pH 6.5 stacking buffer, but once the protein "stack" and EACA reach the lower pH leading buffer, the mobility of the EACA surpasses that of the components in the sample and separation commences (see, e.g., Schwer, C. and Lottspeich, F., *J. Chromatogr.*, 623:345 (1992)). This system can be used to create a hybrid single column IPE-CPAGE system.

A 2 buffer system for IPE for the separation of proteins involves dissolving sample in 0.01M acetic acid, which is also used as the terminal electrolyte. The leading and background buffer was 0.02M triethylamine-acetic acid solution at pH 4.4. The sample in terminal buffer is sandwiched between the leading and background buffer. IPE continues until the background buffer overtakes the leading edge of the terminal buffer at which point IPE stops and separation begins (see, e.g.. Foret, F. et al., *J.Chromatogr.*, 608:3 (1992)).

Another IPE approach that can be accomplished with any running buffer is to dissolve the sample in the running buffer but diluted to a lower ionic strength. This causes an increase in the electrical resistance in the capillary where the sample plug is loaded and correspondingly faster movement of the ions present in the sample matrix to running buffer boundary. The optimal ionic strength difference between the sample matrix and the running buffer is typically about 10-fold (see, e.g., Shihabi, Z. K. and Garcia, L. L., "Effects of sample matrix on separation by capillary electrophoresis," in: *CRC Handbook of Capillary Electrophoresis: A Practical Approach*, Chp. 20, pgs. 537-548, CRC Press. Boca Raton, Fla., (1994)).

3. Elution

In general, the discussion of elution for CZE applies to CGE. Elution can be accomplished utilizing pressure and EOF. As with CIEF and CZE, controlling EOF can be important in certain methods to prevent electrophoretic medium containing components from eluting before the components within the applied sample have had an opportunity to separate. The methods described supra for CIEF and CZE can be used to control EOF at desired levels. To prevent sample elution prior to complete separation, in certain analyses the EOF should be reduced to $<1 \times 10^{-4}$ cm$^2$/V–s (at pH 8.6 and 25 mM TRIS-phosphate buffer). EOF can be reduced to this range, for example, by controlling the pH of the buffer, by generation of a counteracting induced field, capillary coatings and a porous gel plug.

D. Detection Subsequent to Separation

As indicated in FIG. 1, electrophoretic solution withdrawn during the final electrophoretic separation can be directed toward an analyzer 82 for the determination of the relative abundance of the labeled and unlabeled analytes. This arrangement provides considerable flexibility with regard to the nature of detection and does not limit the methods to the standard absorbance and fluorescence techniques. The analyzer need not be positioned to detect eluted components as shown in FIG. 1, however. In other arrangements, the analyzer is adapted so that it can scan resolved components within the separation cavity of the capillary tube itself. An example of such an arrangement involves the use of a near IR analyzer to detect $^{13}$C abundance in the resolved components. Since the metabolic flux is only determined from the relative abundance of the isotopic ratios of the analytes of interest, any detector able to resole the relative abundance of labeled and unlabeled analytes can be used with the method. The quantitative sensitivity and accuracy of the detector are relatively unimportant, since each analyte is present simultaneously in both the labeled and unlabeled forms. The detector should only be capable of precisely quantifying the relative abundance of the isotope.

In some instances, a detector can be placed at the end of the final capillary column (and/or between other columns) to monitor flow and/or to determine when fractions should be collected.

E. Exemplary Systems

The methods of the invention are amenable to a variety of different electrophoretic methods. The controlled elution techniques whereby defined fractions are separated spatially, physically or by time, and the labeling and detection methods can be utilized in a number of different electrophoretic techniques. As noted above, the number of electrophoretic methods linked in series is typically at least two, but can include multiple additional electrophoretic methods as well. In some instances, each electrophoretic method in the series is different; whereas, in other instances certain electrophoretic methods are repeated at different pH or separation matrix conditions.

Despite the general applicability of the methods, as noted above CIEF, CZE and CGE methods are specific examples of the type of electrophoretic methods that can be utilized according to the methods of the invention. In certain methods, only two methods are performed. Examples of such methods include a method in which CIEF is performed first followed by CGE. Labeling, if performed, is typically performed after CIEF with detection subsequent to elution of components from the CGE capillary. In another system, the first method is CGE and the final method is CZE. Isotope detection generally is not performed until the completion of the final electrophoretic separation. However, as indicated above, UV/VIS or LIF detection may be used during any or all separation dimensions to monitor the progress of the separations particularly to determine when fractions are to be collected. A third useful approach involves conducting multiple CZE dimensions. These are specific examples of systems that can be utilized; it should be understood that the invention is not limited to these particular systems. Other configurations and systems can be developed using the techniques and approaches described herein.

VI. Mass Spectroscopy Methods

Charged or ionizable analytes can be detected by a variety of mass spectrometric methods. Certain method include electrospray (ESI) and matrix assisted laser desorption ionization (MALDI) methods coupled with time-of-flight (TOF) ion detection. ESI and MALDI are preferred because they are low energy ionization methods, generally resulting in low fragmentation of most analytes, and are suitable for the ionization of the broadest possible array of target analytes. TOF detection is useful because the accuracy of this technique in determining mass generally allows isotopic resolution to the single atomic mass unit level, even for multiply charged species. However, other mass spectrometric ionization and detection techniques can be usefully employed where the analytes are particularly robust to fragmentation, the isotopic differences between labeled and unlabeled analytes is sufficiently large, and/or the number of charge states sufficiently low, to achieve resolution of the labeled and unlabeled analytes.

VII. Microfluidic Systems

A. Examples of configurations

In a variation of the electrophoresis systems described supra, the capillaries are part of or formed within a substrate to form a part of a microfluidic device that can be used to conduct the analyses of the invention on a very small scale and with the need for only minimal quantities of sample. In these methods, physical fractions of samples typically are not collected. Instead, resolved components are separated spatially or by time. Methods for fabricating and moving samples within microfluidic channels or capillaries and a variety of different designs have been discussed including, for example, U.S. Pat. Nos. 5,858,188; 5,935,401; 6,007,690; 5,876,675; 6,001,231; and 5,976,336, all of which are incorporated by reference in their entirety.

Figure 3A:
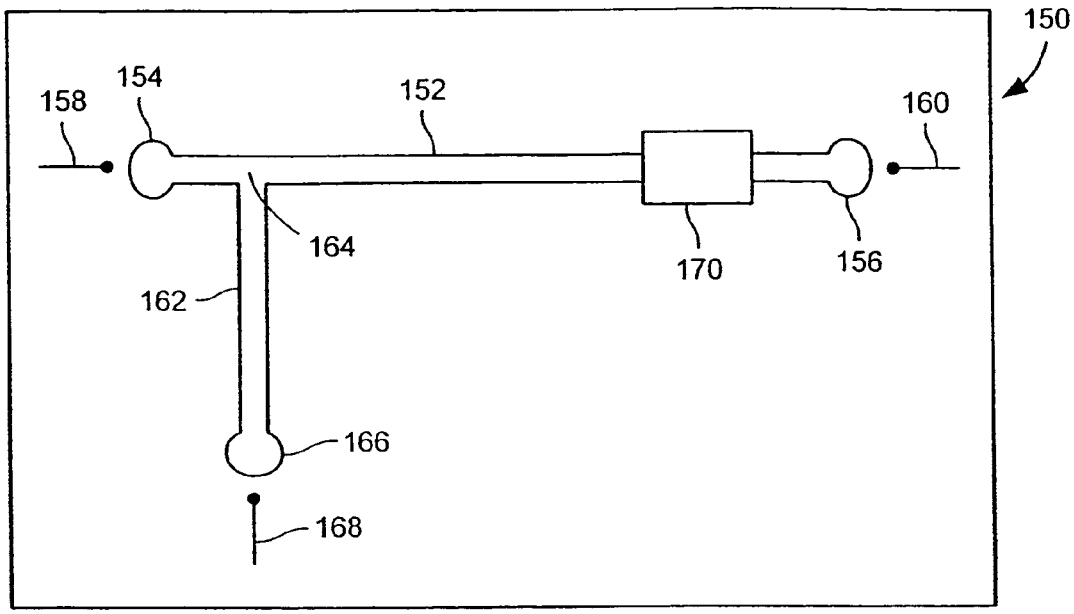
FIGS. 3A and 3B are top-views of certain elements of microfluidic devices that can be utilized to conduct certain electrophoretic methods of the invention.

An example of a general system 150 that can be used with the methods of the present invention is depicted in FIG. 3A. The capillaries or channels are typically formed or etched into a planar support or substrate. A separation capillary 152 extends from an anode reservoir 154 containing anolyte to a cathode reservoir 156. The anode reservoir 154 and the cathode reservoir 156 are in electrical contact with an anode and cathode 158, 160, respectively. A sample injection channel 162 runs generally perpendicular to the separation capillary 152 and one end intersects at an injection site 164 slightly downstream of the anode reservoir 154. The other end of the sample injection capillary 162 terminates at a sample reservoir 166, which is in electrical communication with a sample reservoir electrode 168. A detector 170 is positioned to be in fluid communication with electrophoretic medium passing through the separation capillary 152 and is positioned downstream of the sample injection site 164 and typically somewhat upstream of the cathode reservoir 156. In this particular configuration, fractions are withdrawn into the cathode reservoir 156. Movement of electrophoretic medium through the various channels is controlled by selectively applying a field via one or more of the electrodes 158, 160 168. Application of a field to the electrodes controls the magnitude of the EOF within the various capillaries and hence flow through them.

Figure 3B:
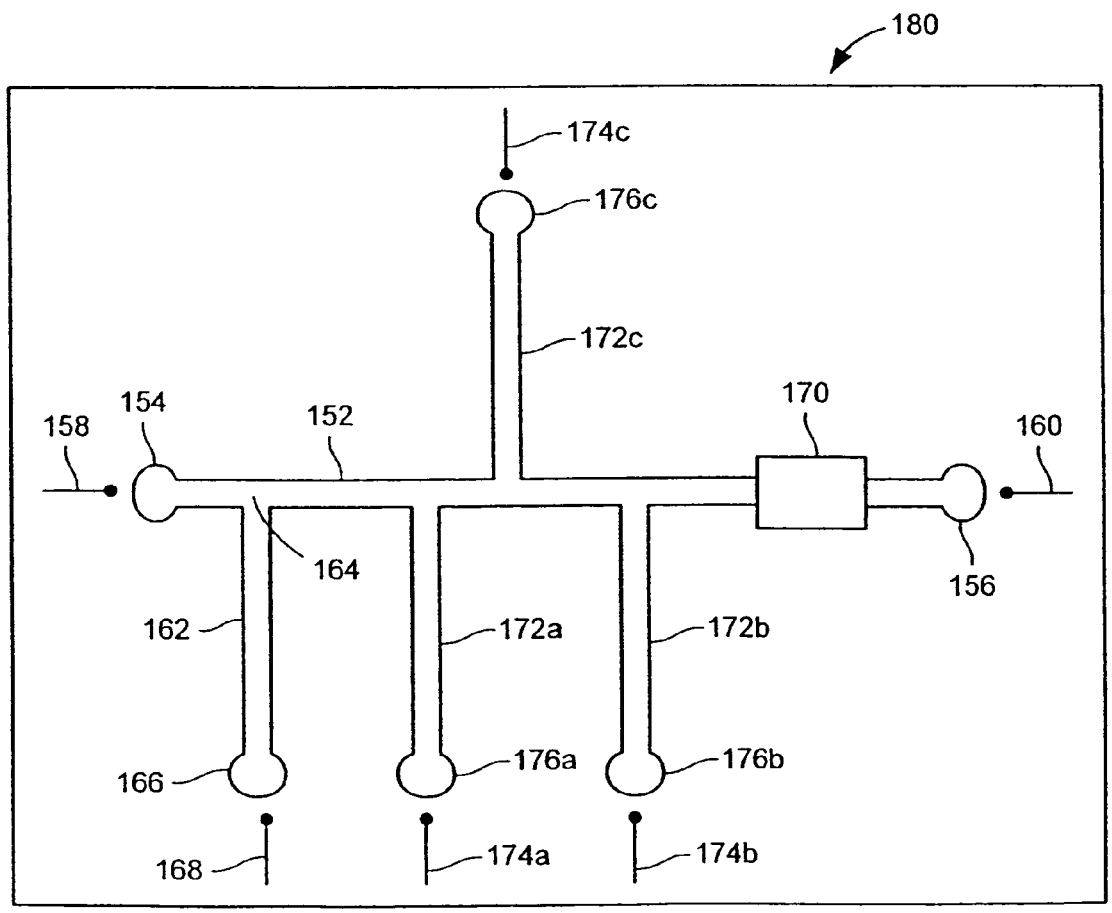

An example of another configuration is illustrated in FIG. 3B. This system 180 includes the elements described in the system shown in FIG. 3A. However, in this arrangement, spacially or temporally resolved fractions can be withdrawn at multiple different locations along the separation capillary 152 via exit capillaries 172a, 172b and 172c. Each of these capillaries includes a buffer reservoir 176a, 176b, 176c, respectively, and is in electrical communication with electrodes 174a, 174b, 174c, respectively. Movement of electrophoretic medium along separation capillary 152 and withdrawal of fractions therefrom into the exit capillaries 172a, 172b and 172c can be controlled by controlling which electrodes along the separation capillary 152 and which of the exit capillary electrodes are activated. Alternatively, or in addition, various microfluidic valves can be positioned at the exit capillaries 172a, 172b and 172c to control flow. Typically, additional detectors are positioned at the various exit capillaries 172a, 172b and 172c to detect components in fractions withdrawn into these capillaries.

The configuration illustrated in FIG. 3B can be used in a number of different applications. One example of an application for which this type of system is appropriate is a situation in which the type of samples being examined has been well characterized. If for example, certain fractions of components of interest have been previously established to fractionate at a particular location in the separation capillary 152, then the exit capillaries 172a, 172b and 172c can be positioned at those locations to allow for selective removal of the component(s) of interest.

In still another configuration, multiple exit capillaries branch from the end of the separation capillary 152 near the cathode reservoir 156, each exit capillary for withdrawing and transporting separate fractions. In this configuration also, withdrawal of fractionated components from the separation capillary can be controlled by regulating EOF within the various capillaries and/or by microfluidic valves.

Other components necessary for conducting an electrophoretic analysis can be etched into the support, including for example the reservoirs, detectors and valves discussed supra.

B. Substrates

The substrate upon which the capillary or micro-channel network of the analytical devices of the present invention are formed can be fabricated from a wide variety of materials, including silicon, glass, fused silica, crystalline quartz, fused quartz and various plastics, and the like. Other components of the device (e.g., detectors and microfluidic valves) can be fabricated from their same or different materials, depending on the particular use of the device, economic concerns, solvent compatibility, optical clarity, mechanical strength and other structural concerns. Generally, the substrate is manufactured of a non-conductive material to allow relatively high electric fields to be applied to electrokinetically transport the samples through the various channels.

In the case of polymeric substrates such as plastics, the substrate materials can be rigid, semi-rigid, or non-rigid, opaque, semi-opaque or transparent, depending upon the use for which the material is intended. Plastics which have low surface charge when subjected to the electric fields of the present invention and thus which are of particular utility include, for example, polymethylmethacrylate, polycarbonate, polyethylene terepthalate, polystyrene or styrene copolymers, polydimethylsiloxanes., polyurethane, polrinylchloride, polysulfone, and the like.

Devices which include an optical or visual detector are generally fabricated, at least in part from transparent materials to facilitate detection of components within the separation channel by the detector.

C. Channel Structure/Formation

The size and shape of the channels or capillaries formed in the substrate of he present devices can have essentially any shape, including, but not limited to, semi-circular, cylindrical, rectangular and trapezoidal. The depth of the channels can vary, but tends to be approximately 10 to 100 microns, and most typically is about 50 microns. The channels tend to be 20 to 200 microns wide.

Manufacturing of the channels and other elements formed in the surface of the substrate can be carried out by any number of microfabricating techniques that are known in the art. For example, lithographic techniques may be employed in fabricating glass or quartz substrates, for example, using established methods in the semiconductor manufacturing industries. Photolithographic masking, plasma or wet etching and other semiconductor processing technologies can be utilized to create microscale elements in and on substrate surfaces. Alternatively, micromachining methods, such as laser drilling, micromilling and the like, can be utilized. Manufacturing techniques for preparing channels and other elements in plastic have also been established. These techniques include injection molding techniques, stamp molding methods, using for example, rolling stamps to produce large sheets of microscale substrates, or polymer microcasting techniques, wherein the substrate is polymerized within a micromachined mold.

Further guidance regarding other designs and methods for using such microfluidic devices such as described above can be found, for example, in U.S. Pat. Nos. 5,858,188; 5,935, 401; 6,007,690; 5,876,675; 6,001,231; and 5,976,336, all of which are incorporated by reference in their entirety.

VIII. Exemplars Utilities

The methods and apparatus of the invention can be used to separate and detect a variety of different types of metabolic compounds, including, but not limited to, proteins, nucleic acids, polysaccharides, lipids, fatty acids, amino acids, nucleotides, nucleosides, monosaccharides and disaccharides. Consequently, the methods and apparatus can be used in a variety of metabolic applications. For example, the methods can be used to determine the flux of various metabolites. This capability can be used in biochemical, and especially metabolic, research in determining how the flux of metabolites Wearies as a function of different cellular states or in response to various external stimuli. The methods have value in clinical research by determining how the flux rates of various metabolites can vary between healthy and diseased states.

More specifically, the invention can be used to develop metomic databases. Such databases can include, for example, a register of various metabolites detected for a particular state or physiological condition of a subject. The database can be cross-referenced with additional information regarding the subject and/or the metabolite. For example, concerning the subject, the database can include information on the genus, species, age, race, sex, environmental exposure conditions, health status, sample collection methodology and type of sample. Flux values can be included for each of the metabolites stored in the database and can be cross indexed with metabolite concentration values, enzyme or transport protein concentration values responsible for the metabolic flux, or gene expression values corresponding to the proteins responsible for the metabolic flux.

Where the fluxes of a plurality of analytes are determined that represent separable components of overall cellular metabolism, a metabolic fingerprint of the subject can be obtained. Analytes from separable components of the overall metabolism are functionally defined as compounds sufficiently separated by a series of enzymatic conversion steps that the isotopic enrichment introduced by any single substrate can not be detected above the natural abundance of the isotope in that analyte, such that a second substrate must be introduced to measure the flux. In general, this functional criteria is satisfied if the target analyte is more than 5 conversion steps removed from the added substrate. For example, the administration of labeled glucose as a substrate is suitable for the determining the flux of several phosphosugars in the glycolysis pathway. However, such administration is generally not sufficient to raise the relative abundance of $^{13}C$ in amino acids, fatty acids, and proteins because of the large number of conversion steps separating the substrate from these target analytes. In such instances, the administration of an isotopically labeled amino acid can be used to determine the flux of the amino acids and proteins; the administration of an isotopically labeled fatty acid or acetate can be used to determine the metabolic flux of fatty acids.

In certain methods a plurality of metabolically separable substrates can be administered simultaneously to a subject and a pluralist of metabolically separable target analytes detected from a single sample obtained after a predetermined time from the subject. In a variation of such methods, each of the metabolically separable substrates can be labeled with a different stable isotope. For example $[^{18}O]$-glucose, $[^{15}N]$-phenylalanine, and $[^{13}C]$-acetate can be administered simultaneously to a subject to determine target analyte fluxes in the glycolysis, amino acid, and fatty acid metabolic pathways.

The invention can be employed in various screening applications. For example, the apparatus and methods of the invention can be used to identify metabolites that are correlated with certain cellular states (e.g., certain diseases). For example, the methods can be utilized to identify metabolites whose concentration or flux varies between healthy and diseased individuals or cells. Enzymes responsible for controlling the concentration and flux of such metabolites are thus identified as potential targets for drug therapy, for instance. In like manner, certain methods can be used to undertake toxicology studies to identify which metabolites, and thus the enzyme(s) controlling their formation, are affected by a toxic challenge.

Screening methods to correlate metabolites and certain cellular states are similar to the general analytical methods set forth supra. For instance, a substrate labeled with a stable isotope is administered to a test subject having a disease and at least partially metabolized by the test subject. Generally, one then partially or fully separates the target analytes of interest from other components in the sample under evaluation utilizing the various separation techniques described above. The relative abundance of the isotope in the target analytes is determined using a method capable of detecting the different isotopes to determine a flux value for each of the target analytes in the test subject. These determined values are then compared with the corresponding flux values for a control that serves as a reference for flux values in a non-diseased state.

The control can be a value (e.g., an average or mean value) for a control subject(s) (i.e., someone without the disease) determined under similar conditions. Alternatively, the control can be a range of values previously established to be representative of a non-diseased state. A difference (e.g. a statistically significant difference) between flux values for test and control indicates that the particular metabolite is correlated with the disease. Such a metabolite is a "marker" or potential marker for the disease. The flux values for the control subject can be data obtained previously under like conditions to the test, or the flux values can be determined for a control subject undergoing simultaneous treatment with the test subject under identical conditions.

Of course, similar screening methods can be conducted to develop correlations between certain metabolites and cellular states other than disease states. For example, methods can be conducted to identify metabolites that are correlated with particular developmental stages, states resulting from exposure to certain environmental stimuli and states associated with particular therapeutic treatments.

Multiple metabolites found to have a statistically significant difference in flux values between diseased and control subjects (i.e., markers) can be used to develop a "metabolic flux fingerprint" or simply a "fingerprint" for the disease. Such a fingerprint can subsequently be used to diagnosis the disease (see infra). Typically, such a fingerprint includes at least 2, 3, 4, or 5 metabolites found to be correlated with a disease. In other instances, the fingerprint includes at least 6, 7, 8, 9 or 10 such metabolites, and in still other instances 10, 15, or 20 or more such metabolites.

The results from comparative studies are transferable to a variety of diagnostic applications. For example, the "marker" or "fingerprints" can be used to screen or diagnose subjects to determine if they have, or are susceptible to, a particular disease. The methods track those described supra, except that the substrate labeled with the isotope is administered to a subject suspected to have the disease or susceptible to it (or simply an interested individual seeking to determine if they have, or are susceptible to, the disease). Flux values for the test analyte(s) (i.e., a "metabolic profile" for the test subject) are than compared with reference flux values for individual test analytes (markers) or collections of markers (fingerprints).

The reference values to which the determined values are compared can be representative of either a healthy or diseased state. Furthermore, the reference value can be a particular value or a range of values correlated with either a healthy or diseased state. For example, the reference can be a value (e.g., an average or mean value) for a control subject or subjects either having or not having the disease, the reference value determined under conditions similar to those under which the test subject was tested. Alternatively, the reference can be a range of values drawn from a population of control subjects either having or not having the disease.

If the reference is for a normal or healthy state, a difference (e.g., a statistically significant difference) between flux values for test subject and reference indicates that the test subject has, or is at risk of acquiring, the disease. Alternatively, lack of a difference indicates that the test subject does not have the disease and/or is at not at risk for acquiring the disease. If, however, the reference is representative of a diseased state, then a difference (e.g., a statistically significant difference) between test and reference values indicates that the test subject does not have and/or is not at risk of acquiring the disease. Conversely, lack of a indicates that the test subject either has or is susceptible to acquiring the disease.

Diagnostic screens are not limited to simply detecting disease states. The screens can also be used to detect other types of cellular states such as certain developmental states or toxic states, for example.

When conducting such screening tests, typically the analysis can be simplified. For example, once markers for a disease have been identified, one can establish separation conditions such that the fraction(s) containing the markers or interest is(are) known. Thus, during the screening tests, only the components in those particular fractions need to be evaluated. The reproducibility of the separation and detection aspects of the invention facilitate such analyses.

Such screening methods can be conducted for a variety of different diseases. Diseases that can be evaluated with the methods of the invention include, but are not limited to, various types of cancers, autism, microbial and viral infections, and various digestive disorders.

The methods of the invention have further utility in conducting structure activity studies. For example, the methods can be used to determine the effect that certain chemical agents or combination of agents generally have on metabolism and, more specifically, the effect on the flux of certain metabolites of interest. Such tests can identify agents that are disruptive to metabolism and pinpoint the particular metabolites effected. In other applications, once an agent has been tested initially, the agent or combination of agents can be modified and the analysis repeated to determine what effect, if any, the modifications had on metabolism. Such studies can be useful, for example., in making derivatives of a lead compound identified during initial drug screening trials.

Metabolic engineering studies can also be conducted using the methods of the invention. In such studies, a gene involved in metabolism can be genetically engineered to include certain desired mutations, or the promoter of a gene can be genetically engineered to increase or decrease the relative expression level of the gene. Using the methods described herein, one can determine what effect, if any, the genetically engineered changes have on the metabolism of the test subject.

The following examples are offered to illustrate, but not to limit, the claimed invention.

EXAMPLE 1

CZE Separation of Unlabeled Proteins

Each of five proteins (see Table 1) were obtained from Sigma-Aldrich and were suspended at 5 mg/ml in an aqueous denaturing sample buffer consisting of 25 MM tris(hydroxymethyl)aminomethane phosphate (pH 4.0), 0.5% by weight IGEPAL CA-630 (obtained from Sigma-Aldrich, Cat # I3021), and 1% by weight tris(2-carboxyethylphosphine)hydrochloride (TCEP, obtained from Pierce, Cat #20490ZZ). The protein samples were denatured in this sample buffer by heating at 95° C. for 15 min. Each of the five denatured protein samples were diluted into a cZE sample buffer to create a final solution consisting of 25 mM tris (hydroxymethyl)aminomethane phosphate buffer (pH 4.0), 8 M Urea, and a final concentration of 0.2 mg/ml of each of the five proteins. Control samples were also prepared of each denatured protein separately at 0.5 mg/ml final concentration in the same sample buffer.

TABLE 1

| Protein Standards | | | |
|---|---|---|---|
| Protein | Cat # | pI | MW (kDa) |
| Hen egg white conalbumin | C 0755 | 6.0, 6.3, 6.6 | 76.0 |
| Bovine serum albumin | B 4287 | 5.4, 5.5, 5.6 | 66.2 |
| Carbonic anhydrase II | T 6522 | 4.5 | 21.5 |
| Rabbit muscle GAPDH | G 2267 | 8.3, 8.5 | 36.0 |
| Bovine ribonuclease A | R 5503 | 9.6 | 13.7 |

The mixed protein sample and each of the control samples were run by CZE in a 60 cm×75 μm fused silica capillary (Beckman Coulter). An 800 μm detection window was located 50 cm from the anodic end of the capillary. A 160 nl sample volume was pressure injected at the anodic end and the separations conducted at 500 V/cm in a 25 mM TRIS-phosphate and 8 M urea running buffer at pH 4.0. Protein detection was accomplished by UV adsorption at 214 nm.

Figure 4:
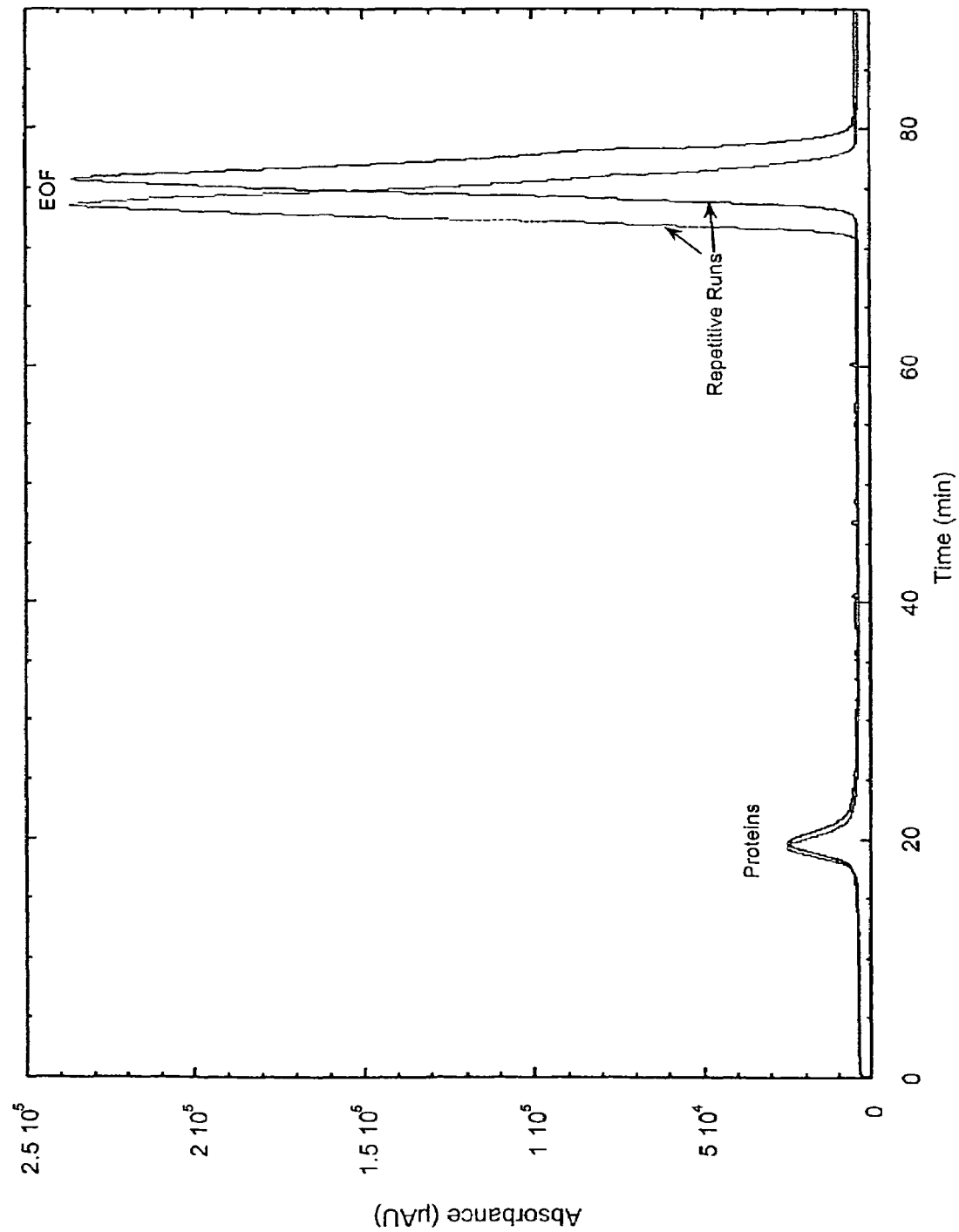
FIG. 4 is an electropherogram for a sample containing five unlabeled proteins (hen egg white conalbumin, bovine serum albumin, bovine carbonic anhydrase II, carbonic anhydrase II, rabbit muscle GAPDH, and bovine ribonuclease A) as obtained following electrophoresis by capillary zone electrophoresis. Absorbance was monitored at 214 nm. Under the conditions of this particular experiment (see Example 1) in which the proteins were unlabeled, the proteins were not resolved.
Figure 5:
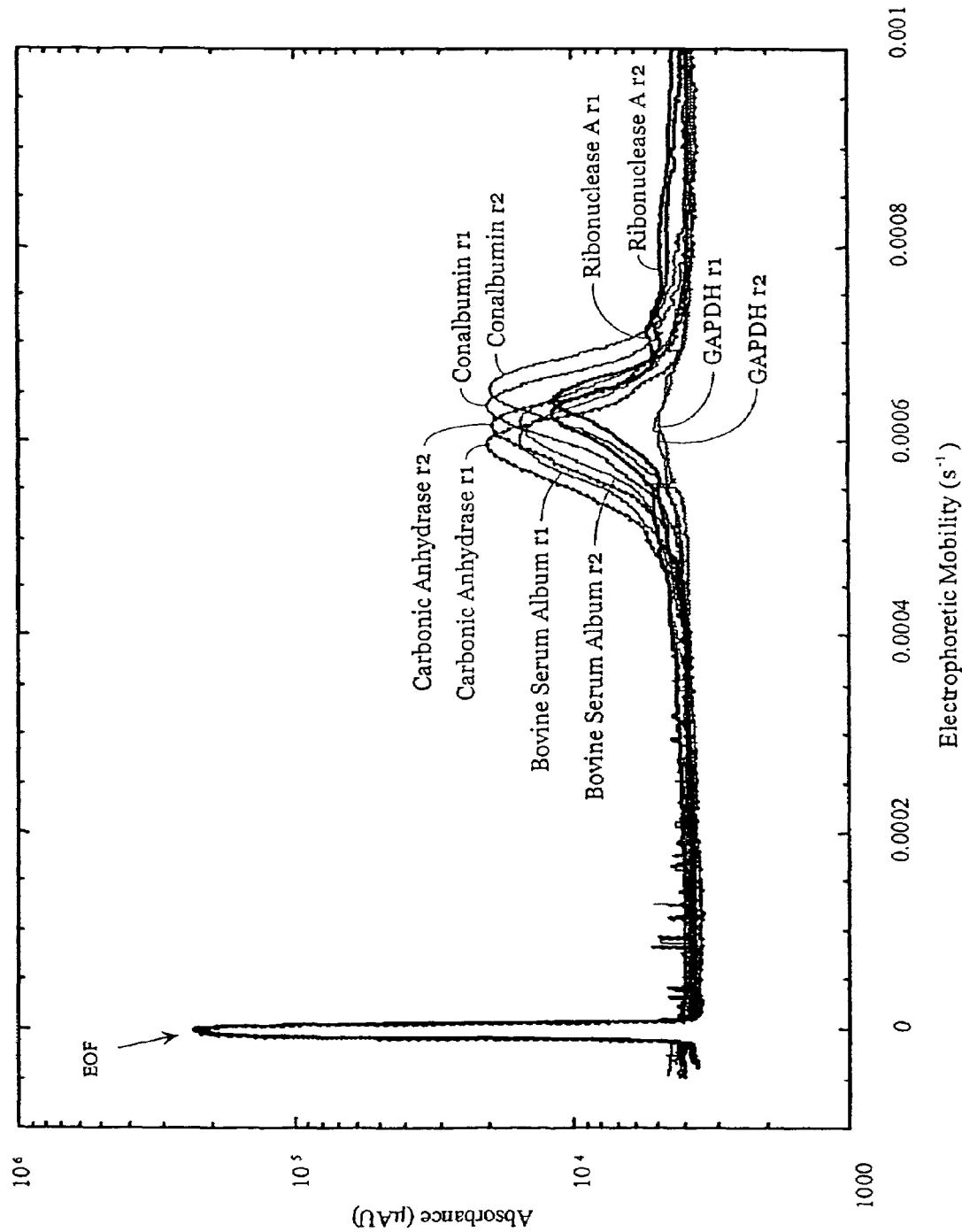
FIG. 5 is a plot of electrophoretic mobility for each of the five proteins listed in FIG. 4 under the same electrophoresis conditions as described in FIG. 4.
Figure 6:
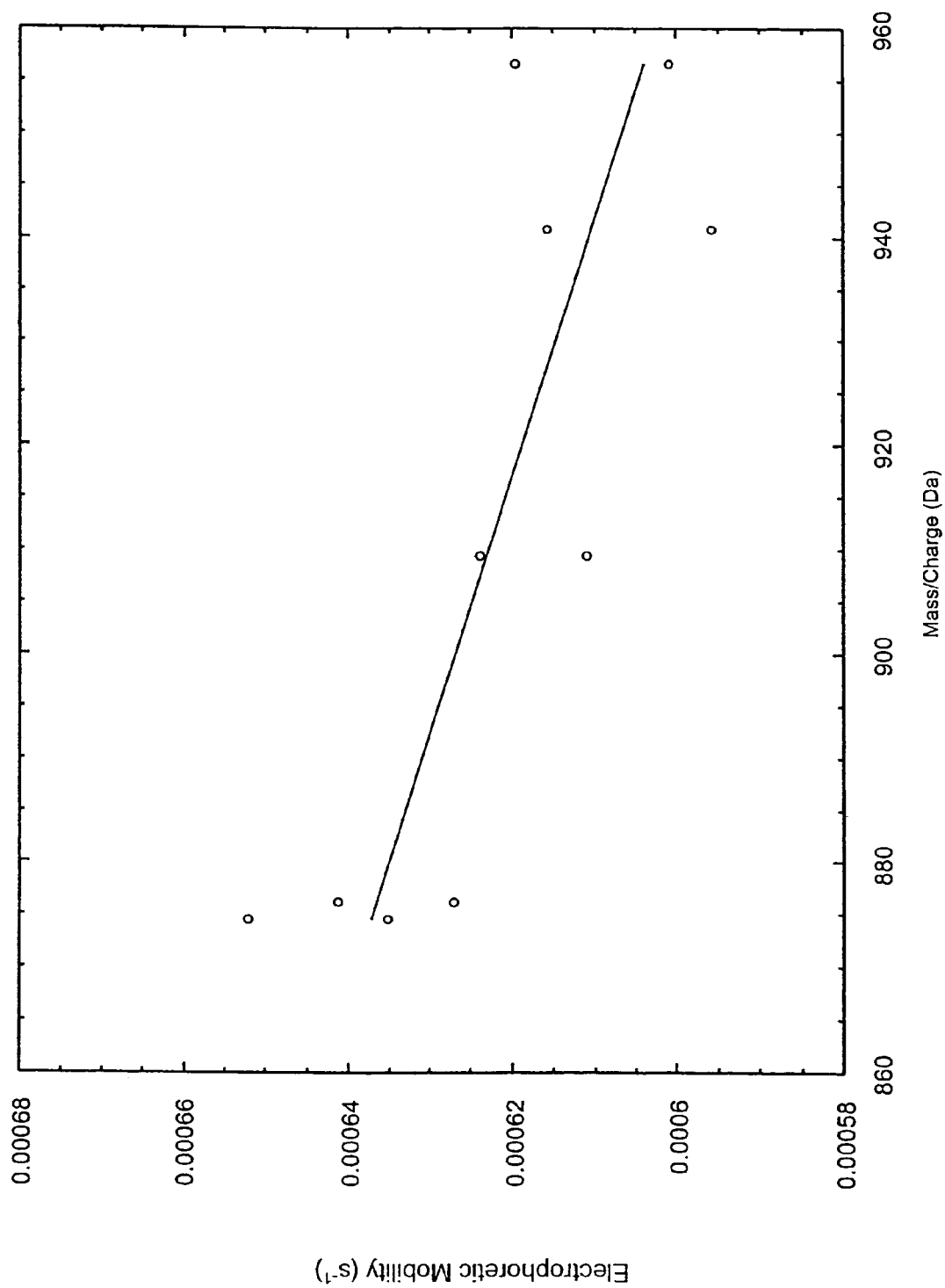
FIG. 6 is a plot showing the correlations between electrophoretic mobility and the predicted mass-to-charge ratio of the proteins at pH 4.0.

The individual unlabeled proteins were not resolved under these conditions (see FIG. 4). The electrophoretic mobility of each protein was determined from replicate runs of the individual protein controls (FIG. 5) and correlated with the predicted mass to charge ratio of the proteins at pH 4.0 (FIG. 6). The mass to charge ratio for each of the unlabeled proteins was determined from the published protein sequences obtained through Genbank in the manner described by Canter, C. R. and Schimmel, P. R., *Biophysical Chemistry*, W.H. Freeman and Co., New York, (1980), which is incorporated by reference in its entirety.

EXAMPLE 2

CZE Separation of Labeled Proteins, with Fraction Collection

Each of the five proteins described in Example 1 was suspended at 10 mg/ml in a denaturing buffer containing 1% by weight of sodium dodecyl sulfate and 1% by volume 2-mercaptoethanol.. The proteins were denatured in this buffer by heating at 95° C. for 15 min. The denatured protein samples were labeled with 4-sulfophenylisothiocyanate (SPITC) obtained from Sigma-Aldrich (Cat #85,782-3) and used as supplied. Labeling was accomplished by adding 0.01 ml of triethylamine, 0.01 ml of 2 M acetic acid and 0.02 ml of a 10% bad weight solution of SPITC in water to 0.1 ml of each denatured protein sample. The reaction mixture was heated at 50° C. for 24 h.

Figure 7:
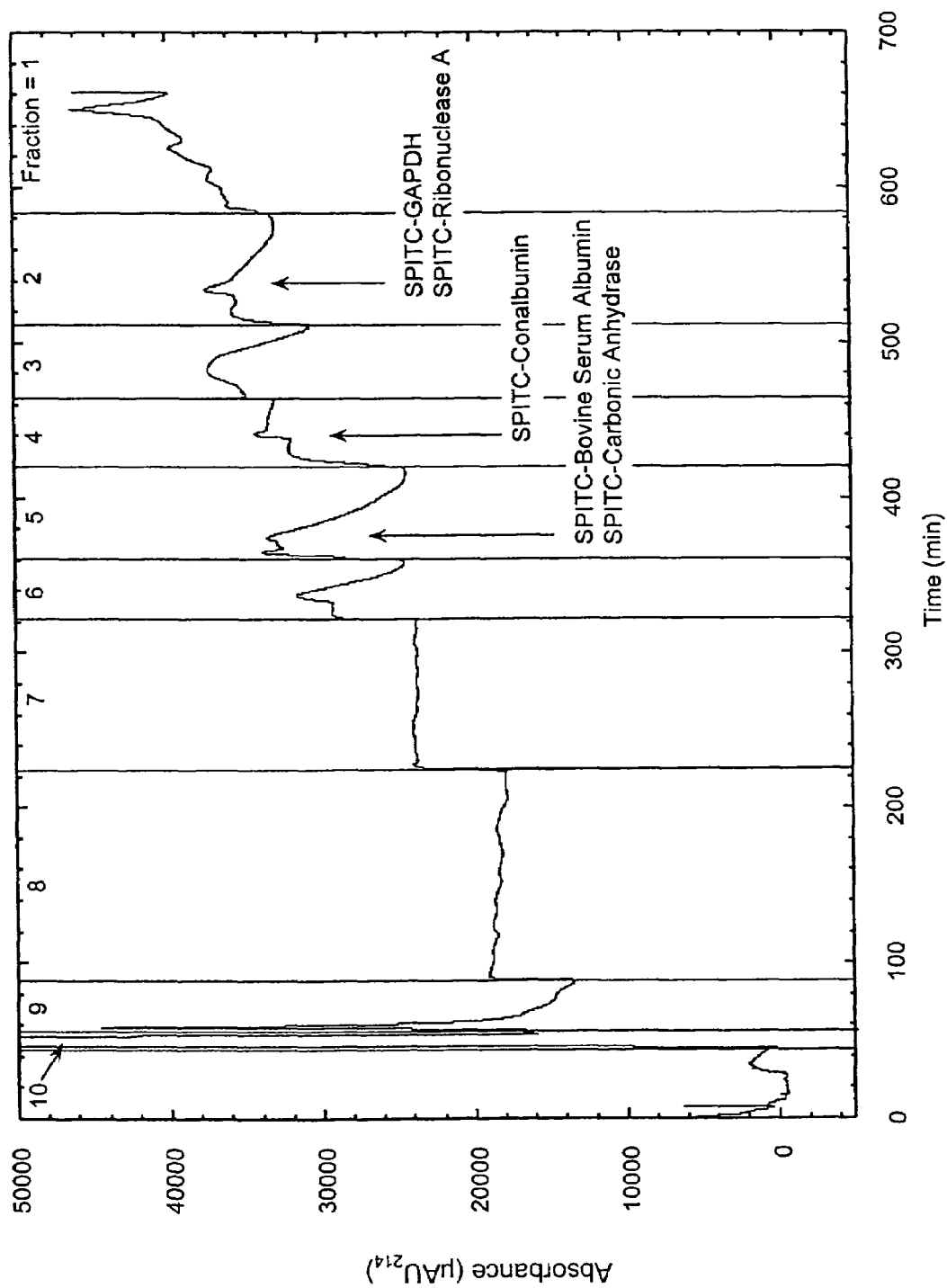
FIG. 7 is an electropherogram obtained during separation of a sample containing five sulfophenylisothiocyanate-labeled proteins (hen egg white conalbumin, bovine serum albumin, bovine carbonic anhydrase II, carbonic anhydrase II, rabbit muscle GAPDH, and bovine ribonuclease A) as obtained following electrophoresis by capillary zone electrophoresis. Absorbance was monitored at 214 nm. Under the conditions of this particular experiment (see Example 2) in which the proteins were labeled, the labeled proteins were partially resolved.

A quantity of 0.05 ml of each of the SPITC-labeled protein standards was mixed together and separated by cZE as described in Example 1, with the exception that the pH of the separation buffer was adjusted to 3.0. The individual SPITC-labeled proteins were resolved (FIG. 7). Thus, this example taken in view of the results for Example 1 in which unlabeled proteins were poorly resolved demonstrates the positive effect that labeling can have when done prior to a cZE separation. Fractions were collected by electroelution into separate vials containing the separation buffer at the times indicated. The identities of the SPITC-labeled proteins were determined by subsequent cGE analysis of the fractions.

EXAMPLE 3

CIEF First Dimension Separation with Fraction Collection

Bovine Serum Albumin, Carbonic Anhydrase, and Conalbumin were used as supplied from Sigma-Aldrich (Table 1). Each protein was denatured as described in Example 1. A 0.01 ml aliquot of each denatured protein sample was added to 0.2 ml of the CIEF focusing buffer. The CIEF focusing buffer consisted of 0.4% by weight hydroxymethyl cellulose solution (Beckman-Coulter eCAP CIEF Gel Buffer, Cat #477497) containing 1% by volume pH 3-10 Ampholytes (Fluka, Cat #10043) and 1% by weight 3-[(3-cholamidopropyl)dimethylarnnonio]-1-propane sulfonate.

A poly(ethylene glycol)-coated 60 cm long 0.1 mm internal diameter fused silica capillary (Supelcowax 10, Supelco, Cat #25025-U) was filled with the protein sample in the focusing buffer. The capillary contents were focused between 10 mM phosphoric acid and 20 mM NaOH reservoirs for 7.5 min at 500 V/cm and 25 C. A 0.5 psi pressure gradient was then applied between the anolyte and catholyte reservoirs to facilitate the elution of the focused proteins in the direction of the electroosmotic flow.

Figure 8:
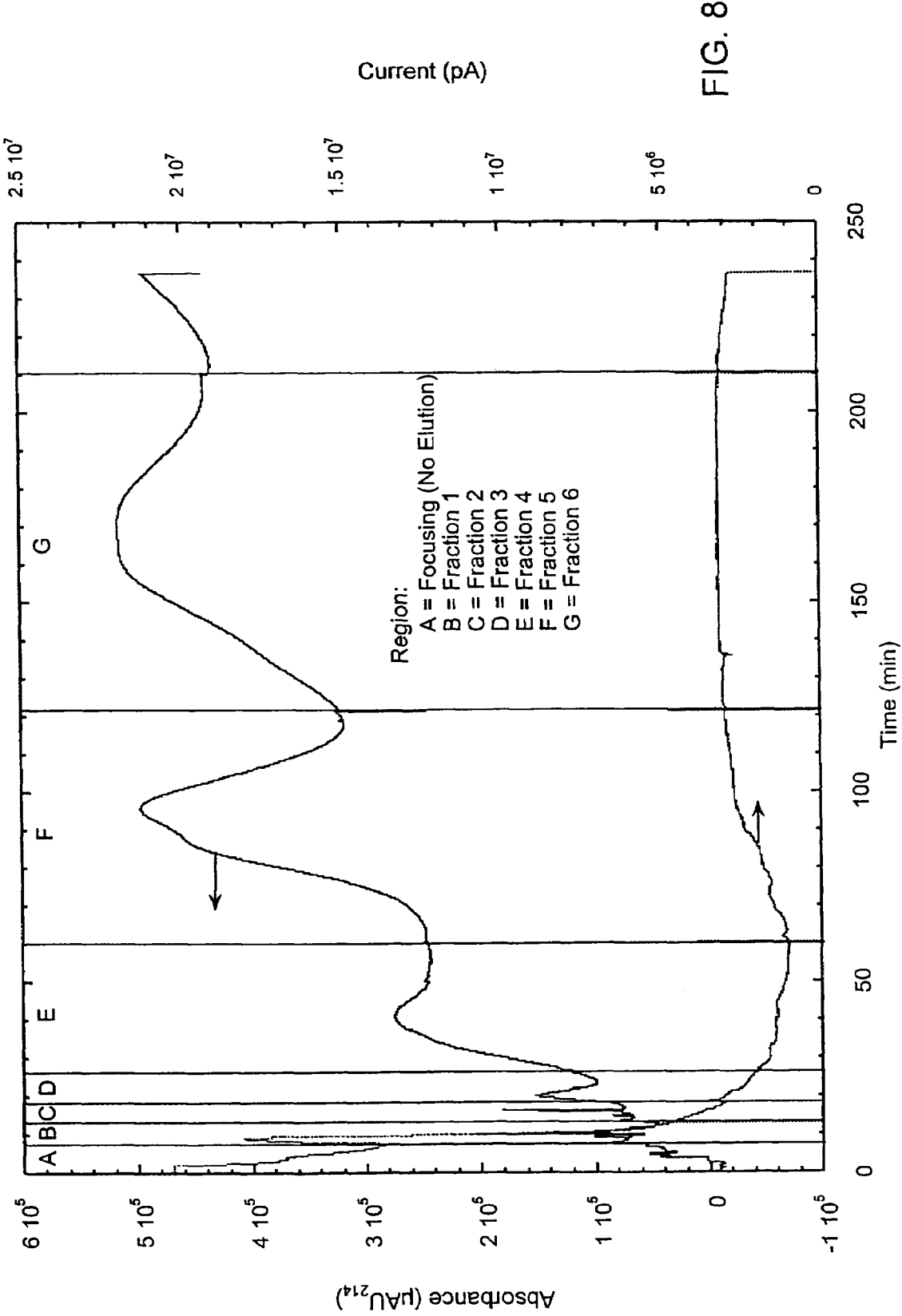
FIG. 8 is an electropherogram obtained during separation of a sample containing the proteins hen white conalbumin, bovine serum albumin, and bovine carbonic anhydrase II, by CIEF.

The protein peaks were detected by monitoring the ultraviolet absorption at 214 nm through an optical window in the capillary positioned 50 cm from the low pH end. The current through the capillary was also monitored (FIG. 8). Fractions (B-G) were collected into 0.05 ml of 20 mM NaOH contained in separate reservoir vials for the times depicted (FIG. 8). Only fractions F and G were found to contain protein (see Example 4). Fraction G was found to contain carbonic anhydrase and no conalbumin or bovine serum albumin. Conalbumin and bovine serum albumin were found to coelute in the peak observed in fraction F. This experiment illustrates the partial separation of a mixture of proteins in a single dimension. Further resolution was achieved in the second dimension (see Example 4).

EXAMPLE 4

CGE Second Dimension Separation of CIEF Fractions

Each of the CIEF fractions (B-G) collected during the CIEF separation described in Example 3 were evaporated in a Savant Model SC210A Spin-Vap to a final volume of 0.005 ml to concentrate any protein present in the fraction. A quantity 0.01 ml of SDS sample buffer was added to each protein concentrate. The SDS sample buffer consisted of 0.1 ml of eCAP SDS sample buffer (Beckman Coulter, Cat #241525), 0.01 ml of eCAP Orange G Reference Marker (Beckman Coulter, Cat #241524), and 0.09 ml of anhydrous glycerol.

Each sample was then run in CGE mode using a linear poly(acrylamide)-coated fused silica capillary 60 cm long with a 100 µm internal diameter. The eCAP SDS 14-200 Gel buffer (Beckman-Coulter Cat #477416) was used for the separation and in both reservoirs. The separation was conducted at 20° C. and 500 V/cm for 50 min. Ultraviolet detection of the proteins was accomplished at 214 nm through an optical window positioned 50 cm from the sample injection end of the capillary. Molecular weight calibration was conducted in a separate run using eCAP. MW Standards (Beckman-Coulter Cat #477418) as described by the manufacturer. A 100 sec sample injection at 0.5 psi was used to load each sample into the capillary.

Figure 9:
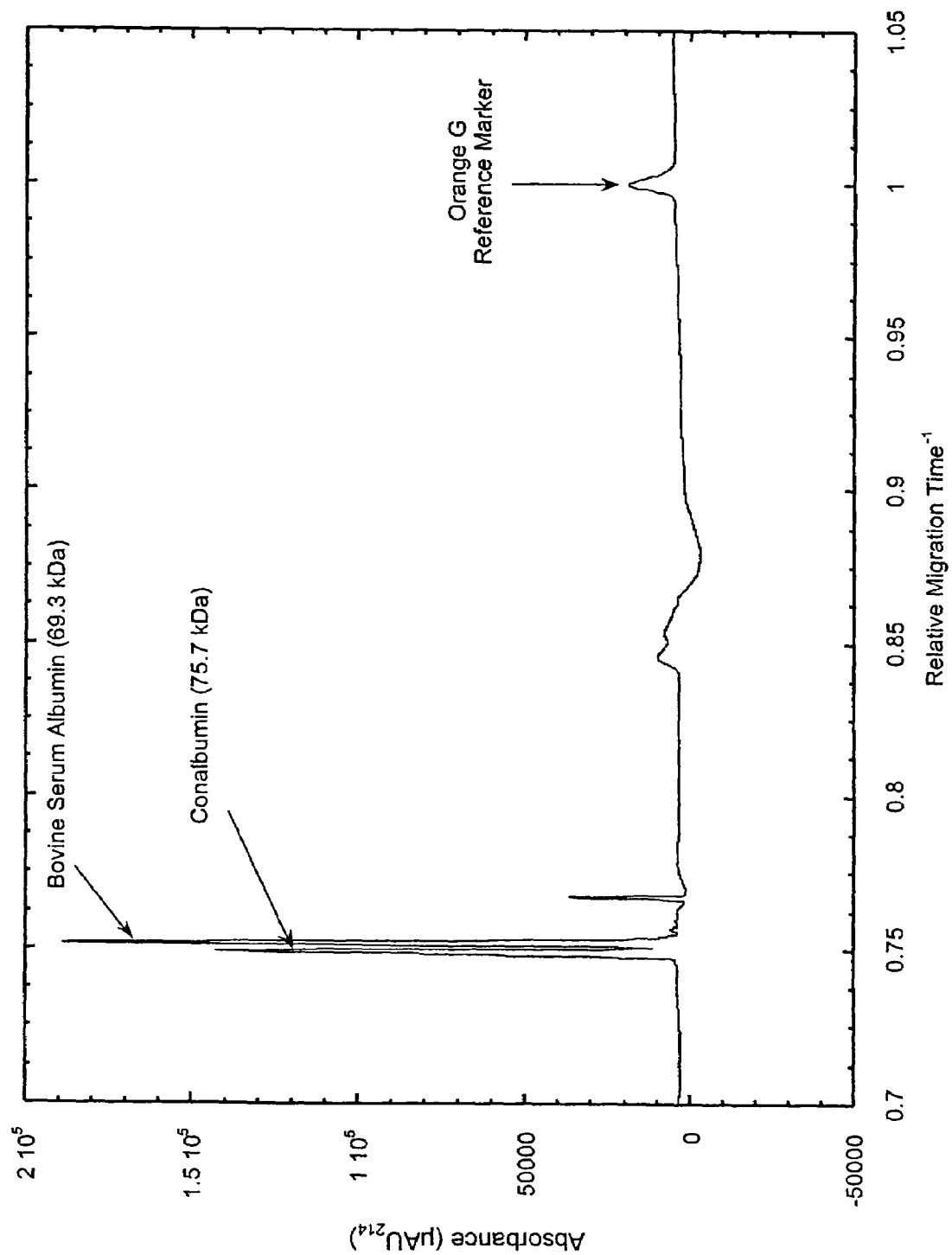
FIG. 9 is an electropherogram of a fraction (fraction F) obtained from the separation by CIEF shown in FIG. 7.
Figure 10:
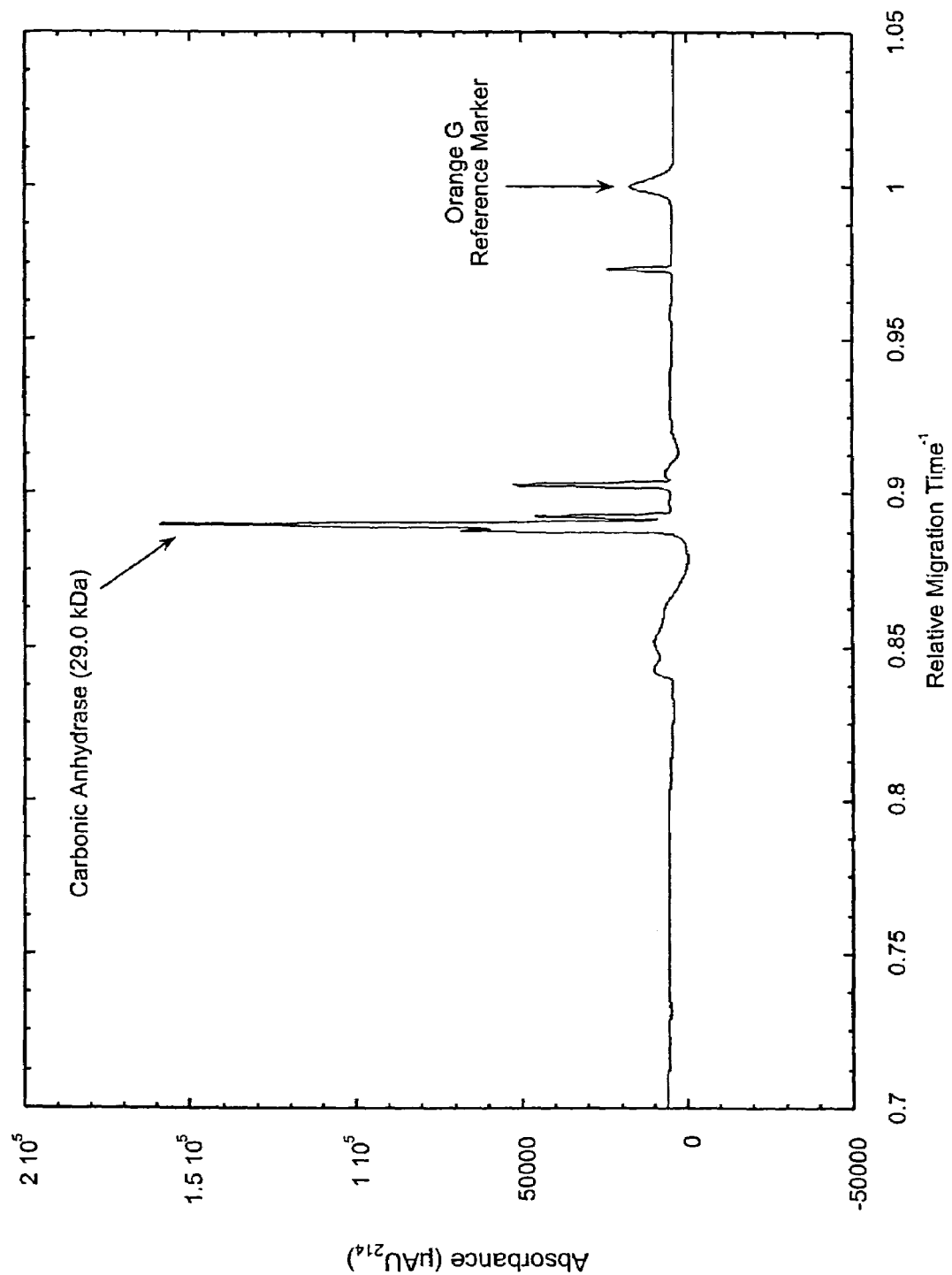
FIG. 10 is an electropherogram of a fraction (fraction G) obtained from the separation by CIEF shown in FIG. 7.
Figure 11A:
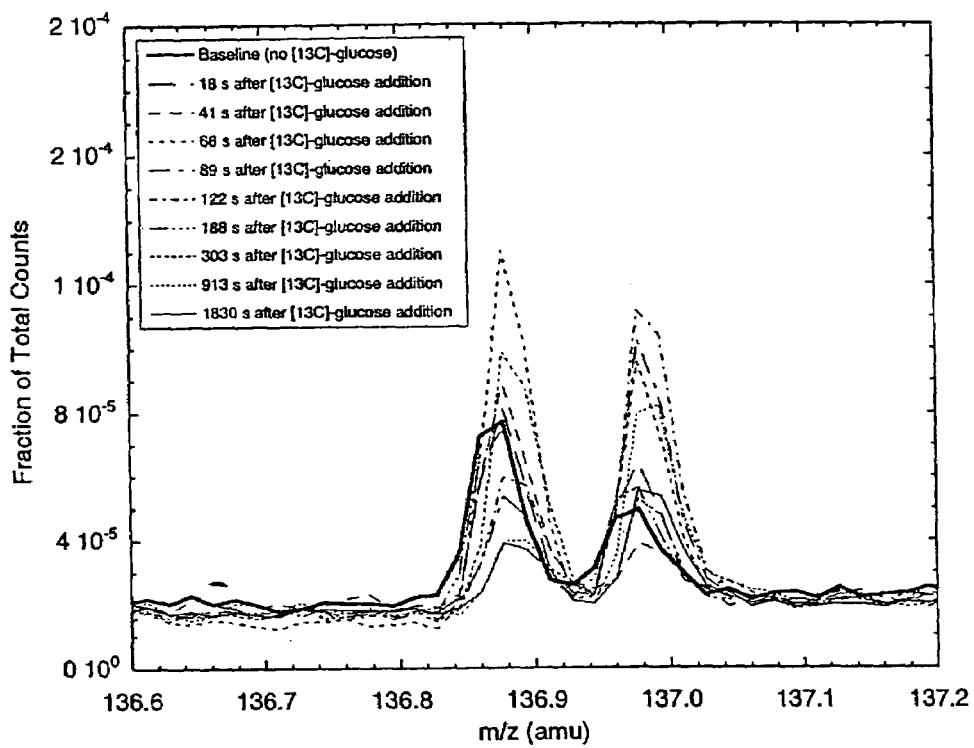
FIG. 11 shows (A) a section of the mass spectrum around 136.88 amu; (B) a similar section of the mass spectrum exactly 6.02 amu higher, corresponding to the position where the $[^{13}C]_6$-metabolite peak should exist; (C) the ratio of the counts at 142.90 to that at 136.88 amu positions in the mass spectrum, corresponding to the six carbon $^{13}C/^{12}C$ metabolite ratio; and (D) the metabolic flux, determined by curve fit to the change in the $^{13}C/^{12}C$ ratio over time at 136.88 amu.
Figure 11B:
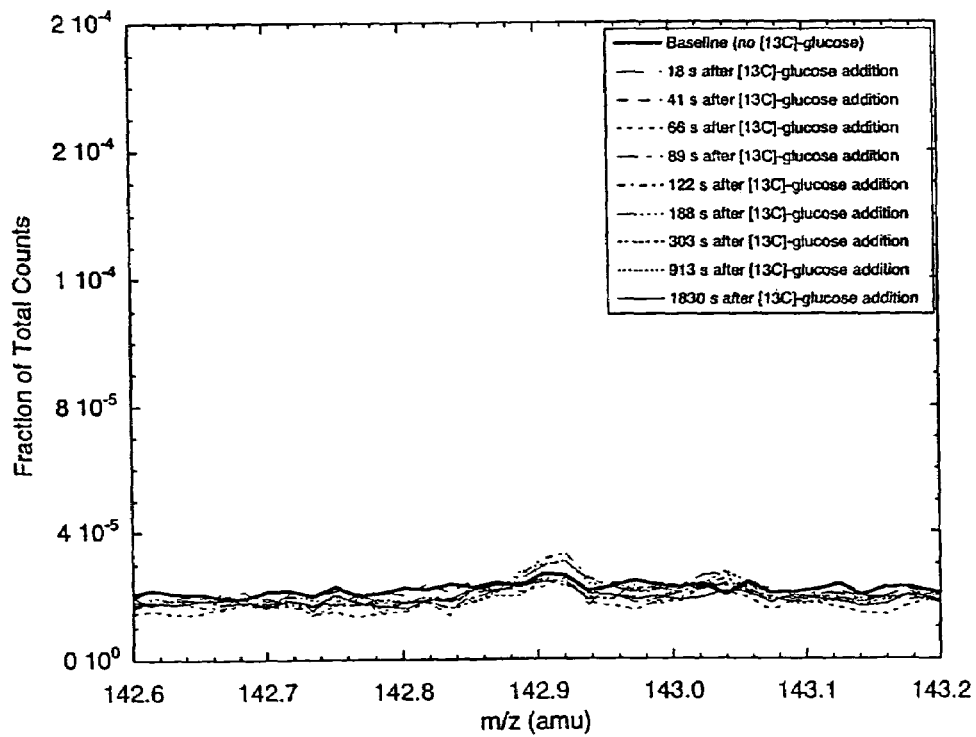
Figure 11C:
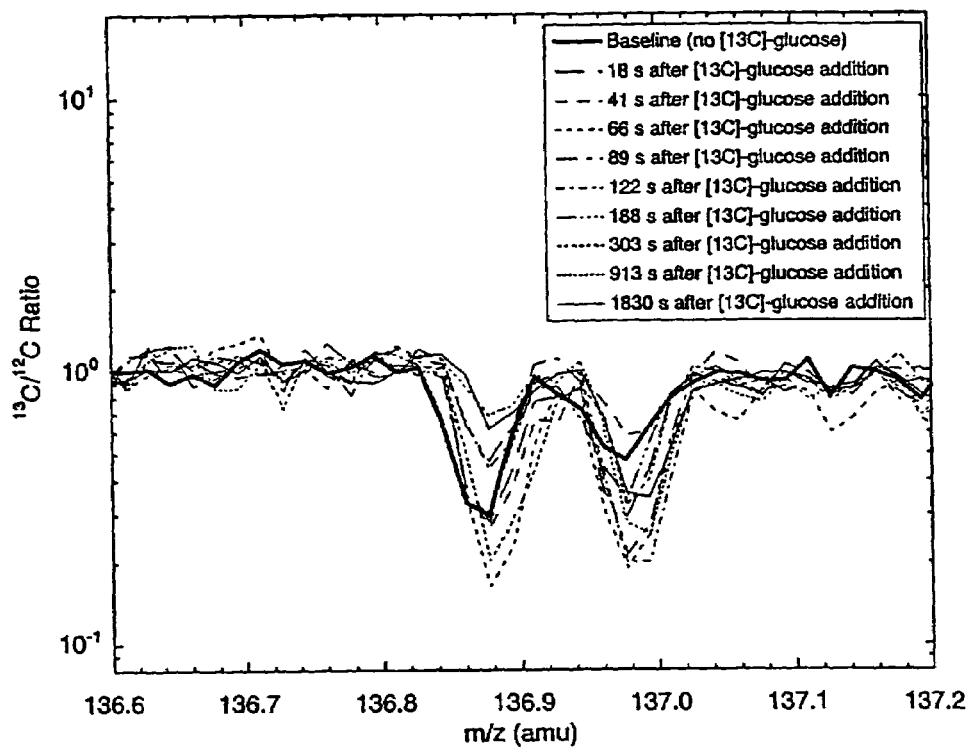
Figure 11D:
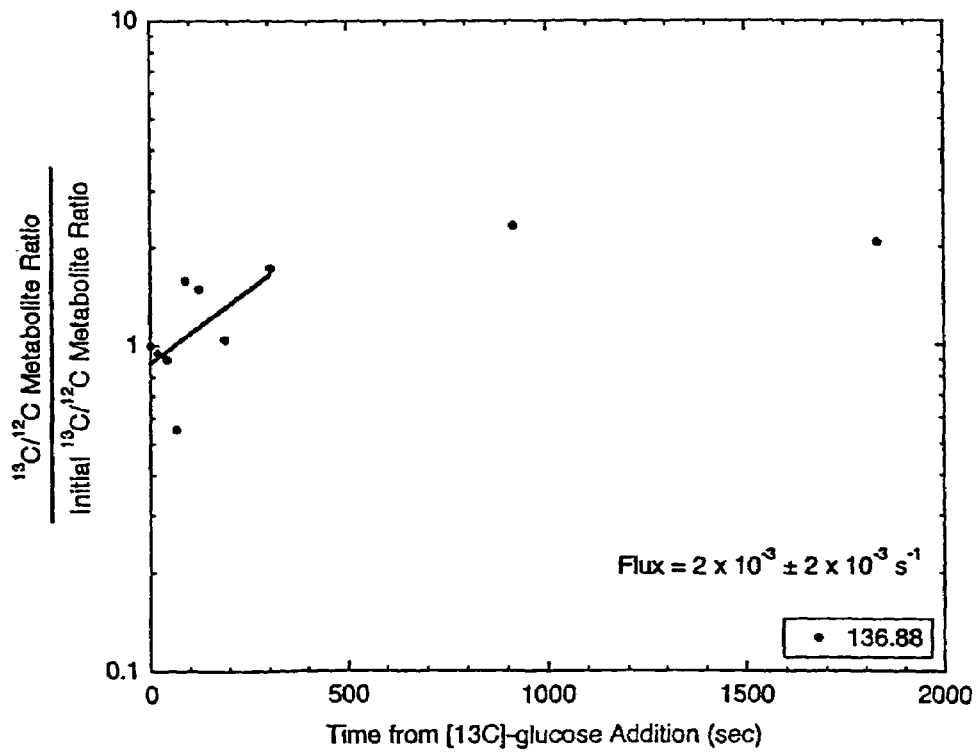
Figure 12A:
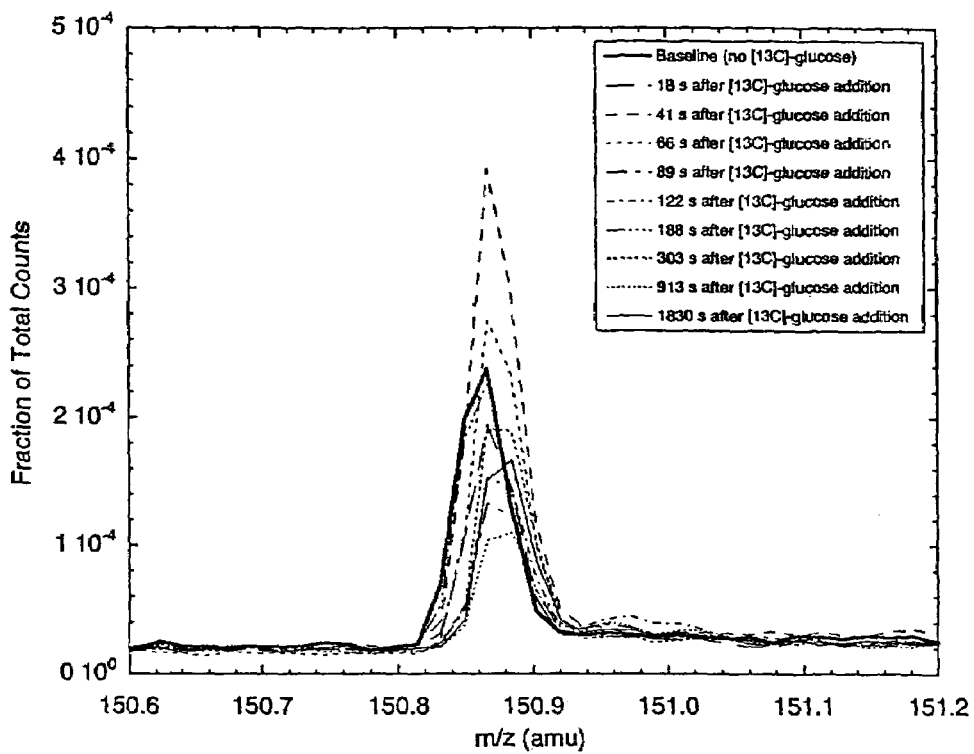
FIG. 12 shows (A) a section of the mass spectrum around 150.87 amu; (B) a similar section of the mass spectrum exactly 6.02 amu higher, corresponding to the position where the $[^{13}C]_6$-metabolite peak should exist; (C) the ratio of the counts at 156.89 to that at 150.88 amu positions in the mass spectrum, corresponding to the six carbon $^{13}C/^{12}C$ metabolite ratio; and (D) the metabolic flux, determined by curve fit to the change in the $^{13}C/^{12}C$ ratio over time at 150.87 amu.
Figure 12B:
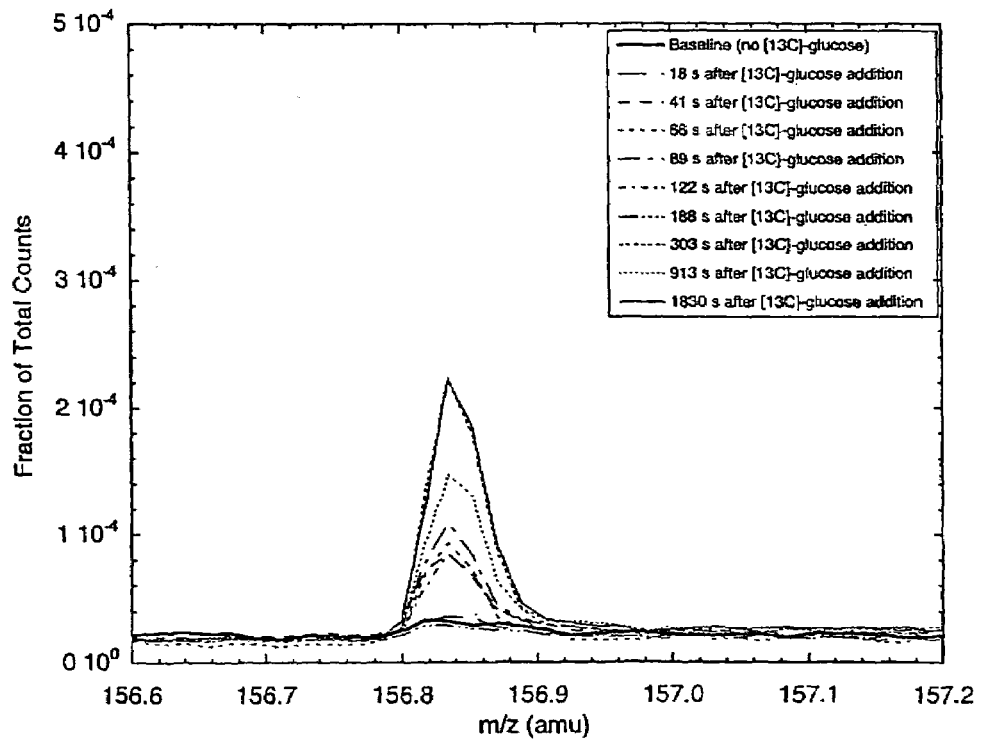
Figure 12C:
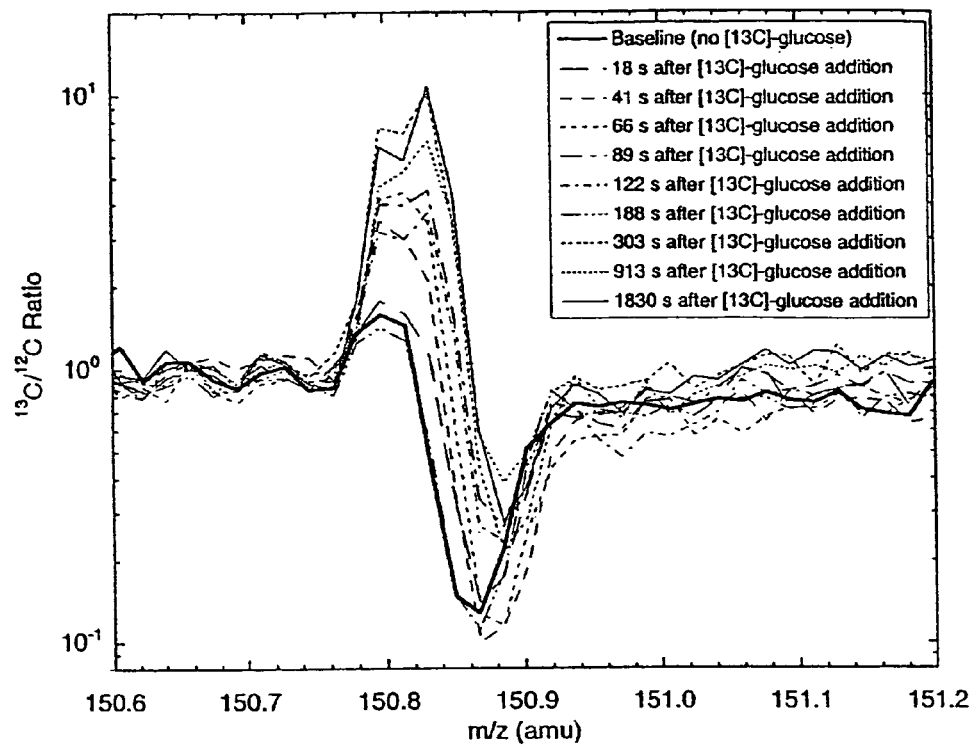
Figure 12D:
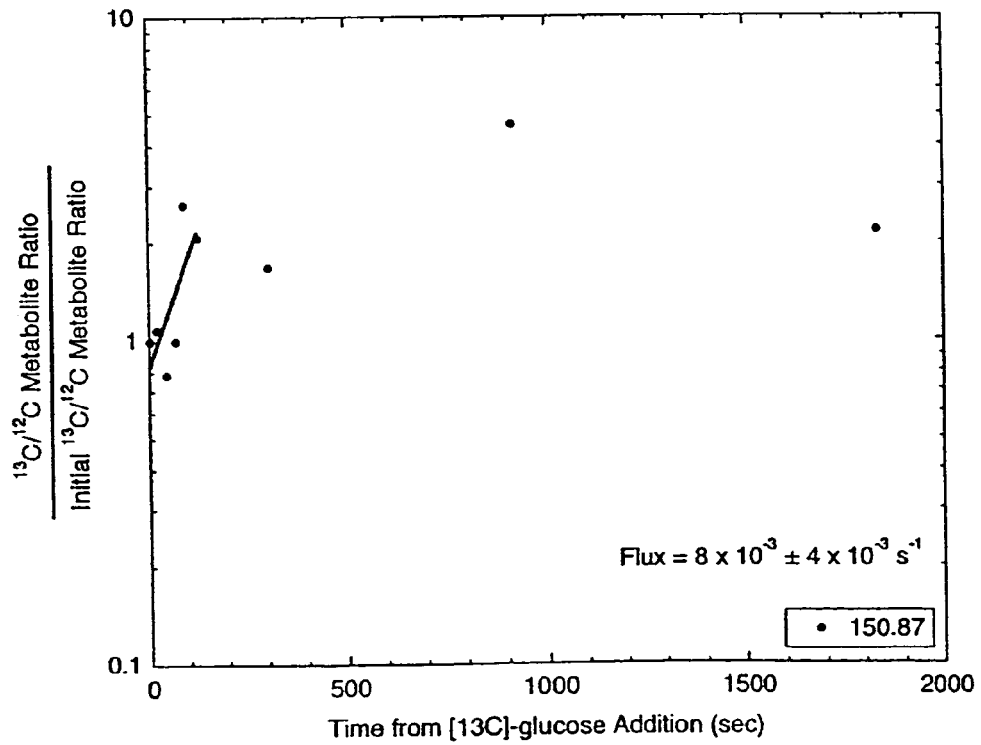
Figure 13A:
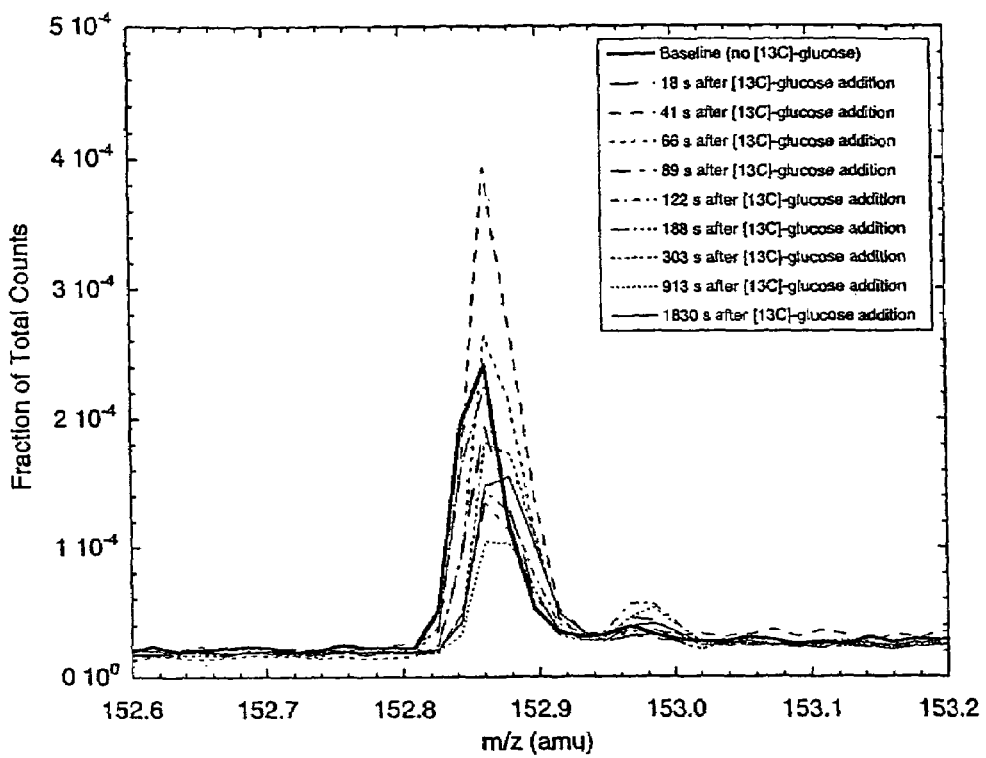
FIG. 13 shows (A) a section of the mass spectrum around 152.88 amu; (B) a similar section of the mass spectrum exactly 6.02 amu higher, corresponding to the position where the $[^{13}C]_6$-metabolite peak should exist; (C) the ratio of the counts at 152.90 to that at 152.88 amu positions in the mass spectrum, corresponding to the six carbon $^{13}C/^{12}C$ metabolite ratio; and (D) the metabolic flux, determined by curve fit to the change in the $^{13}C/^{12}C$ ratio over time at 152.88 amu.
Figure 13B:
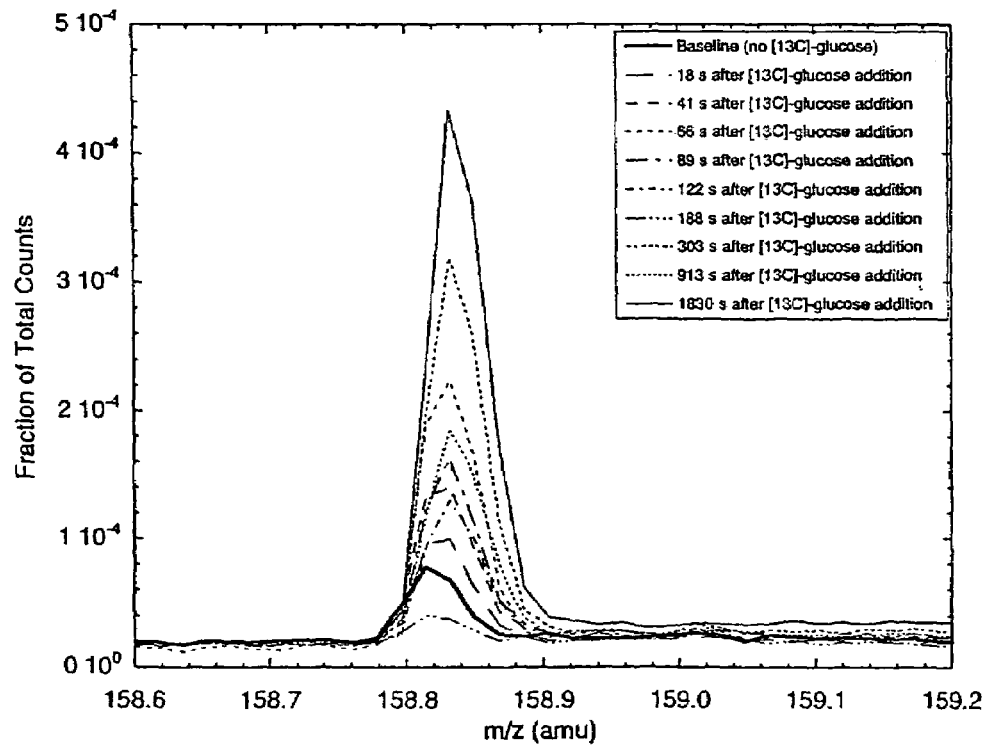
Figure 13C:
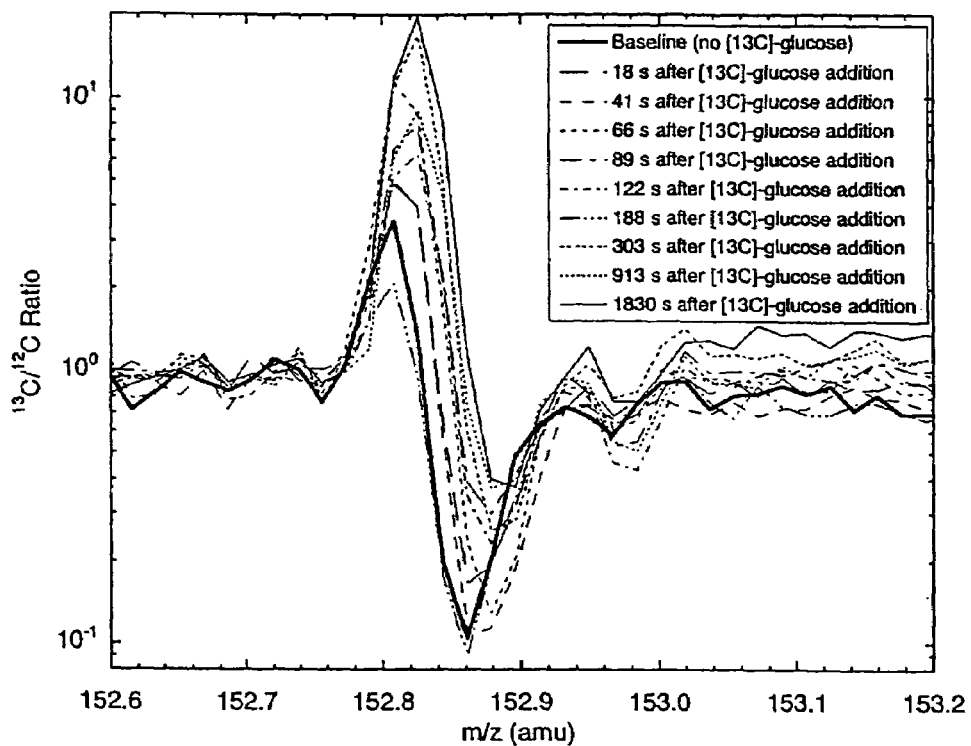
Figure 13D:
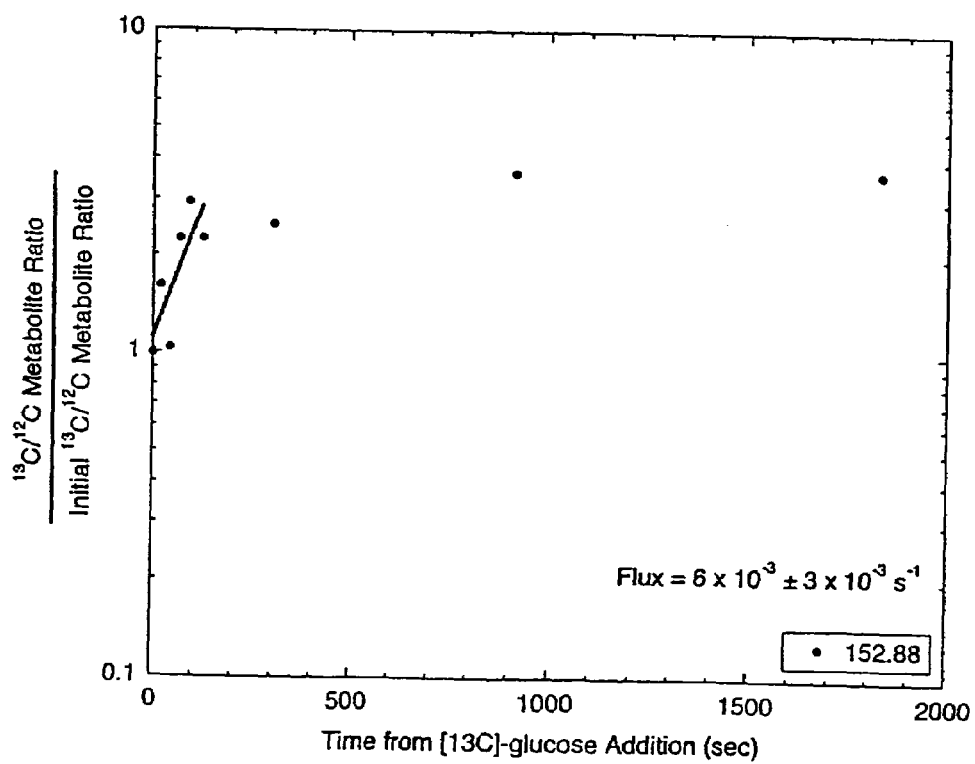
Figure 14A:
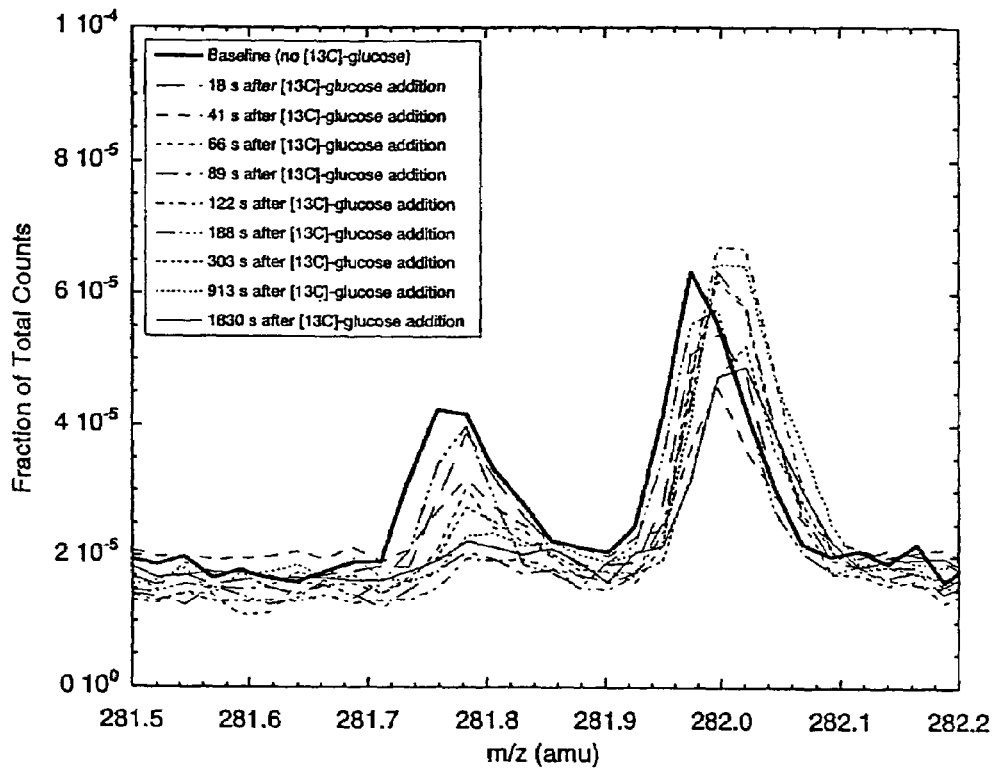
FIG. 14 shows (A) a section of the mass spectrum around 281.77 amu; (B) a similar section of the mass spectrum exactly 6.02 amu higher, corresponding to the position where the $[^{13}C]_6$-metabolite peak should exist; (C) the ratio of the counts at 287.79 to that at 281.77 amu positions in the mass spectrum, corresponding to the six carbon $^{13}C/^{12}C$ metabolite ratio and (D) the metabolic flux, determined by curve fit to the change in the $^{13}C/^{12}C$ ratio over time at 281.77 amu.
Figure 14B:
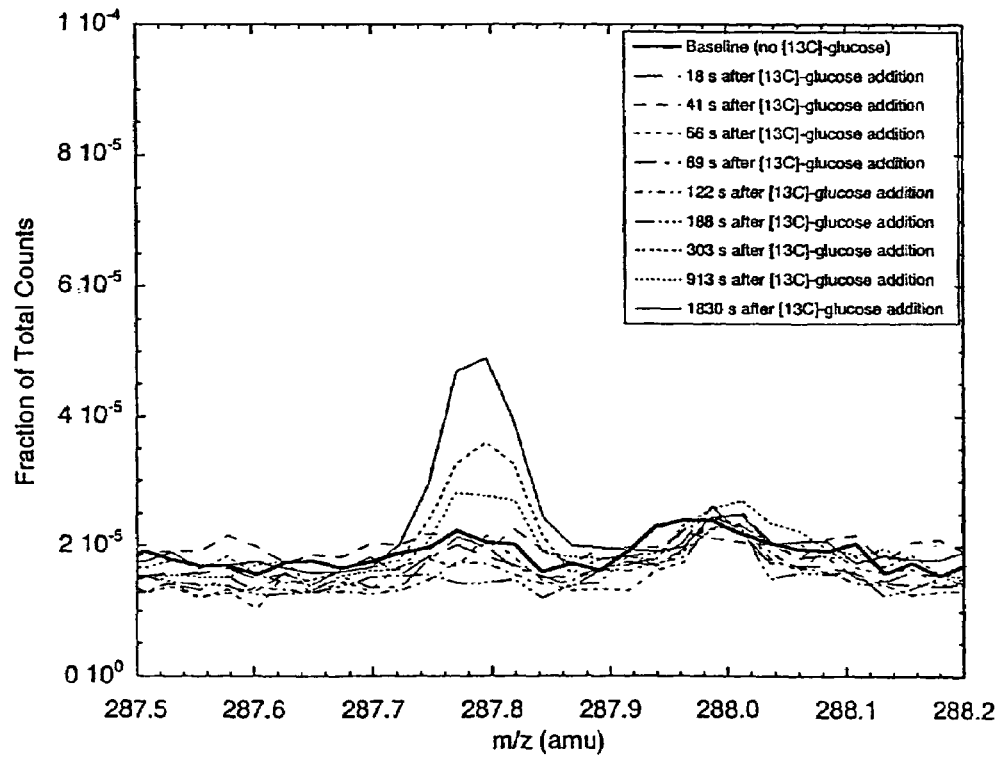
Figure 14C:
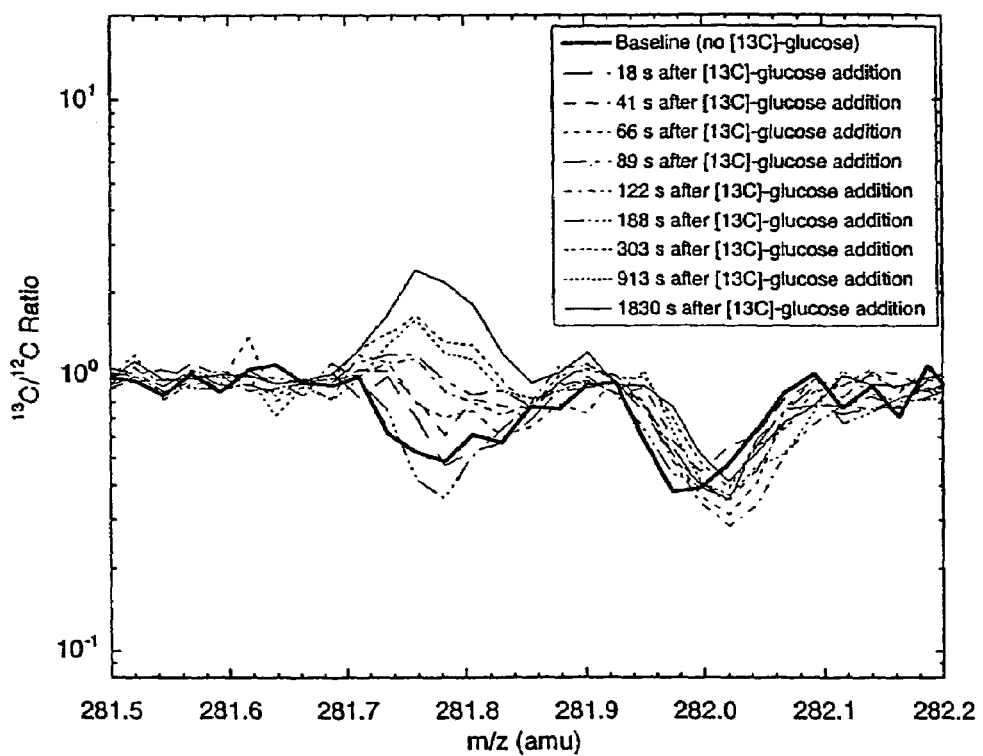
Figure 14D:
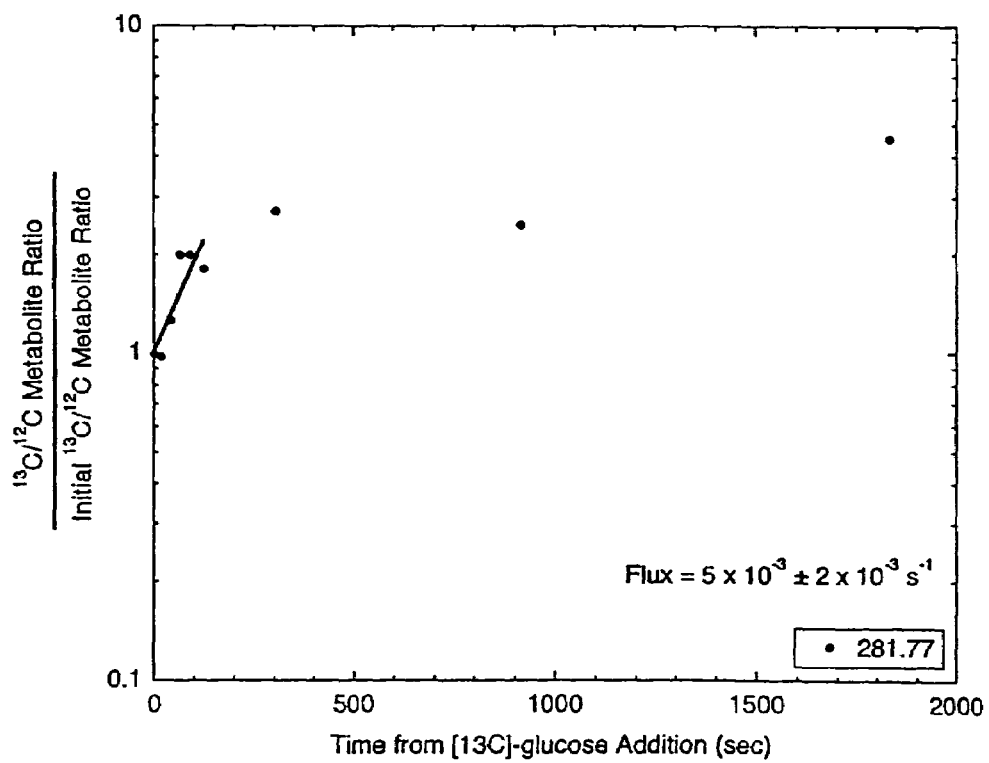
Figure 15A:
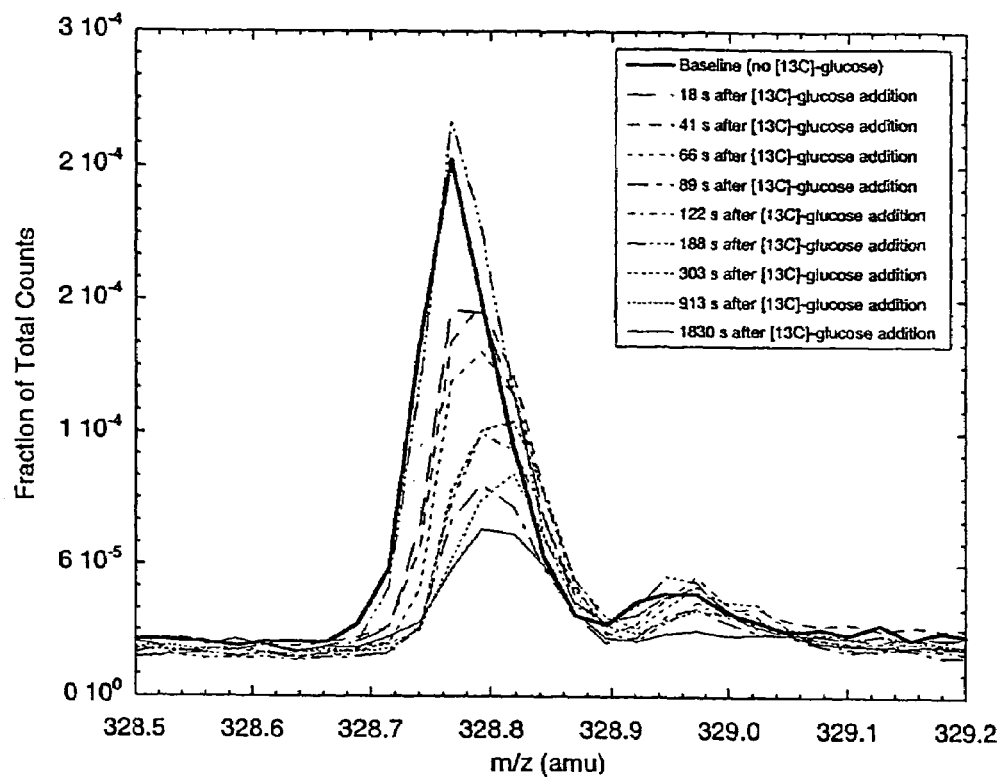
FIG. 15 shows (A) a section of the mass spectrum around 328.76 amu; (B) a similar section of the mass spectrum exactly 6.02 amu higher, corresponding to the position where the $[^{13}C]_6$-metabolite peak should exist; (C) the ratio of the counts at 334.78 to that at 328.76 amu positions in the mass spectrum, corresponding to the six carbon $^{13}C/^{12}C$ metabolite ratio; and (D) the metabolic flux, determined by curve fit to the change in the $^{13}C/^{12}C$ ratio over time at 328.76 amu.
Figure 15B:
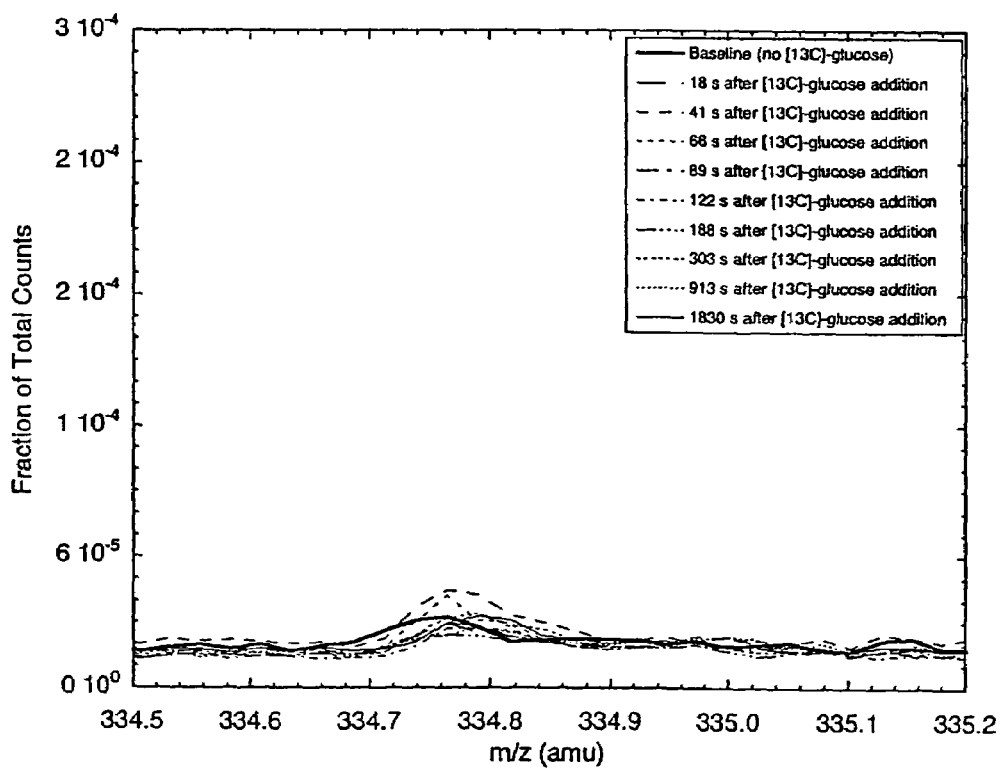
Figure 15C:
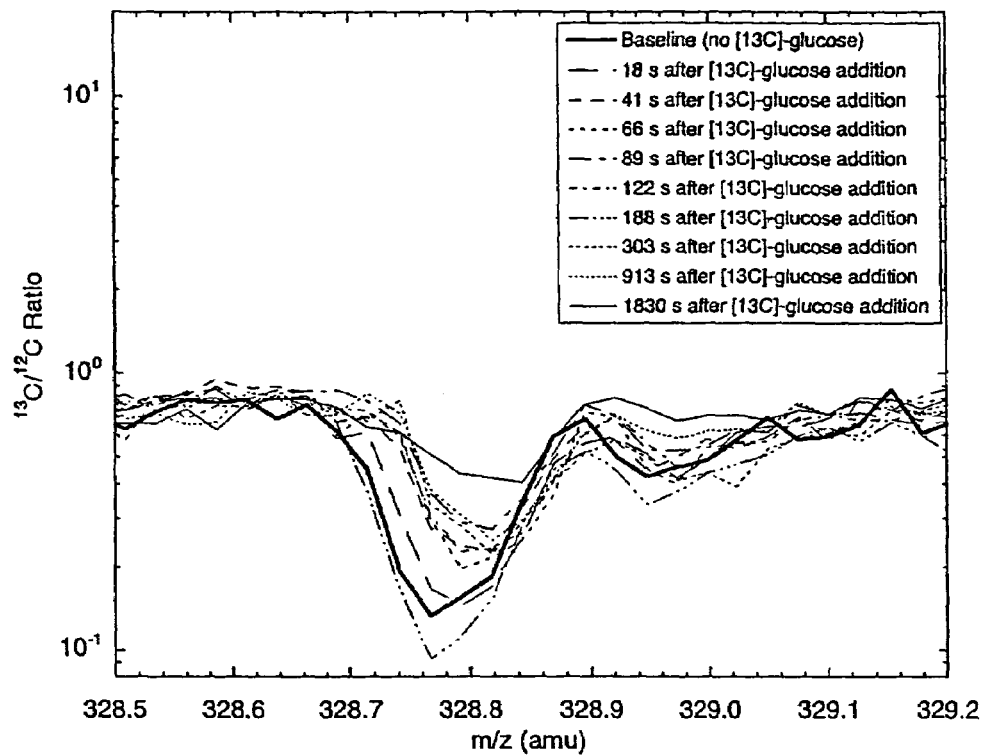
Figure 15D:
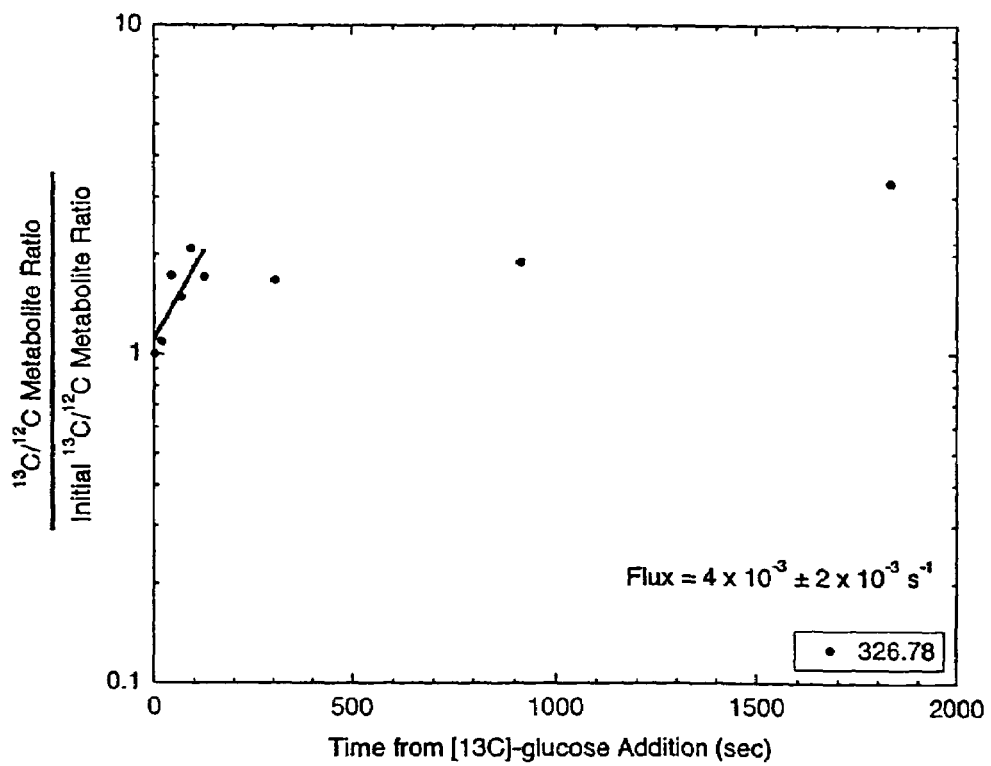
Figure 16A:
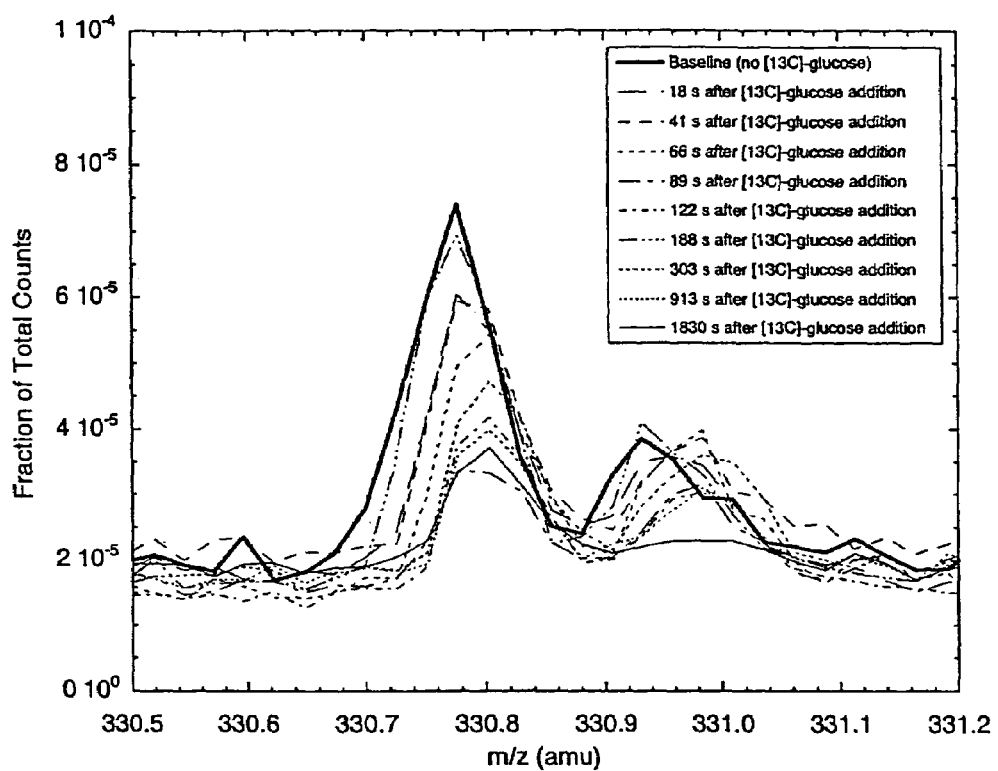
FIG. 16 shows (A) a section of the mass spectrum around 330.76 amu; (B) a similar section of the mass spectrum exactly 6.02 amu higher, corresponding to the position where the $[^{13}C]_6$-metabolite peak should exist; (C) the ratio of the counts at 336.78 to that at 330.76 amu positions in the mass spectrum, corresponding to the six carbon $^{13}C/^{12}C$ metabolite ratio; and (D) the metabolic flux, determined by curve fit to the change in the $^{13}C/^{12}C$ ratio over time at 330.76 amu.
Figure 16B:
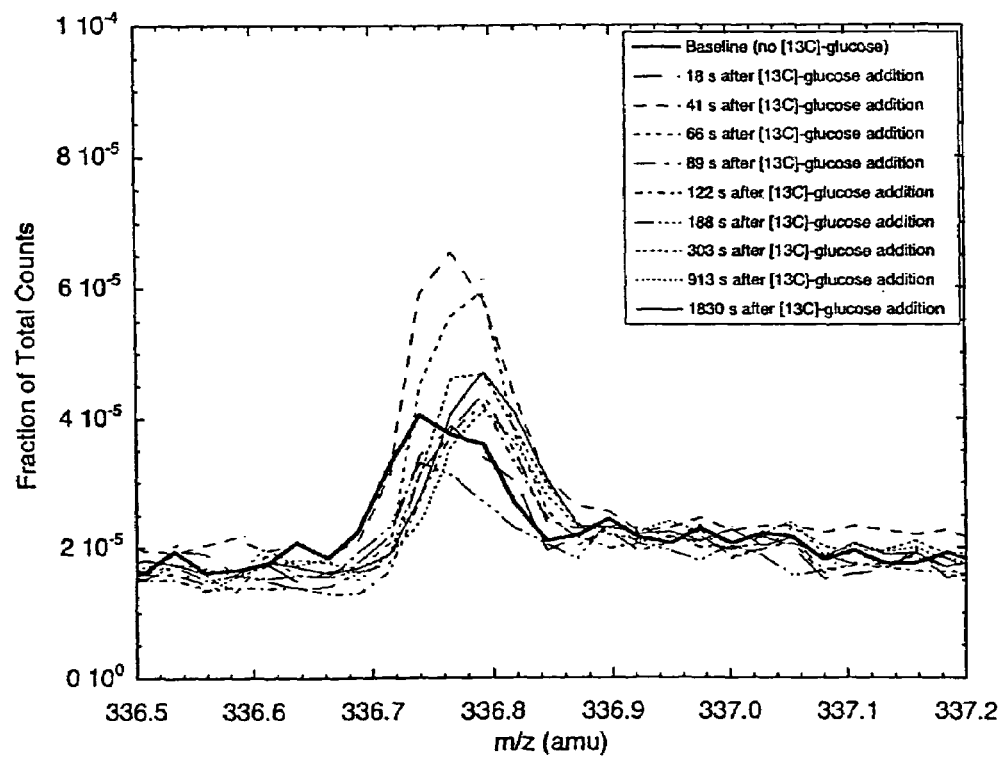
Figure 16C:
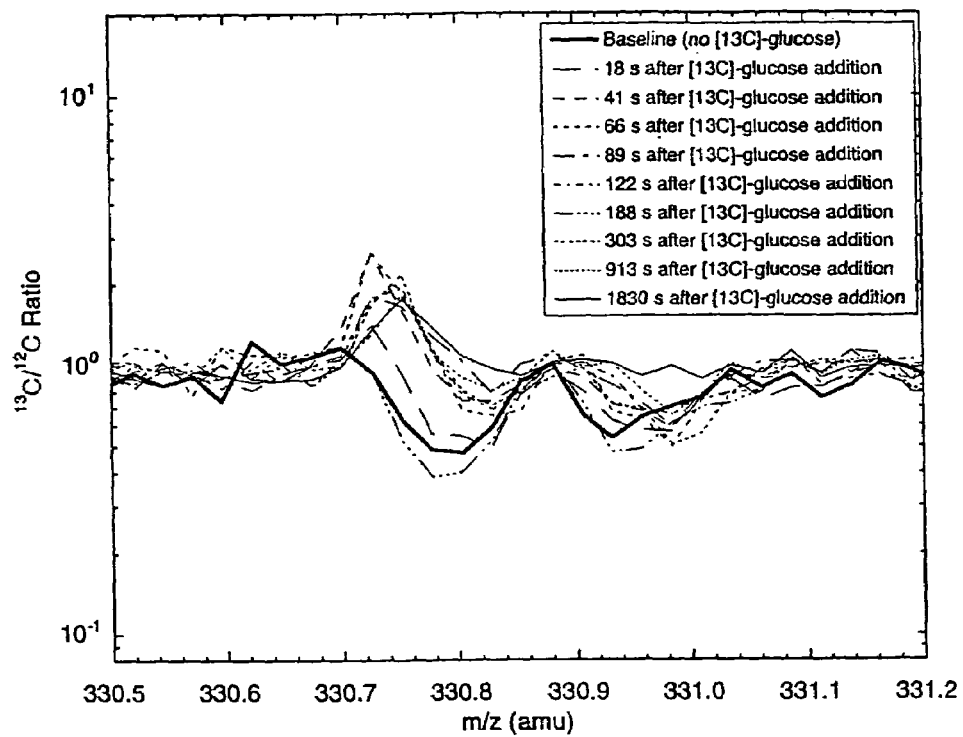
Figure 16D:
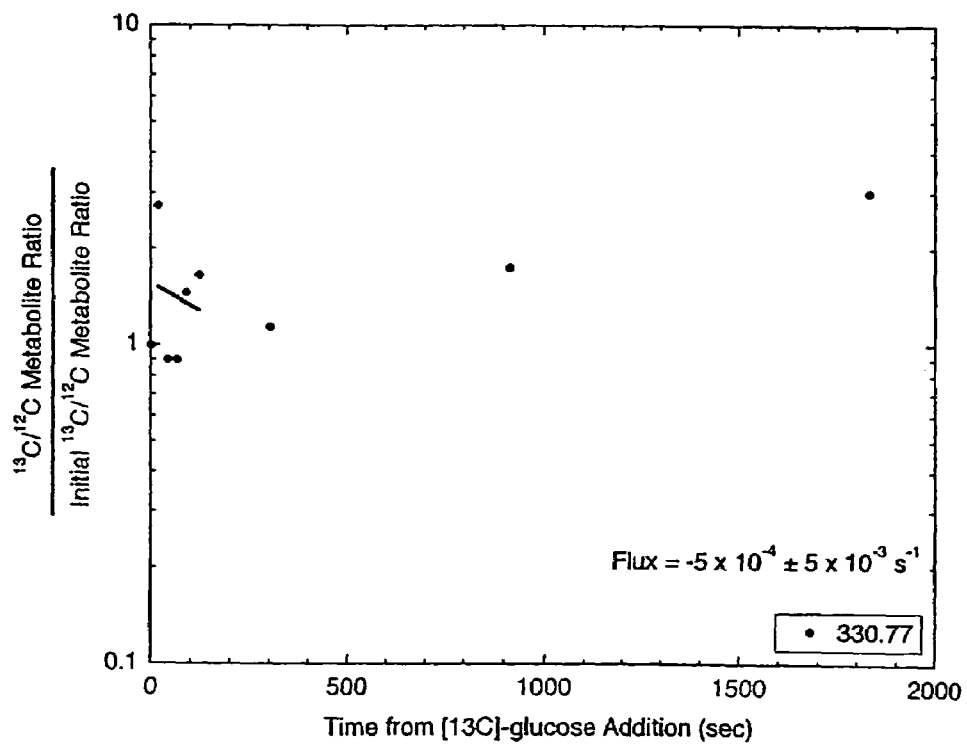
Figure 17A:
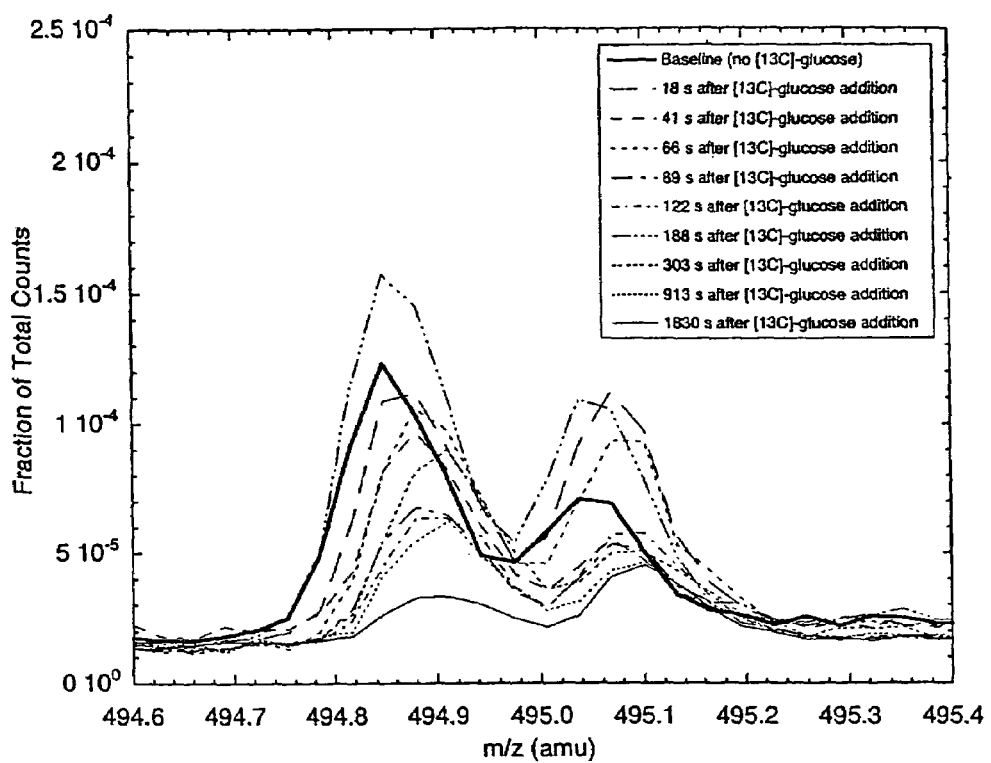
FIG. 17 shows (A) a section of the mass spectrum around 494.84 amu; (B) a similar section of the mass spectrum exactly 6.02 amu higher, corresponding to the position where the $[^{13}C]_6$-metabolite peak should exist; (C) the ratio of the counts at 500.86 to that at 494.84 amu positions in the mass spectrum, corresponding to the six carbon $^{13}C/^{12}C$ metabolite ratio; and (D) the metabolic flux, determined by curve fit to the change in the $^{13}C/^{12}C$ ratio overtime at 494.82 amu.
Figure 17B:
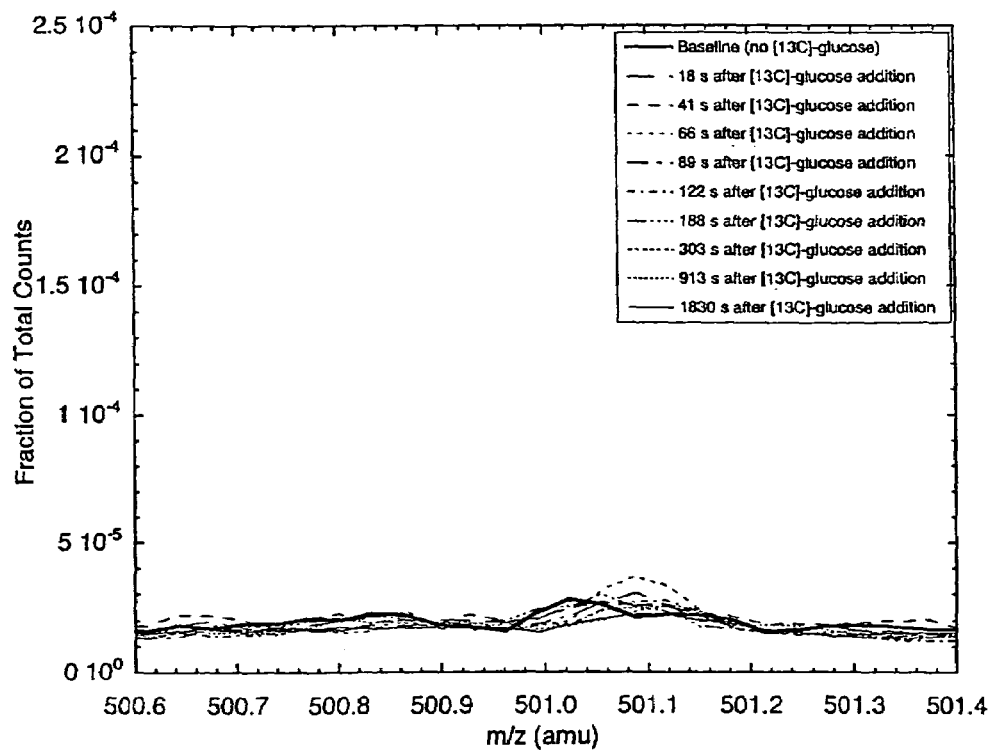
Figure 17C:
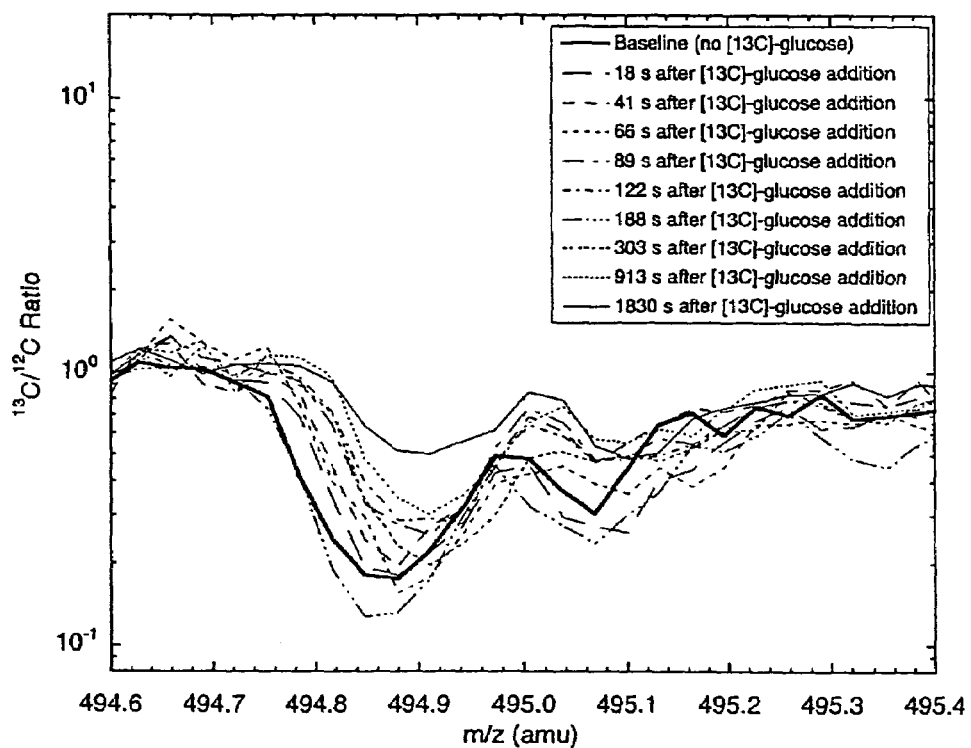
Figure 17D:
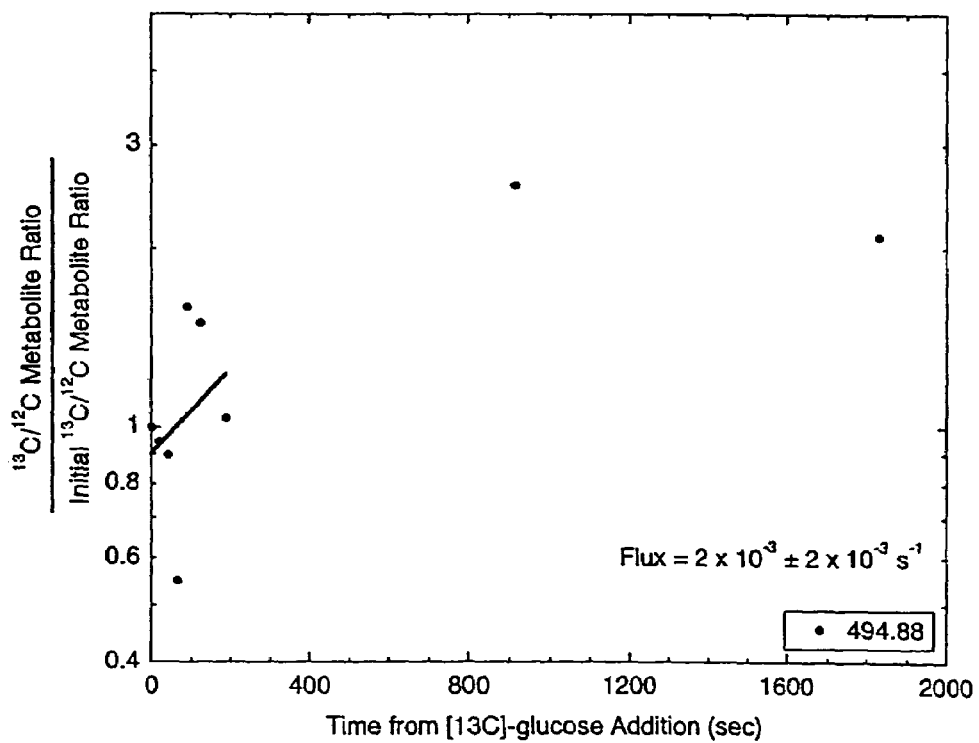
Figure 18A:
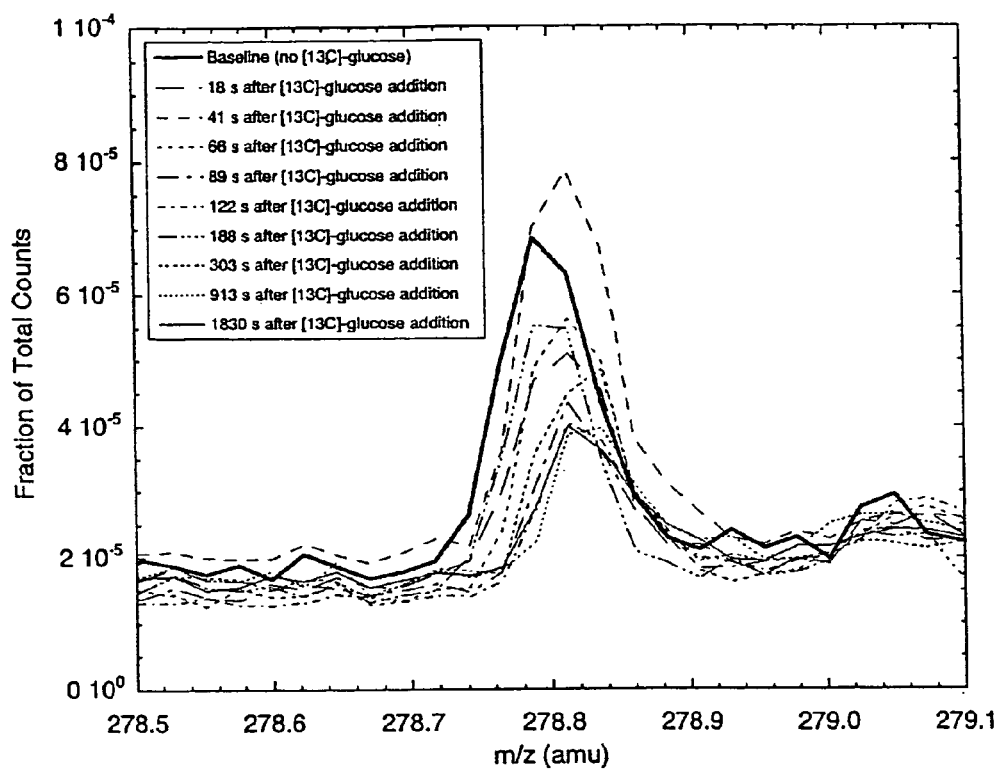
FIG. 18 shows (A) a section of the mass spectrum around 278.80 amu; (B) a similar section of the mass spectrum exactly 5.02 amu higher, corresponding to the position where the $[^{13}C]_5$-metabolite peak should exist; (C) the ratio of the counts at 283.82 to that at 278.80 amu positions in the mass spectrum, corresponding to the five carbon $^{13}C/^{12}C$ metabolite ratio; and (D) the metabolic flux, determined by curve fit to the change in the $^{13}C/^{12}C$ ratio over time at 278.80 amu.
Figure 18B:
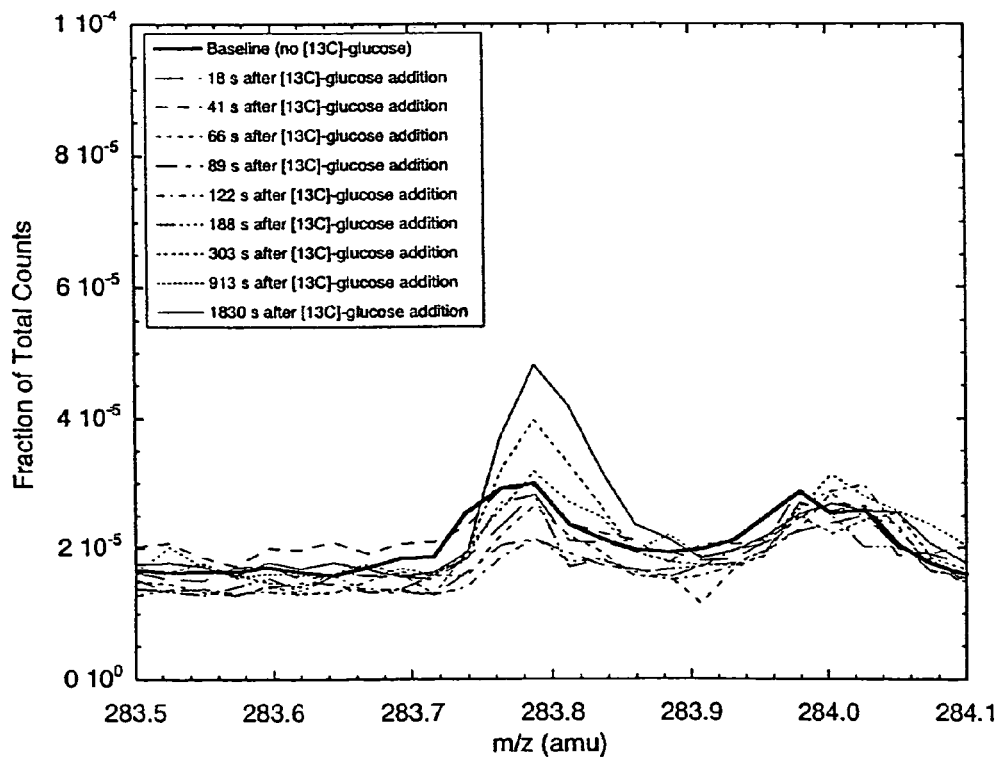
Figure 18C:
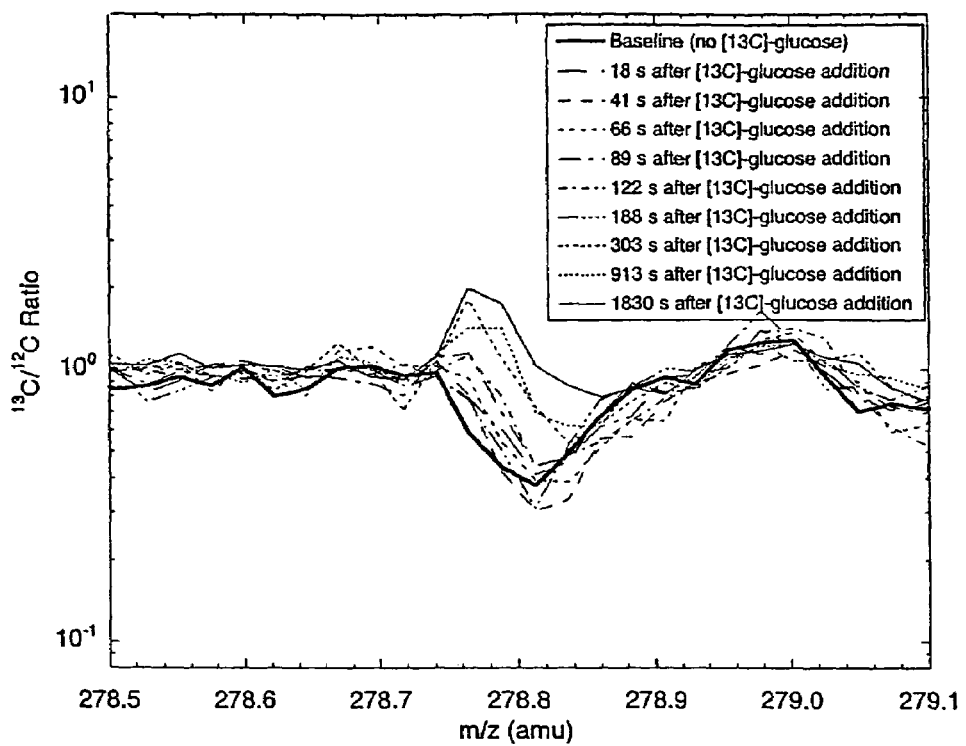
Figure 18D:
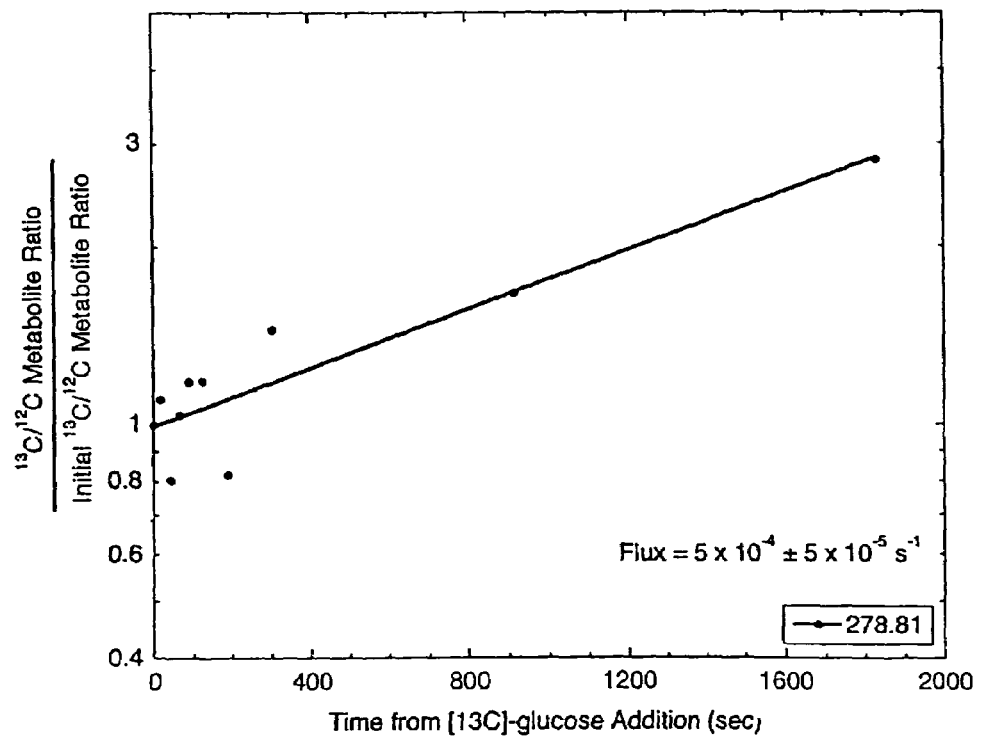
Figure 19A:
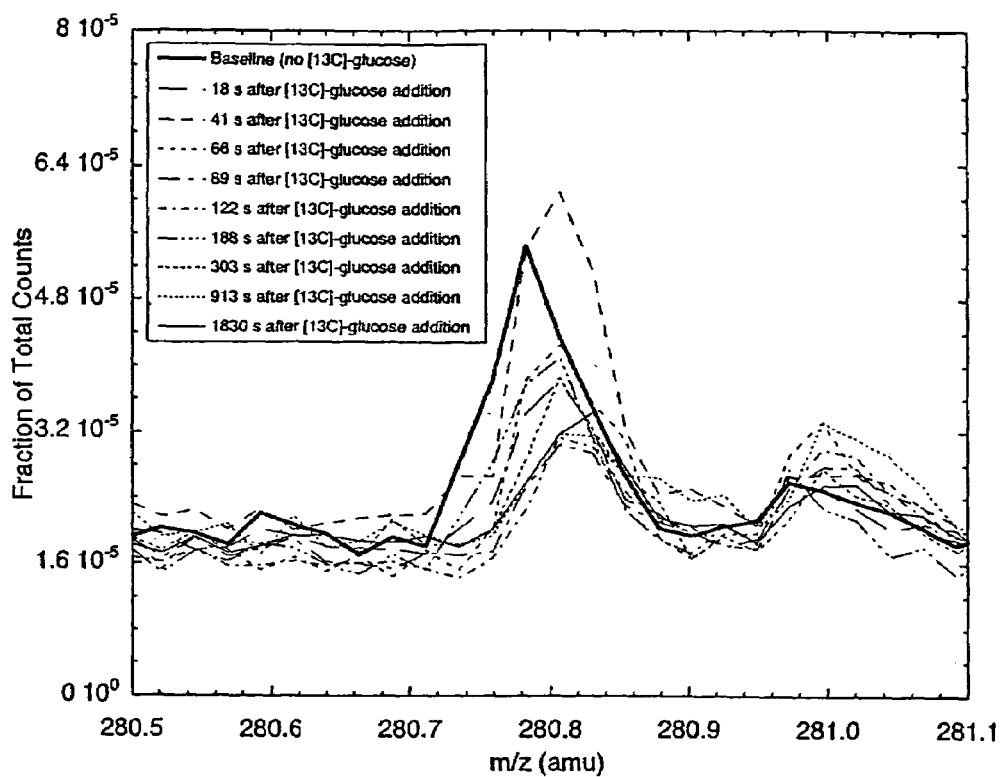
FIG. 19 shows (A) a section of the mass spectrum around 280.80 amu; (B) a similar section of the mass spectrum exactly 5.02 amu higher, corresponding to the position where the $[^{13}C]_5$-metabolite peak should exist; (C) the ratio of the counts at 285.82 to that at 280.8 amu positions in the mass spectrum, corresponding to the five carbon $^{13}C/^{12}C$ metabolite ratio; and (D) the metabolic flux, determined by cure fit to the change in the $^{13}C/^{12}C$ ratio over time at 280.80 amu.
Figure 19B:
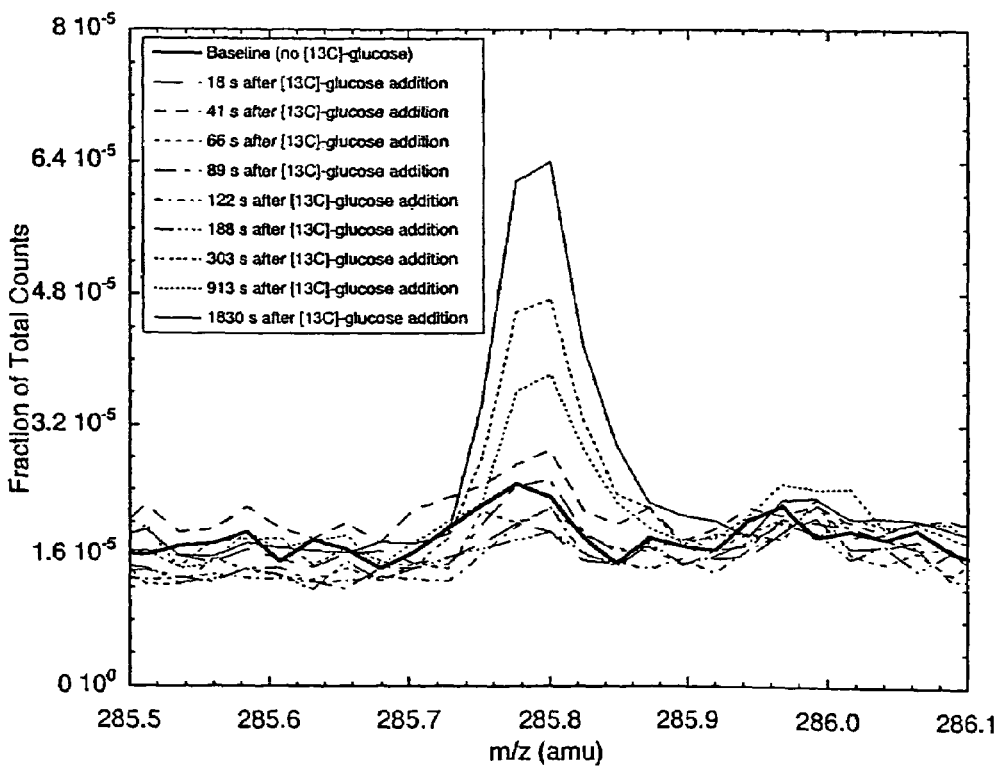
Figure 19C:
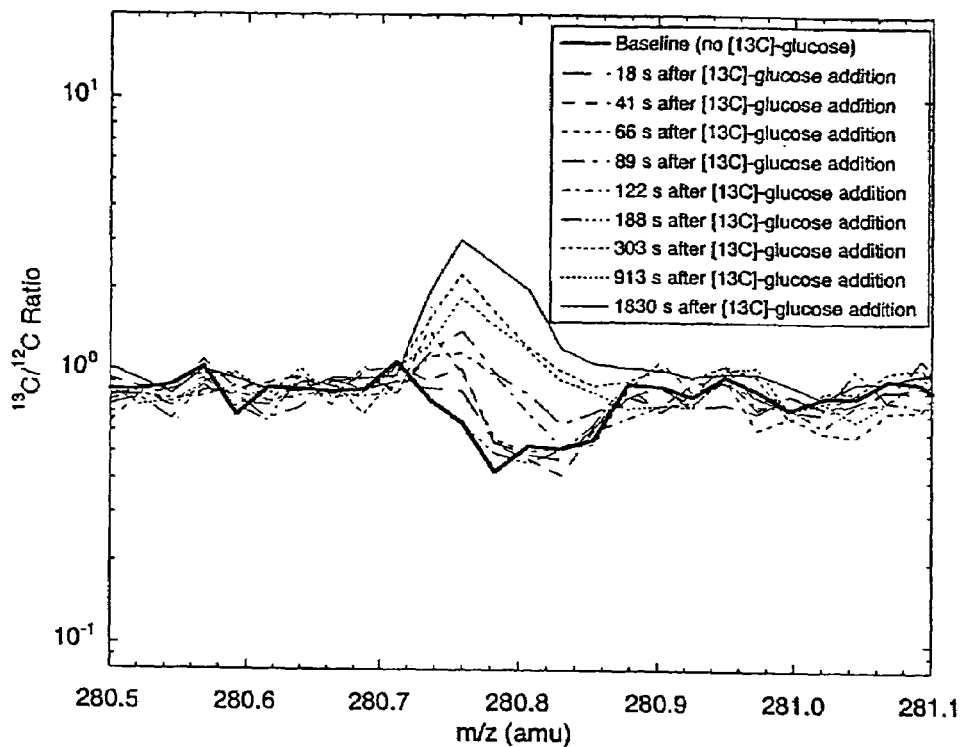
Figure 19D:
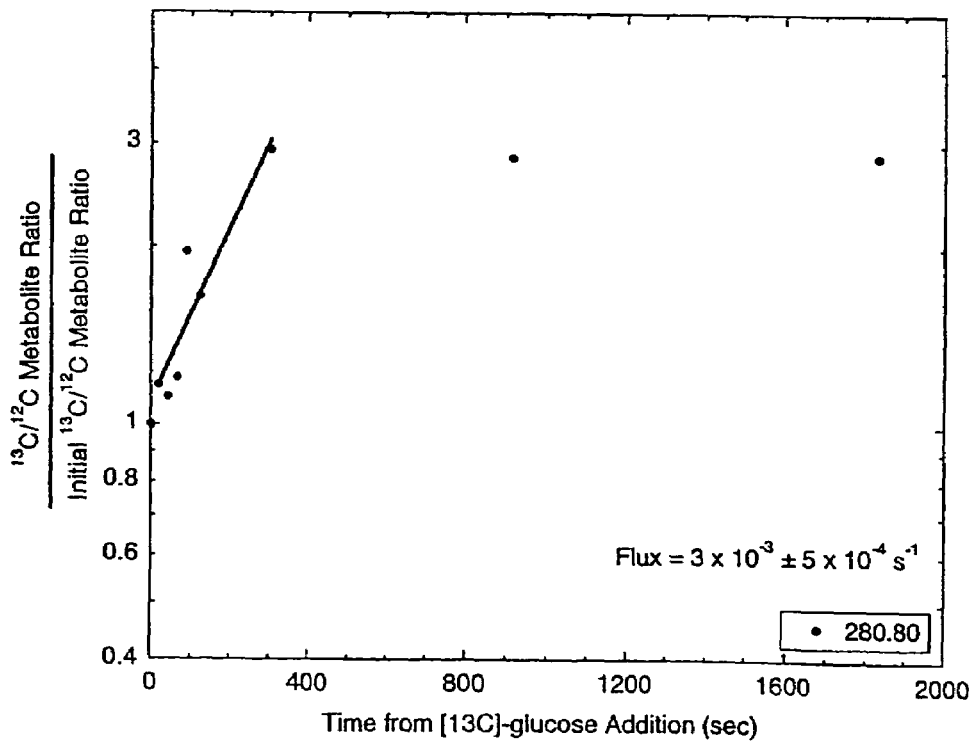

The resulting electropherograms showed no detectable protein in any cIEF fraction except fractions F (FIG. 9) and G (FIG. 10). The molecular weight of the two proteins seen in fraction F (FIG. 9) correspond to that of bovine serum albumin and conalbumin (Table 2). The molecular weight of the protein seen in fraction G (FIG. 10) corresponded to that of carbonic anhydrase (Table 1). It is observed that the second cGE dimension was necessary to fully resolve bovine serum albumin from conalbumin, which were not resolved by a single cIEF mode (Example 3).

EXAMPLE 5

Role of Metabolism in Autism

The methods of the invention can be utilized to ascertain whether various diseases have a metabolic basis and even to pinpoint the metabolic basis. As a specific example, the methods and apparatus of the invention can be used to establish whether autism (or the severity of autistic symptoms) results from dietary factors, determine the mechanism through which diet may influence autism, and establish a simple $^{13}C$ metabolic assay to facilitate diagnosis of such dietary influences.

Elevated exogenous peptides have been found in the blood, urine, and cerebral spinal fluids of large numbers of autistic children (Reichelt, K. et al., *J. Appl. Nutrition*, 42:1-11 (1990); Reichelt, K. et al., *Developmental Brain Dysfunction*, 7:71-85 (1994); Reichelt, K. et al., *Brain Dysfunction*, 4:308-319 (1991); Gillberg, C., "The role of endogenous opioids in autism and possible relationships to clinical features," in Wing, L. (ed.), *Aspects of Autism: Biological Research*, pp. 31-37, Gaskell, London, (1988); Shattock, P., A., et al., *Brain Dysfunction*, 3:328-345 (1990)). Precedents from celiac disease, and a number of clinical case studies documenting significant patient improvements on grain and dairy dietary restrictions, have led to three hypotheses regarding dietary effects on autism. (See, e.g., Fukudome, S. and Yoshikawa, M., *FEBS Lett.*, 296:107-111 (1992); Fukudome, S. and Yoshikawa, M., *FEBS Lett.* 316:17-19 (1993); Reichelt, K. et al., *J. Appl. Nutrition*, 42:1-11 (1990); Reichelt, K. et al., *Developmental Brain Dysfunction*, 7:71-85 (1994); Reichelt, K. et al., *Brain Dysfunction*, 4:308-319 (1991); Shattock, P., A., et al., *Brain Dysfunction*, 3:328-345 (1990); Lewis, L. S., "Dietary intervention for the treatment of autism: Why implement a gluten and casein free diet?," in: *Biological Treatments for, Autism and PDD*, pp 196-226, (Sham, 1998); Serousi, K., "Following a different road. A child's documented recovery from autism," in: *Biological Treatments for Autism and PDD*, pp 265-289, (Shaw,1998)).

The first theory, suggested by Lewis, is that a mild form of celiac disease may exist in many, if not all, autistic children, leading to peptide malabsorption from the gut and associated neurological symptoms (Lewis, L. S., "Dietary intervention for the treatment of autism: Why implement a gluten and casein free diet?," in: *Biological Treatments for Autism and PDD*, pp 196-226, (Shaw, 1998)). Shaw has proposed a second theory, namely that the exogenous peptides observed are a consequence of intestinal yeast infections, which are stimulated by the carbohydrate content of grains and milk (Shaw, W., et al., "Increased excretion of analogs of Krebs cycle metabolites and arabinose in two brothers with autistic features," *Clin. Chem.*, 41:1094-1104 (1995); and Shaw, W., "Organic acid testing, byproducts of yeast and their relationship to autism," in: *Biological Treatments for Autism and PDD, pp.* 31-65, (Shaw, 1998)). Intestinal yeast may directly produce exogenous peptides as secondary metabolites or the peptides may form in the blood indirectly through crosslinking caused by the high levels of reducing sugars they produce. Based on clinical data concerning the efficacy of secretin and peptidase supplementation in the diet of autistic children, Shaw has proposed a third possible mechanism, suggesting that digestive enzymes may not be functioning properly in autistic patients (Shaw, W., "Abnormalities of the digestive system," in: *Biological Treatments for Autism and PDD*, pp. 124-138, (Shaw, 1998)).

How the methods of the invention can be used to distinguish between these theories can be seen from a two compartment pharmacokinetic model for peptide absorption through the gut (Notari, R. E., *Biopharmaceutics and Pharmacokinetics: An Introduction*, $2^{nd}$ ed., Marcei Dekker, N.Y., (1975)). The flux of exogenous peptides through the intestinal wall ($g_p$) can be represented by:

$$g_p = k_t(K_a C_p^i - K_b C_p^b) \tag{1}$$

where $k_t$ is the mass transport coefficient for the intestinal wall, $K_i$ and $K_b$ are the equilibrium constants for dissolution of the peptide in the intestinal wall and its concentrations in the intestine($C_p^i$) and blood $C_p^b$ respectively.

The flux of peptides through the intestinal wall competes with the rate of peptidase digestion of the peptide in the gut ($r_p$), which we represent by:

$$r_p = \frac{kE_p C_p^i}{(K_m + C_p^i)} \quad (2)$$

where k is the rate constant, Ep is the peptidase concentration in the gut and $K_m$ is the Michaelis constant.

Since typically $C_p^i >> K_m$, the peptide concentration in the blood as a function of time (t) is given by:

$$C_p^b = \frac{C_{P_o}^i}{\frac{kE_p V_i}{k_t S C_{P_o}^i} - \left(\frac{K_b}{K_i}\right) + \left(\frac{V_b}{V_i}\right)} \left\{ e^{-k_t S \left[\left(\frac{K_b}{V_b}\right) - \left(\frac{K_i}{V_i}\right)\right]t} - e^{-\frac{kE}{C_{P_o}^i}t} \right\} \quad (3)$$

where $V_i$ is the volumes contained by the intestine, $V_b$ is the distribution volume in the body, and $C_{p_o}^i$ is the initial concentration of the peptide bolus in the gut. Where $K_i \approx K_b$ and $V_i \approx V_b$, equation 3 can be approximated by:

$$C_p^b = \frac{k_t S C_{P_o}^i}{kEV_i}\left[1 - e^{-\left(\frac{kE}{C_{P_o}^i}\right)t}\right] \quad (4)$$

From equation 4 it is readily apparent that the amount of peptide crossing the intestinal wall is determined by the ratio of the permeation rate ($k_t S$) to the rate of peptide digestion in the gut ($kEV_i$).

Equally important is the rate of accumulation of peptide in the blood, which is predicted (equation 4) to depend primarily on peptidase activity in the gut (kE). Therefore, measurements of the time course of peptide accumulation in the blood can be used to identify the underlying mechanism driving maladsorption and provide significant insights for the most appropriate course of therapy. More specifically, this provides the basis for distinguishing between the two possible reasons for the appearance of exogenous peptides in the blood and urine of autistic children, namely: (1) the intestinal wall is compromised as in celiac disease, giving rise to increased peptide permeability ($k_t$), or (2) autistic children may suffer from peptidase deficiency (erg., low peptidase enzyme levels or lower than normal peptidase activity).

To identify the source of exogenous peptides arising from wheat (i.e., improper digestion and malabsorption or microbial stimulation) autistic children (and t control group) are fed a mixture of $^{13}$C-enriched and normal wheat flour. Exogenous peptides are identified from blood plasma and urine of autistic and control groups. Mass spectrometric techniques are used to establish the stable isotope ratio of any exogenous peptides identified. Peptides exhibiting two predominant isotopic peaks with relative abundances equal to that of the ingested flour mixture can only be derived directly from the wheat proteins themselves. Peptides that exhibit a multitude of isotopic peaks in relative abundances that vary from that of the ingested flour mixture, can only have been formed after complete digestion of the wheat proteins (i.e., after the constituent $^{13}$C and $^{12}$C amino acids had a chance to intermingle). In a follow up experiment patients are fed a flour mixture predigested with proteases. These patients should not exhibit any exogenous peptides derived from wheat proteins but should still exhibit peptides derived from microbial or disease-related synthesis within the body.

Related methods are used to identify if any of the exogenous peptides pass the blood brain barrier (have the potential to cause neurological disorders) and identify their ultimate source. Peptides derived directly from incomplete digestion and malabsorption of food proteins can be detected directly in cerebral spinal fluid samples taken from autistic children after ingestion of the flour mixture according to the methods described herein. By feeding $^{13}$C-enriched amino acids and simultaneously providing intravenous supplementation of one or more amino acids, the likely source of exogenous peptides not directly derived from wheat proteins can be identified. Those peptides of microbial origin in the gut will contain high ratios of $^{13}$C-amino acids. Lower stable isotope contents, particularly of the intravenously administered amino acids, are indicative of peptides synthesized in the blood or in human tissues. The efficacy of peptidase or secretin supplementation can similarly be explored with this technique.

Proving that exogenous peptides originating from the gut appear in cerebral spinal fluid and identifying the ultimate source of these peptides can be used in appropriate clinical treatment of autism. For example, the stable isotope technique can be used in the development of a rapid early diagnostic tool for clinicians, allowing for earlier clinical intervention before the effects of diet or yeast infection become irreversible.

EXAMPLE 6

In this example a culture of *Escherichia coli* DH5α was grown exponentially at 37° C. on a [$^{12}$C]-glucose morpholinopropanesulfonic acid buffered minimal media as described in Neidhardt et al., *J Bacteriol.* 119:736 (1974), to a cell density of $AU_{600}$=0.7. At this cell density 0.84 ml of a 500 mM solution of [$^{13}$C]$_6$-glucose was added to 84 ml of the culture, resulting in a approximate equimolar ratio of [$^{13}$C]$_6$-glucose and [$^{12}$C]$_6$-glucose. Approximately 8 ml aliquots were withdrawn from the culture periodically and quenched in 2 ml ice cold trichloroacetic acid (TCA) to a final concentration of 10% TCA by weight. The quenched samples were centrifuged at 4,000 rpm, 10° C., for 40 min. Aliquots (1 ml) of the TCA supernatants were placed into 2 ml microfuge tubes and concentrated in a Savant SpeedVap to dryness. The samples were resuspended in HPLC-grade water to a total of 0.7 ml combined from the resuspended concentrates for each timepoint sample.

The resuspended TCA soluble fractions were subjected to mass spectrometric analysis in negative ion mode on a PE Biosystems Mariner™ microelectrospray time-of-flight mass spectrometer. The mass spectrometer was calibrated immediately prior to analysis per the manufacturer's instructions. Samples were fed continuously at 0.3 µl/min into the microspray ionization system with a nozzle potential of 160 V and nozzle temperature of 170° C. Mass spectra were accumulated for about 15 min.

The mass spectrometric data were analyzed by dividing the counts determined exactly 6.02013 amu higher than each position by the peak counts in each mass position, yielding a $^{13}$C/$^{12}$C isotope ratio spectrum for all six carbon species. The $^{13}$C/$^{12}$C ratio spectra obtained for the samples taken at each time point were plotted together and manually inspected for peaks that changed consistently over the timed samples. In this analysis it is expected that the zero time spectra would show peaks that were significantly smaller than 1 and spectra from longer time points after substrate addition (i.e., after metabolism of the [$^{13}$C]-glucose) would exhibit a ratio that asymptotically approached an equilibrium value closer to 1.

Manual inspection of the ratio spectra showed seven such potential six carbon metabolites (FIGS. 11 to 17).

Since the equilibrium substrate ratio was expected to be roughly equimolar the actual MS spectra (scaled to the total counts) were analyzed at each of the corresponding $^{12}$C and $^{13}$C positions resulting from the ratio analysis. Three of the seven putative six carbon metabolites were eliminated by this second level analysis because the putative $^{12}$C and $^{13}$C peaks were not found to be of the same magnitude (FIGS. 11, 15, and 17).

Finally, the metabolic flux was determined by curve fit to the equation:

$$Flux_{analyte} = \frac{\ln\left\{\frac{(RA_t - RA_{ss})}{(RA_o - RA_{ss})}\right\}}{(t)(\text{unit of sample})}$$

where $RA_{SS}$ was neglected. Only the metabolites at 150.87 amu (FIG. 12) and 152.88 amu (FIG. 13) were found to have metabolic flux values significantly different from zero and exhibited roughly equimolar peaks at both the $^{13}$C and $^{12}$C positions at long times. These mass positions are the most likely to correspond to real metabolites resulting directly from the six glucose carbons, and thus correspond to a metabolic $C_6$ fingerprint of glucose metabolism by *E. coli* at these growth conditions. The metabolic fluxes of the 150.87 and 152.88 amu metabolites were found to be similar at about $1 \times 10^{-2}$ and $9 \times 10^{-3}$ $s^{-1} AU_{600}^{-1}$, respectively.

A similar analysis was conducted for five carbon metabolites, which suggests that two five carbon metabolites may also be derived from [$^{13}$C]-glucose metabolism (FIGS. 18 and 19). However, only in the long time points does the 278.81 amu metabolite exhibit any significant increase in $^{13}$C content (FIG. 18), suggesting that this peak may be an experimental artifact. The 280.80 amu metabolite appears to exhibit a real flux of about $4 \times 10^{-3}$ $s^{-1} AU_{600}^{-1}$, about half of that observed for the six carbon metabolites. The identities of these metabolites is unknown.

Similar analyses were conducted at the four, three, and two carbon metabolite levels with no apparent $^{13}$C-metabolites resulting from [$^{13}$C]-glucose being found in the mass spectral data.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A method for analyzing a metabolic pathway, comprising:
   (a) administering to a subject a known ratio of a labeled substrate and an unlabeled substrate, wherein said labeled substrate is a substrate labeled with a stable isotope and said unlabeled substrate is said substrate having a natural abundance of said stable isotope;
   (b) allowing the labeled substrate and the unlabeled substrate to be at least partially metabolized by the subject to form a labeled target metabolite and an unlabeled target metabolite;
   (c) generating mass spectral data from a plurality of samples from said subject at a plurality of time points; and
   (d) determining a plurality of relative abundances of said labeled target metabolite to said unlabeled target metabolite from the mass spectral data of at least one of said samples and comparing said plurality of relative abundances to said known ratio of said labeled substrate and said unlabeled substrate.

2. The method of claim 1, further comprising at least partially separating the labeled target metabolites and the unlabeled target metabolites from other biological components in said at least one of said samples prior to determining the plurality of relative abundances.

3. The method of claim 2, wherein the separating comprises performing a plurality of capillary electrophoresis methods in series.

4. The method of claim 3, wherein the plurality of capillary electrophoresis methods are selected from the group consisting of capillary zone electrophoresis, capillary isoelectric focusing and capillary gel electrophoresis.

5. The method of claim 4, wherein the plurality of capillary electrophoresis methods are selected from the group consisting of capillary zone electrophoresis and capillary isoelectric focusing.

6. The method of claim 5, wherein the performing of the capillary electrophoresis methods comprises performing a plurality of capillary zone electrophoresis methods.

7. The method of claim 3, wherein the performing of the capillary electrophoresis methods generate separate fractions for at least one class of metabolite, wherein the class of metabolite is selected from the group consisting of proteins, polysaccharides, carbohydrates, nucleic acids, amino acids, nucleotides, nucleosides, fats, fatty acids and organic acids.

8. The method of claim 3, wherein the separating comprises conducting a non-electrophoretic separation technique prior to conducting the plurality of electrophoresis methods to precipitate at least some of the biological components.

9. The method of claim 1, wherein the stable isotope is selected from the group consisting of $^{13}$C, $^{2}$H, $^{15}$N, $^{18}$O and $^{34}$S.

10. The method of claim 1, wherein the substrate is selected from the group consisting of proteins, carbohydrates, nucleic acids, amino acids, nucleotides, nucleosides, fatty acids, organic acids, and fats.

11. The method of claim 10, wherein the substrate is a protein.

12. The method of claim 1, wherein the plurality of samples are obtained from a bodily fluid, the bodily fluid selected from the group consisting of blood, urine, cerebral fluid, spinal fluid, sweat, and gastrointestinal fluids.

13. The method of claim 1, wherein the plurality of samples are cells, tissue samples or fecal materials.

* * * * *